(12) United States Patent
Losen et al.

(10) Patent No.: US 9,181,344 B2
(45) Date of Patent: Nov. 10, 2015

(54) USE OF EFFECTOR-FUNCTION-DEFICIENT ANTIBODIES FOR TREATMENT OF AUTO-IMMUNE DISEASES

(75) Inventors: Mario Losen, Maastricht (NL); Pilar Martinez-Martinez, Maastricht (NL); Marc H. De Baets, Maasmechelen (BE); Yvo Graus, Odijk (NL); Janine Schuurman, Utrecht (NL); Paul Parren, Utrecht (NL)

(73) Assignee: GENMAB A/S, Copenhagen (DK)

( * ) Notice: Subject to any disclaimer, the term of this patent is extended or adjusted under 35 U.S.C. 154(b) by 1194 days.

(21) Appl. No.: 12/096,196

(22) PCT Filed: Dec. 15, 2006

(86) PCT No.: PCT/DK2006/000719
§ 371 (c)(1),
(2), (4) Date: Oct. 14, 2008

(87) PCT Pub. No.: WO2007/068255
PCT Pub. Date: Jun. 21, 2007

(65) Prior Publication Data
US 2009/0317382 A1   Dec. 24, 2009

Related U.S. Application Data

(60) Provisional application No. 60/750,505, filed on Dec. 15, 2005.

(30) Foreign Application Priority Data

May 31, 2006 (DK) .................................. 2006 00744

(51) Int. Cl.
*C07K 16/28* (2006.01)
*A61K 39/00* (2006.01)

(52) U.S. Cl.
CPC ......... *C07K 16/286* (2013.01); *A61K 2039/505* (2013.01); *C07K 2317/24* (2013.01); *C07K 2317/71* (2013.01)

(58) Field of Classification Search
None
See application file for complete search history.

(56) References Cited

FOREIGN PATENT DOCUMENTS

| WO | 2006/033386 A1 | 3/2006 |
| WO | WO-2007/059782 A1 | 5/2007 |

OTHER PUBLICATIONS

Farrar, J., et al. Int. Immunol. 1997; 9(9): 1311-1318.*
Van Der Zee, J.S.., et al. Clin Exp. Immunol. 1986; 64:415-422.*
Aalberse, Rob C. et al., "Serologic Aspects of IgG4 Antibodies I. Prolonged Immunization Results in an IgG4-Restricted Response," *The Journal of Immunology*, vol. 130(2):722-726 (1983).
Aalberse, Rob C. et al., "The Apparent Monovalency of Human IgG4 is Due to Bispecificity," *Int. Arch. Allergy Immunol.*, vol. 118:187-189 (1999).
Almon, Richard R. et al., "Serum Globulin in Myasthenia Gravis: Inhibition of α-Bungarotoxin Binding to Acetylcholine Receptors," *Science*, vol. 186(4158):55-57 (1974).
Angal, S. et al., "A Single Amino Acid Substitution Abolishes the Heterogeneity of Chimeric Mouse/Human (IgG4) Antibody," *Molecular Immunology*, vol. 30(1):105-108 (1993).
Berman, Phillip W. et al., "Antigenic Modulation of Junctional Acetylcholine Receptor is Not Sufficient to Account for the Development of Myasthenia Gravis in Receptor Immunized Mice," *The Journal of Immunology*, vol. 132(2):711-717 (1984).
Bloom, James W. et al., "Intrachain disulfide bond in the core hinge region of human IgG4," *Protein Science*, vol. 6:407-415 (1997).
Burton, Dennis R. et al., "Square-Dancing Antibodies," *Science*, vol. 317:1507-1508 (2007).
Chamberlain-Banoub, J. et al., "Complement membrane attack is required for endplate damage and clinical disease in passive experimental myasthenia gravis in Lewis rats," *Clinical and Experimental Immunology*, vol. 146:278-286 (2006).
Colcher, David et al., "Characterization and Biodistribution of Recombinant and Recombinant/Chimeric Constructs of Monoclonal Antibody B72.3," *Cancer Research*, vol. 49:1738-1745 (1989).
De Baets, M. et al., "Immunoregulation in Experimental Autoimmune Myasthenia Gravis—about T Cells, Antibodies, and Endplates," *Ann. N.Y. Acad. Sci.*, vol. 998:308-317 (2003).
Edelman, Gerald M. et al., "The Covalent Structure of an Entire □G Immunoglobulin Molecule," Biochemistry, vol. 63:78-85 (1969).
Farrar, Jeremy et al., "Diverse Fab specific for acetylcholine receptor epitopes from a myasthenia gravis thymus combinatorial library," International Immunology, vol. 9(9):1311-1318 (1997).
Farrugia, Maria Elena et al., "MRI and clinical studies of facial and bulbar muscle involvement in MuSK antibody-associated myasthenia gravis," Brain, vol. 129:1481-1492 (2006).
Garraud, Olivier et al., "Class and subclass selection in parasite-specific antibody responses," Trends in Parasitology, vol. 19(7):300-304 (2003).
Gervásio, Othon L. et al., "Development increase in the amount of rapsyn per acetylcholine receptor promotes postsynaptic receptor packing and stability," Developmental Biology, vol. 305:262-275 (2007).
Gervásio, Othon L. et al., "Increased ratio of rapsyn to ACh receptor stabilizes postsynaptic receptors at the mouse neuromuscular synapse," J. Physiol., vol. 562(3):673-685 (2005).
Gomez, Christopher et al., "Anti-acetylcholine receptor antibodies directed against the □-bungarotoxin binding site induce a unique form of experimental myasthenia," Proc. Natl. Acad. Sci. USA, vol. 80:4089-4093 (1983).

(Continued)

*Primary Examiner* — Gerald R Ewoldt
(74) *Attorney, Agent, or Firm* — Nelson Mullins Riley & Scarborough LLP; Jane E. Remillard, Esq.; Christopher L. Frank

(57) ABSTRACT

The invention relates to the treatment of autoimmune diseases and disorders, in particular myasthenia gravis, by administration of effector-function-deficient antibodies, wherein said effector-function-deficient antibodies are capable of competing with one or more of the auto-antibodies involved in mediating the antibody-mediated auto-immune disease or disorder for binding to a target auto-antigen.

7 Claims, 16 Drawing Sheets

(56) References Cited

OTHER PUBLICATIONS

Graus, Yvo F. et al., "Antiacetylcholine Receptor Fab Fragments Isolated from Thymus-derived Phage Display Libraries from Myasthenia Gravis Patients Reflect Predominant Specificities in Serum and Block the Action of Pathogenic Serum Antibodies," Annals New York Academy of Sciences, vol. 841(2):414-417 (1998).

Graus, Y.M.F. et al., "Characterization of anti-acetylcholine receptor (AChR) antibodies from mice differing in susceptibility for experimental autoimmune myasthenia gravis (EAMG)," Clin. Exp. Immunol., vol. 92:506-513 (1993).

Graus, Yvo F. et al., "Human Anti-Nicotinic Acetylcholine Receptor Recombinant Fab Fragments Isolated from Thymus-Derived Phage Display Libraries from Myasthenia Gravis Patients Reflect Predominant Specificities in Serum and Block the Action of Pathogenic Serum Antibodies," The Journal of Immunology, vol. 158:1919-1929 (1997).

Guyon, Thierry et al., "Regulation of Acetylcholine Receptor Gene Expression in Human Myasthenia Gravis Muscles," J. Clin. Invest., vol. 102(1):249-263 (1998).

Heinemann, S. et al., "Modulation of acetylcholine receptor by antibody against the receptor," Proc. Natl. Acad. Sci. USA, vol. 74(7):3090-3094 (1977).

Hoch, Werner et al., "Auto-antibodies to the receptor tyrosine kinase MuSK in patients with myasthenia gravis without acetylcholine receptor antibodies," Nature Medicine, vol. 7(3):365-368 (2001).

Hoedemaekers, A. et al., "Role of the target organ in determining susceptibility to experimental autoimmune myasthenia gravis," Journal of Neuroimmunology, vol. 89:131-141 (1998).

Horgan, Carol et al., "Studies on Antigen Binding by Intact and Hinge-Deleted Chimeric Antibodies," The Journal of Immunology, vol. 150(12):5400-5407 (1993).

Im, Sin-Hyeog et al., "Suppression of experimental myasthenia gravis, a B cell-mediated autoimmune disease, by blockade of IL-18," FASEB J., vol. 15:2140-2148 (2001).

Kaminski, Henry J. et al., "Complement regulators in extraocular muscle and experimental autoimmune myasthenia gravis," Experimental Neurology, vol. 189:333-342 (2004).

Kaneko, Yoshikatsu et al., "Anti-Inflammatory Activity of Immunoglobulin G Resulting from Fc Sialylation," Science, vol. 313:670-673 (2006).

Kao, Ing et al., "Myasthenic Immunoglobulin Accelerates Acetylcholine Receptor Degradation," vol. 196(4289):527-529 (1977).

King, David J. et al., "Expression, purification and characterization of a mouse-human chimeric antibody and chimeric Fab' fragment," Biochem. J., vol. 281:317-323 (1992).

Verschuuren, Jan J.G.M. et al., "Paratope- and Framework-related Cross-reactive Idiotopes on Anti-acetylcholine Receptor Antibodies," The Journal of Immunology, vol. 146:941-948 (1991).

Wakkach, Abdel et al., "Establishment of a Human Thymic Myoid Cell Line, Phenotypic and Functional Characteristics," American Journal of Pathology, vol. 155(4):1229-1240 (1999).

Wang, Zuo-Zhong et al., "Metabolic Stabilization of Muscle Nicotinic Acetylcholine Receptor by Rapsyn," The Journal of Neuroscience, vol. 19(6):1998-2007 (1999).

Wang, Zeng-Yu et al., "Suppression of experimental autoimmune myasthenia gravis by oral administration of acetylcholine receptor," Journal of Neuroimmunology, vol. 44:209-214 (1993).

Wu, Jian-Ming et al., "Specific Immunotherapy of Experimental Myasthenia Gravis in Vitro: The "Guided Missle" Strategy," Cellular Immunology, vol. 208:137-147 (2001).

Zeidel, Maria et al., "Genetic and Functional Characterization of Human Autoantibodies Using Combinatorial Phage Display Libraries," Annals New York Academy of Sciences, vol. 764:559-564 (1995).

Aalberse, Rob C. et al., "IgG4 breaking the rules," Immunology, vol. 105:9-19 (2002).

Chapman, Andrew P. et al., "Therapeutic antibody fragments with prolonged in vivo half-lives," Nature Biotechnology, vol. 17:780-783 (1999).

Fostieri, Efrosini et al., "Isolation of potent human Fab fragments against a novel highly immunogenic region on human muscle acetylcholine receptor which protect the receptor from myasthenic autoantibodies," Eur. J. Immunol., vol. 35:632-643 (2005).

Isaacs, John D. et al., "Therapy with Monoclonal Antibodies. II. The Contribution of Fcgamma Receptor Binding and the Influence of CH1 and CH3 Domains on In Vivo Effector Function," The Journal of Immunology, vol. 161:3862-3869 (1998).

Newman, Roland et al., "Modification of the Fc Region of a Primatized IgG Antibody to Human CD4 Retains Its Ability to Modulate CD4 Receptors but Does Not Deplete CD4+ T Cells in Chimpanzees," Clinical Oncology, vol. 98 (2):164-174 (2001).

Protopapadakis, Evdokia et al., "Isolation and characterization of human anti-acetylcholine receptor monoclonal antibodies from transgenic mice expressing human immunoglobulin loci," Eur. J. Immunol., vol. 35:1960-1968 (2005).

Reddy, Manjula P. et al., "Elimination of Fc Receptor-Dependent Effector Functions of a Modified IgG4 Monoclonal Antibody to Human CD4," The Journal of Immunology, vol. 164:1915-1933 (2000).

Sophianos, Demetris et al., "Fab Fragments of Monoclonal Antibodies Protect the Human Acetylcholine Receptor against Antigenic Modulation Caused by Myasthenic Sera," Journal of Autoimmunity, vol. 2:777-789 (1989).

Yamamoto, Teiji, "Intravenous Immunoglobulin Therapy and Plasma Exchange Therapy," Clinical Neuroscience, vol. 23(4):454-456 (2005).

Lang, Bethan et al., "Plasma from myasthenia gravis patients reduces acetylcholine receptor agonist-induced Na+ flux into TE671 cell line," Journal of Neuroimmunology, vol. 19:41-148 (1988).

Lavrnic. D. et al., "The features of myasthenia gravis with autoantibodies to MuSK," J. Neural Neurosurg. Psychiatry, vol. 76:1099-1102 (2005).

Lennon, Venda A. et al., "Role of Complement in the Pathogenesis of Experimental Autoimmune Myasthenia Gravis," J. Exp. Med., vol. 147.973-983 (1978).

Lindstrom, J. M. et al., "Experimental Autoimmune Myasthenia Gravis and Myasthenia Gravis: Biochemical and Immunochemical Aspects," Annals New York Academy of Sciences, vol. 274:254-274—(1976).

Lindstrom, Jon M. et al., "Pathological Mechanisms in Experimental Autoimmune Myasthenia Gravis. II. Passive Transfer of Experimental Autoimmune Myasthenia Gravis in Rats with Anti-Acetylcholine Receptor Antibodies," The Journal of Experimental Medicine, vol. 144:739-753 (1976).

Lindstrom, Jon et al., "Production and Assay of Antibodies to Acetylcholine Receptors," Methods in Enzymology, vol. 74:432-460 (1981).

Losen, Mario et al., "Increased expression of rapsyn in muscles prevents acetylcholine receptor loss in experimental autoimmure myasthenia gravis," Brain, vol. 128:2327-2337 (2005).

Losen, Mario, "Therapeutic Approaches for the Protection of Neurological Synapses in Autoimmunity," Ph.D thesis, University of Maastricht (2006).

Losen, Mario, "Treatment of Myasthenia Gravis by Preventing Acetylcholine Receptor Modulation," Ann. N.Y. Acad. Sci., vol. 1132: 174-179 (2008)

Loutrari, H. et al., "Expression of human-Torpedo hybrid acetylcholine receptor (AChR) for analysing the subunit specificity of antibodies in sera from patients with myasthenia gravis (MG)," Clin. Exp. Immunol., vol. 109:538-546 (1997).

Loutrari, Heleni et al., "Passive transfer of experimental myasthenia gravis via antigenic modulation of acetylcholine receptor," Eur. J. Immunol., vol. 22-2449-2452 (1992).

Luo, Guang X. et al., "Identification of a peptide that protects the human acetylcholine receptor against antigenic modulation," Journal of Immunological Methods, vol. 251:177-186 (2001).

Luther, Michael A. et al., "A Muscle Acetylcholine Receptor is Expressed in the Human Cerebellar Medulloblastoma Cell Line TE671," The Journal of Neuroscience, vol. 9(3):1082-1096 (1989).

Margni, Richardo A. et al., "Nonprecipitating Asymmetric Antibodies," Ann. Rev. Immunol., vol. 6:535-554 (1988).

(56) References Cited

OTHER PUBLICATIONS

Martinez-Martinez, Pilar et al., "Overexpression of Rapsyn in Rat Muscle Increases Acetylcholine Receptor Levels in Chronic Experimental Autoimmune Myasthenia Gravis." The Americal Journal of Pathology, vol. 170 (2):644-657 (2007).

Nakagawa, Takemasa et al., "The Role of IgG4e as Blocking Antibodies in Asthmatics and in Bee Keepers," Int. Archs. Allergy Appl. Immun., vol. 77:204-205 (1985).

Nanda, Anil et al., "Dose dependence and time course of the immunologic response to administration of standardized cat allergen extract," J. Allergy Clin. Immunol., vol. 114:1339-1344 (2004).

Nouri-Aria, Kayhan T. et al., "Grass Pollen Immunotherapy Induces Mucosal and Peripheral IL-10 Responses and Blocking IgG Activity," The Journal of Immunology, vol. 172:3252-3259 (2004).

Osserman, Kermit E. et al., "Studies in Myasthenia Gravis: Review of a Twenty-Year Experience in over 1200 Patients." The Mount Sinai Journal of Medicine, vol. 38(6):497-537 (1971).

Papanastasiou, Danai et al., "Prevention of passively transferred experimental autoimmune myasthenia gravis by Fab fragments of monoclonal antibodies directed against the main immunogenic region of the acetylcholine receptor," Journal of Neuroimmunology, vol. 104:124-132 (2000).

Patrick, Jim et al., "Autoimmune Response to Acetylcholine Receptor," Science, vol. 180(4088):871-872 (1973).

Petersen, Jens G. Liske et al., "An in Vitro System for Studying the Kinetics of Interchain Disulfide Bond Formation in Immunoglobulin G," The Journal of Biological Chemistry, vol. 249(17):5633-5641 (1974).

Phillips, William D. et al., "Rapsyn and Agrin Slow the Metabolic Degradation of the Acetylcholine Receptor," Molecular and Cellular Neuroscience, vol. 10:16-26 (1997).

Rey, Elena et al., "Characterization of Human Anti-acetylcholine Receptor Monoclonal Autoantibodies from the Peripheral Blood of a Myasthenia Gravis Patient Using Combinatorial Libraries," Clinical Immunology, vol. 96 (3):269-279 (2000).

Richman, David P. et al., "Antibody Effector Mechanisms in Myasthenai Gravis, The Complement Hypothesis," Annals New York Academy of Sciences, vol. 841:450-465 (1998).

Rodgaard, A. et al., "Acetylcholine receptor antibody in myasthenia gravis predominance if IgG subclasses 1 and 3," Clin. Exp. Immunol., vol. 67:82-88 (1987).

Saphire, Erica Ollmann et al., "Contrasting IgG Structures Reveal Extreme Asymmetry and Flexibility," J. Mol. Biol., vol. 319:9-18 (2002).

Scallon, Bernard J. et al., "A Review of Antibody Therapeutics and Antibody-Related Technologies for Oncology," J. Immunother., vol. 29(4):351-364 (2006).

Schuurman, J. et al., "Normal human immunoglobulin G4 is bispecific: it has two different antigen-combining sites," Immunology, vol. 97:693-698 (1999).

Schuurman, Janine et al., "The inter-heavy chain disulfide bonds of IgG4 are in equilibrium with intra-chain disulfide bonds," Molecular Immunology, vol. 38:1-8 (2001).

Shields, Robert L. et al., "Lack of Fucose on Human IgG1 N-Linked Oligosaccharide Improves Binding to Human FcgRIII and Antibody-dependent Cellular Toxicity," The Journal of Biological Chemistry, vol. 277(30):26733-26740 (2002).

Sieb, Joern P., "Myasthenia gravis: emerging new therapy options." Current Opinion in Pharmacology, vol. 5:303-307 (2005).

Souroujon, Miry C. et al., "The treatment of passively transferred experimental myasthenia with anti-idiolypic antibodies," Neurology, vol. 36:622-625 (1986).

Stassen, Maurice H. et al., "Characterization of a Fully Human IgG1 Reconstructed from an Anti-AChR Fab," Ann. N.Y. Acad. Sci., vol. 998:399-400 (2003).

Stassen, Maurice H.W. et al., "Experimental autoimmune myasthenia gravis in mice expressing human immunoglobulin loci," Journal of Neuroimmunology, vol. 135:56-61 (2003).

Steinman, Lawrence, "The Use of Monoclonal Antibodies for Treatment of Autoimmune Disease," Journal of Clinical Immunology, vol. 10(6):30S-39S (1990).

Tarrab-Hazdzi, Rebeca et al., "Experimental autoimmune myasthenia induced in monkeys by purified acetylcholine receptor," Nature. vol. 256:128-130 (1975).

Teeling, Jessica L. et al., "Characterization of new human CD20 monoclonal antibodies with potent cytolytic activity against non-Hodgkin lymphomas." Blood. vol. 104(6); 1793-1800 (2004).

Toyka, Klaus V. et al., "Myasthenia Gravis: Passive Transfer from Man to Mouse," Science. vol. 190(4212):397-399 (1975).

Toyka, K.V. et al., "Passively transferred myasthenia gravis: protection of mouse endplatges by Fab fragments from human myasthenic IgG," Journal of Neurology, Neurosurgery, and Psychiatry. vol. 43:836-840 (1980).

Toyka, Klaus V. et al., "Myasthenia Gravis, Study of Humoral Immune Mechanisms by Passive Transfer to Mice," The New England Journal of Medicine, vol. 296(3):125-131 (1977).

Tuzun, Erdem et al., "Genetic Evidence for Involvement of Classical Complement Pathway in Induction of Experimental Autoimmune Myasthenia Gravis," The Journal of Immunology, vol. 171:3847-3854 (2003).

Tzartos, Socrates J. et al., "Anatomy of the antigenic structure of a large membrane autoantigen, the muscle-type nicotinic acetylcholine receptor," Immunological Reviews, vol. 163:89-120 (1998).

Tzartos, Socrates J. et al., "Monoclonal antibodies used to probe acetylcholine receptor structure: Localization of the main immunogenic region and detection of similarities between subunits," Proc. Natl. Acad. Sci. USA, vol. 77 (2):755-759 (1980).

Tzartos, Socrates J. et al., "Specifities of antibodies to acetylcholine receptors in sera from myasthenia gravis patients measured by monoclonal antibodies," Proc. Natl. Acad. Sci. USA, vol. 79:188-192 (1982).

Tzartos, S.J. et al., "The Main Immunogenic Region (MIR) of the Nicotinic Acetylcholine Receptor and the Anti-MIR Antibodies," Molecular Neurobiology, vol. 5:1-28 (1991).

Van Der Neut Kolfschoten, Marjin et al., "Anti-inflammatory Activity of Human IgG4 Antibodies by Dynamic Fab Arm Exchange," Science, vol. 317:1554-1557 (2007).

Van Der Zee, J.S. et al., "Inhibition of complement activation by IgG4 antibodies," Clin. Exp. Immunol., vol. 64:415-422 (1980).

Van Der Zee, Jaring S. et al., "Serologic Aspects of IgG4 Antibodies II. IgG4 Antibodies form Small, Nonprecipitating Immune Complexes Due to Functional Monovalency," The Journal of Immunology, vol. 137 (11):3566-3571 (1986).

Vercelli, Donata et al., "To E or not to E?," Int. Arch. Allergy Immunol., vol. 116:1-4 (1998).

* cited by examiner

FIGURE 1

| Name | Oligo Sequence | SEQ ID No |
|---|---|---|
| IGG4gene2f | GTAGAAGCTTACCATCGCGGATAGACAAGAACC | SEQ ID No:9 |
| IGG4gene2r | TGAGAATTCGGTGGGTGCTTTATTTCCATGCT | SEQ ID No:10 |
| MGHCexfor | GATAAGCTTGCCGCCACCATGGAATGGAGCTGGGTCTTTCT | SEQ ID No:11 |
| MGHCexrev | GATCGTCTCGGGCCCTTGGTGGAGGCCGATGAG | SEQ ID No:12 |
| MGLCexfor | GATAAGCTTGCCGCCACCATGGGTGTGCCCACTCAGGTCCT | SEQ ID No:13 |
| pConG1seq1 | GAAGACTTAAGGCAGCGGCAGAA | SEQ ID No:14 |
| pee13.4seqrev | TGCATTCATTTTATGTTTCAGGT | SEQ ID No:15 |
| RACElambda1 | CCAGTGTGGCCTTGTTGGCTTGAAG | SEQ ID No:16 |
| ON-NheI-mutm | CTCTCCCTGTCTCCGGGTAAGCTAGCGCGACGGCCGGCAAGCCC | SEQ ID No:17 |
| ON-NheI-Flag | AAAGCTAGCGGACTACAAGGACGACGATGACAAGTGAGTGCGACGGCCGGCAAG | SEQ ID No:18 |
| LCseq3 | TGTACTTTGGCCTCTCTGGGATA | SEQ ID No.21 |
| 7D8VLexrev | CTGGAGATTAAACGTACGGTGGCTGCACC | SEQ ID No.22 |
| 7D8VLexfor | GCGACTAAGCTTGCCGCCACCATGGAAGCCCCAGCTCAGCTTCTC | SEQ ID No.23 |
| 7D8VHexfor | GCTGAAAGCTTGCCGCCACCATGGAGTTGGGACTGAGCTGGATT | SEQ ID No.24 |
| pConKseq1 | GTAGTCTGAGCAGTACTCGTTGC | SEQ ID No.25 |
| pConG1seq1 | GAAGACTTAAGGCAGCGGCAGAA | SEQ ID No.26 |
| HCseq5 | GGTCAGGGCGCCTGAGTTCCACG | SEQ ID No.27 |
| HCseq11 | ATGCAGGCTACTCTAGGGCACCT | SEQ ID No.28 |
| 2f8HCexrev | GAAGACCGATGGGCCCTTGGTGCTAGCTGAGGAGAC | SEQ ID No.29 |
| IGG4gene2r | TGAGAATTCGGTGGGTGCTTTATTTCCATGCT | SEQ ID No.30 |
| IGG4gene2f | GTAGAAGCTTACCATCGCGGATAGACAAGAACC | SEQ ID No.31 |
| IGG4S228Pf | GGTCCCCCATGCCCACCATGCCCGGGTAAGCCA | SEQ ID No.32 |
| IGG4S228Pr | TGGCTTACCCGGGCATGGTGGGCATGGGGGACC | SEQ ID No.33 |

FIGURE 9
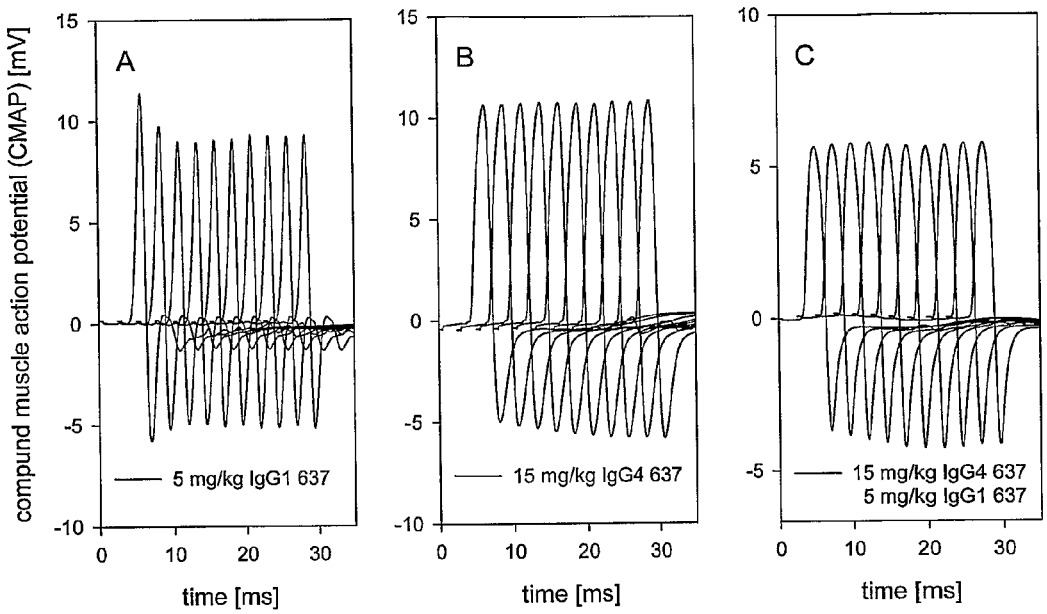
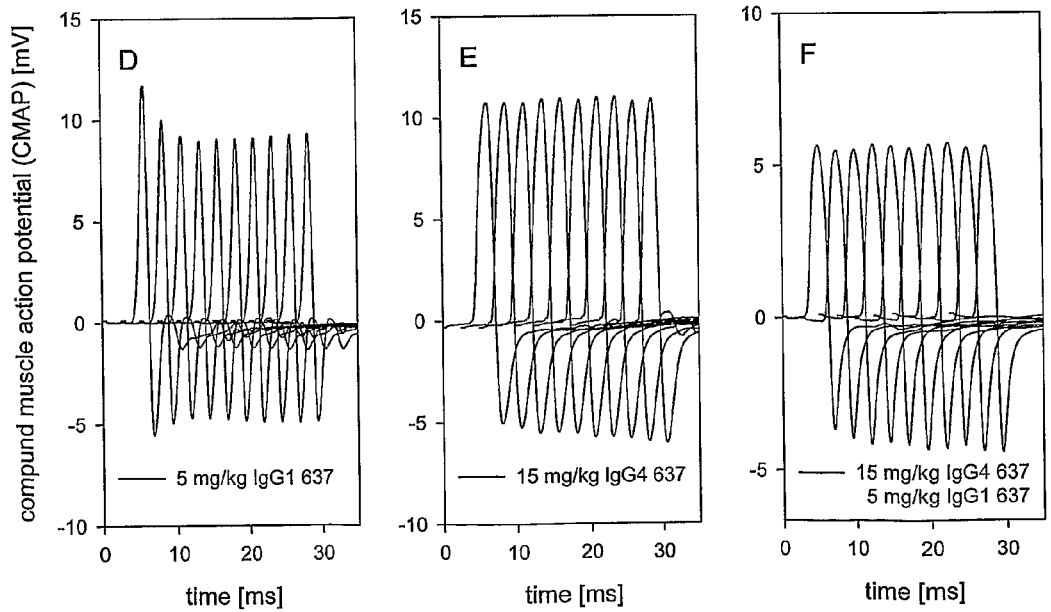

5 mg/kg IgG1 637

Stimulation at 3 Hz, 60.6 mA

| Pot. No. | Peak Amp. [mV] | Amp. Decr. [%] | Area [mVms] | Area Decr. [%] |
|---|---|---|---|---|
| 1 | 11.34 | 0 | 12.80 | 0 |
| 2 | 9.71 | 14 | 10.90 | 15 |
| 3 | 8.99 | 21 | 10.00 | 22 |
| 4 | 8.94 | 21 | 9.93 | 25 |
| 5 | 9.04 | 20 | 9.91 | 22 |
| 6 | 9.08 | 20 | 9.93 | 23 |
| 7 | 9.27 | 18 | 10.00 | 22 |
| 8 | 9.20 | 19 | 10.10 | 21 |
| 9 | 9.16 | 19 | 10.00 | 22 |
| 10 | 9.25 | 18 | 10.00 | 22 |

15 mg/kg IgG4 637

Stimulation at 3 Hz, 53.1 mA

| Pot. No. | Peak Amp. [mV] | Amp. Decr. [%] | Area [mVms] | Area Decr. [%] |
|---|---|---|---|---|
| 1 | 10.75 | 0 | 21.20 | 0 |
| 2 | 10.80 | 0 | 21.00 | 1 |
| 3 | 10.82 | -1 | 21.00 | 1 |
| 4 | 10.84 | -1 | 21.00 | 1 |
| 5 | 10.84 | -1 | 20.90 | 1 |
| 6 | 10.85 | -1 | 20.80 | 2 |
| 7 | 10.85 | -1 | 20.80 | 2 |
| 8 | 10.95 | -2 | 20.90 | 1 |
| 9 | 10.95 | -2 | 20.80 | 2 |
| 10 | 11.01 | -2 | 20.90 | 1 |

15 mg/kg IgG4 637 + 5 mg/kg IgG1 637

Stimulation at 3 Hz, 62.9 mA

| Pot. No. | Peak Amp. [mV] | Amp. Decr. [%] | Area [mVms] | Area Decr. [%] |
|---|---|---|---|---|
| 1 | 5.67 | 0 | 11.80 | 0 |
| 2 | 5.68 | 0 | 12.00 | -2 |
| 3 | 5.67 | 0 | 12.00 | -2 |
| 4 | 5.67 | 0 | 11.90 | -1 |
| 5 | 5.65 | 0 | 11.60 | 2 |
| 6 | 5.69 | 0 | 11.40 | 3 |
| 7 | 5.72 | -1 | 11.40 | 3 |
| 8 | 5.75 | -1 | 11.40 | 3 |
| 9 | 5.79 | -2 | 11.60 | 2 |
| 10 | 5.76 | -2 | 11.70 | 1 |

5 mg/kg IgG1 637

Stimulation at 5 Hz, 60.6 mA

| Pot. No. | Peak Amp. [mV] | Amp. Decr. [%] | Area [mVms] | Area Decr. [%] |
|---|---|---|---|---|
| 1 | 11.62 | 0 | 13.30 | 0 |
| 2 | 9.96 | 14 | 11.20 | 16 |
| 3 | 9.17 | 21 | 10.20 | 23 |
| 4 | 8.91 | 23 | 9.97 | 25 |
| 5 | 9.03 | 22 | 9.95 | 25 |
| 6 | 9.02 | 22 | 9.93 | 25 |
| 7 | 9.07 | 22 | 9.91 | 25 |
| 8 | 9.15 | 21 | 9.97 | 25 |
| 9 | 9.21 | 21 | 10.00 | 25 |
| 10 | 9.28 | 20 | 10.00 | 25 |

15 mg/kg IgG4 637

Stimulation at 5 Hz, 53.1 mA

| Pot. No. | Peak Amp. [mV] | Amp. Decr. [%] | Area [mVms] | Area Decr. [%] |
|---|---|---|---|---|
| 1 | 10.80 | 0 | 21.40 | 0 |
| 2 | 10.88 | -1 | 20.90 | 2 |
| 3 | 10.87 | -1 | 20.60 | 4 |
| 4 | 10.89 | -1 | 21.00 | 2 |
| 5 | 10.97 | -2 | 21.00 | 2 |
| 6 | 10.95 | -1 | 20.70 | 3 |
| 7 | 10.89 | -1 | 21.10 | 1 |
| 8 | 11.02 | -2 | 21.00 | 2 |
| 9 | 10.97 | -2 | 20.44 | 5 |
| 10 | 11.04 | -2 | 20.30 | 5 |

15 mg/kg IgG4 637 + 5 mg/kg IgG1 637

Stimulation at 5 Hz, 62.9 mA

| Pot. No. | Peak Amp. [mV] | Amp. Decr. [%] | Area [mVms] | Area Decr. [%] |
|---|---|---|---|---|
| 1 | 5.64 | 0 | 11.70 | 0 |
| 2 | 5.58 | 1 | 11.10 | 5 |
| 3 | 5.52 | 2 | 11.00 | 6 |
| 4 | 5.65 | 0 | 11.40 | 3 |
| 5 | 5.72 | -1 | 11.20 | 4 |
| 6 | 5.61 | 1 | 11.00 | 6 |
| 7 | 5.61 | 1 | 11.30 | 3 |
| 8 | 5.73 | -2 | 11.40 | 3 |
| 9 | 5.69 | -1 | 11.00 | 6 |
| 10 | 5.60 | 1 | 11.00 | 6 |

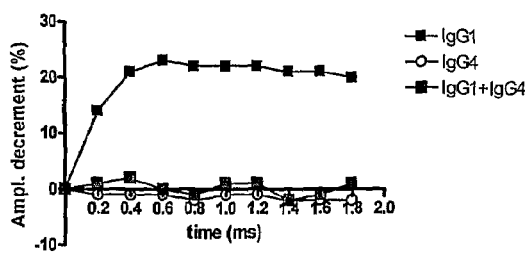

Decrement in EMG Amplitude decrement

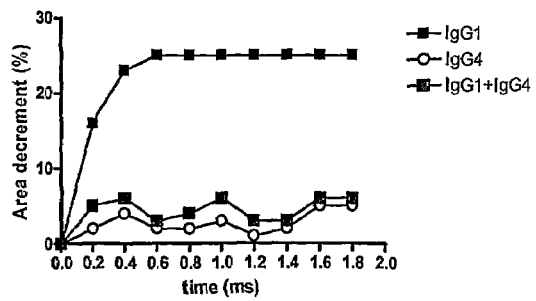

Decrement in EMG Area decrement

FIGURE 12

| number of animals | antibody | 3 doses of | total cumulative dose | decremental response upon repetitive nerve stimulation | clinical symptoms |
|---|---|---|---|---|---|
| 1 | IgG1 637 | 0.5 mg/kg/day | 1.5 mg/kg | - | - |
| 1 | IgG1 637 | 1.0 mg/kg/day | 3 mg/kg | + | - |
| 1 | IgG1 637 | 5.0 mg/kg/day | 15 mg/kg | + | + |
| 4 | IVIg<br>IgG1 637 | 5.0 mg/kg/day<br>1.7 mg/kg/day | 15 mg/kg<br>5 mg/kg | + (3/4) | + (4/4) |
| 2 | IgG4 637<br>IVIg | 5.0 mg/kg/day<br>1.7 mg/kg/day | 15 mg/kg<br>5 mg/kg | - (2/2) | - (2/2) |
| 5 | IgG4 637<br>IgG1 637 | 5.0 mg/kg/day<br>1.7 mg/kg/day | 15 mg/kg<br>5 mg/kg | - (5/5) | - (5/5) |

FIGURE 13
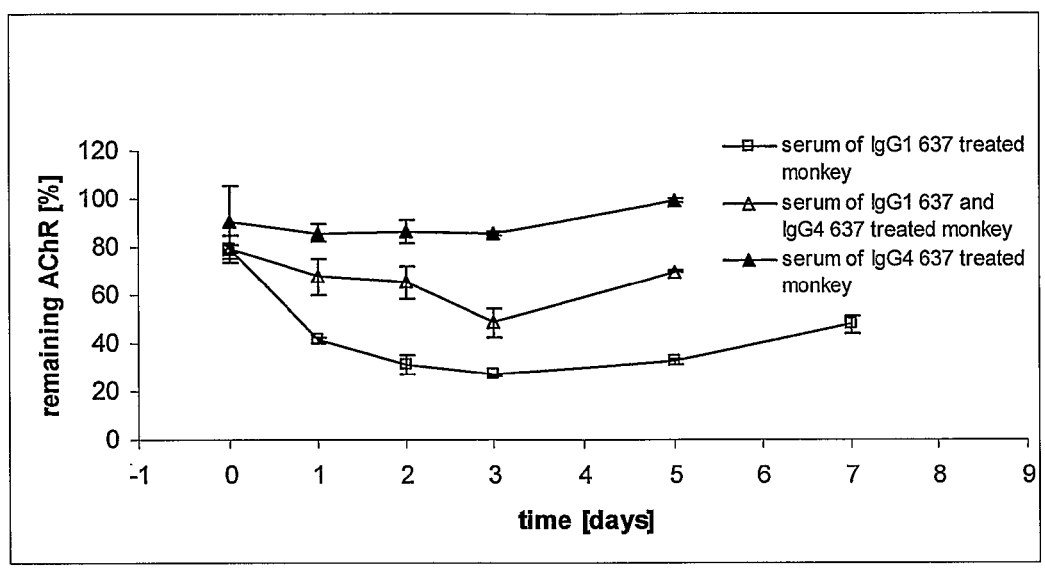
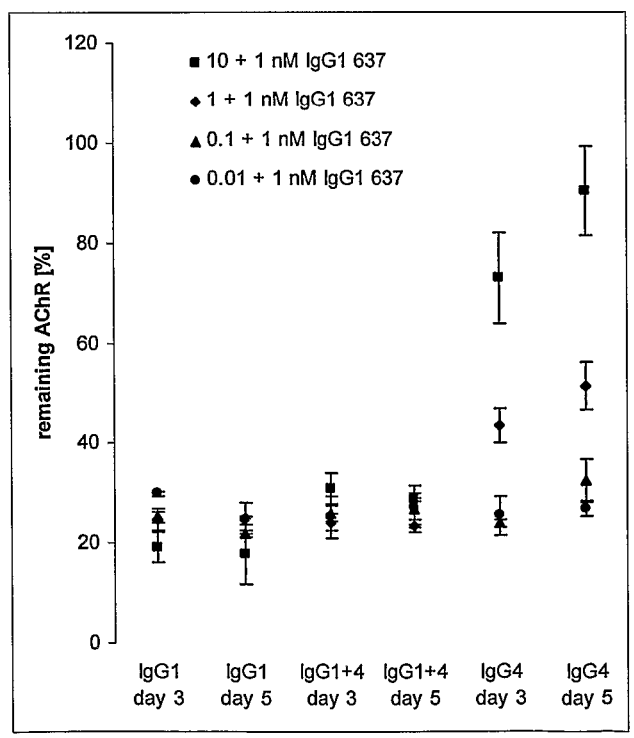

SEQUENCE LISTING

<160> NUMBER OF SEQ IDS: 33

<210> SEQ ID NO 1
<211> LENGTH: 378
<212> TYPE: DNA
<213> ORGANISM: Homo sapiens

<400> SEQUENCE: 1
gaggttcagc tgctcgagtc tgggggagac ttggtcaagc ctggagggtc cctgagactc     60
tcctgtgcag cctctggatt caaatccact gactactaca tggcctgggt ccgccaggct    120

```
ccagggaggg ggctggagtg ggtctcattc attagtggtc gtgttttcac aaactacacc    180
gcctctgtga ggggccgatt caccgtcttc agagaggacg acaacacctc ggtgtatctt    240
cagatgagcc gcctgagagt cgaagacacg gccgtctact actgtgcgag actgcgggga    300 attttttcgag ggcccctcaa acccctagag tactacttcg atctctgggg ccgtggcacc    360
ctggtcactg tctcatcg                                                   378
```

<210> SEQ ID NO 2
<211> LENGTH: 126
<212> TYPE: PRT
<213> ORGANISM: Homo sapiens

<400> SEQUENCE: 2

```
Glu Val Gln Leu Leu Glu Ser Gly Gly Asp Leu Val Lys Pro Gly Gly
 1               5                  10                  15

Ser Leu Arg Leu Ser Cys Ala Ala Ser Gly Phe Lys Ser Thr Asp Tyr
            20                  25                  30

Tyr Met Ala Trp Val Arg Gln Ala Pro Gly Arg Gly Leu Glu Trp Val
        35                  40                  45

Ser Phe Ile Ser Gly Arg Val Phe Thr Asn Tyr Thr Ala Ser Val Arg
    50                  55                  60

Gly Arg Phe Thr Val Phe Arg Glu Asp Asp Asn Thr Ser Val Tyr Leu
65                  70                  75                  80

Gln Met Ser Arg Leu Arg Val Glu Asp Thr Ala Val Tyr Tyr Cys Ala
                85                  90                  95

Arg Leu Arg Gly Ile Phe Arg Gly Pro Leu Lys Pro Leu Glu Tyr Tyr
            100                 105                 110

Phe Asp Leu Trp Gly Arg Gly Thr Leu Val Thr Val Ser Ser
        115                 120                 125
```

<210> SEQ ID NO 3
<211> LENGTH: 333
<212> TYPE: DNA
<213> ORGANISM: Homo sapiens

<400> SEQUENCE: 3

```
gagatcgagc tcactcagcc ccactctgtg tcggagtctc ggggaagac ggtaaccatc      60 tcctgcaccc gcagcagtgg cagcattgcc agcaactatg tgcagtgta ccagcagcgc    120 ccgggcagtt cccccaccac tgtgatctat gaggataacc aaagaccctc tggggtccct    180
gatcggttct ctggctccat cgacagctcc tccaactctg cctccctcac catctctgga    240
ctgaagactg aggacgaggc tgactactac tgtcagtctt atgatagcaa ctctgggggg    300
agggtgttcg gcggagggac caagctgacc gtc                                  333
```

<210> SEQ ID NO 4
<211> LENGTH: 111
<212> TYPE: PRT
<213> ORGANISM: Homo sapiens

<400> SEQUENCE: 4

```
Glu Ile Glu Leu Thr Gln Pro His Ser Val Ser Glu Ser Pro Gly Lys
 1               5                  10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45
```

Ile Tyr Glu Asp Asn Gln Arg Pro Ser Gly Val Pro Asp Arg Phe Ser
 50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Asn Ser Gly Gly Arg Val Phe Gly Gly Gly Thr Lys Leu Thr Val
             100                 105                 110

<210> SEQ ID NO 5
<211> LENGTH: 1588
<212> TYPE: DNA
<213> ORGANISM: Homo sapiens

<400> SEQUENCE: 5

| | | | | | |
|---|---|---|---|---|---|
| gctagcacca | agggcccatc | cgtcttcccc | ctggcgccct | gctccaggag | cacctccgag | 60 |
| agcacagccg | ccctgggctg | cctggtcaag | gactacttcc | ccgaaccggt | gacggtgtcg | 120 |
| tggaactcag | gcgccctgac | cagcggcgtg | cacaccttcc | cggctgtcct | acagtcctca | 180 |
| ggactctact | ccctcagcag | cgtggtgacc | gtgccctcca | gcagcttggg | cacgaagacc | 240 |
| tacacctgca | acgtagatca | caagcccagc | aacaccaagg | tggacaagag | agttggtgag | 300 |
| aggccagcac | agggagggag | ggtgtctgct | ggaagccagg | ctcagccctc | ctgcctggac | 360 |
| gcaccccggc | tgtgcagccc | cagcccaggg | cagcaaggca | tgccccatct | gtcctcac | 420 |
| ccggaggcct | ctgaccaccc | cactcatgct | cagggagagg | gtcttctgga | tttttccacc | 480 |
| aggctccggg | cagccacagg | ctggatgccc | tacccccagg | ccctgcgcat | acaggggcag | 540 |
| gtgctgcgct | cagacctgcc | aagagccata | tccggaggga | ccctgcccct | gacctaagcc | 600 |
| caccccaaag | gccaaactct | ccactccctc | agctcagaca | ccttctctcc | tcccagatct | 660 |
| gagtaactcc | caatcttctc | tctgcagagt | ccaaatatgg | tccccatgc | ccatcatgcc | 720 |
| caggtaagc | aacccaggcc | tcgccctcca | gctcaaggcg | ggacaggtgc | cctagagtag | 780 |
| cctgcatcca | gggacaggcc | ccagccgggt | gctgacgcat | ccacctccat | ctcttcctca | 840 |
| gcacctgagt | tcctgggggg | accatcagtc | ttcctgttcc | ccccaaaacc | caaggacact | 900 |
| ctcatgatct | cccggacccc | tgaggtcacg | tgcgtggtgg | tggacgtgag | ccaggaagac | 960 |
| cccgaggtcc | agttcaactg | gtacgtggat | ggcgtggagg | tgcataatgc | caagacaaag | 1020 |
| ccgcgggagg | agcagttcaa | cagcacgtac | cgtgtggtca | gcgtcctcac | cgtcctgcac | 1080 |
| caggactggc | tgaacggcaa | ggagtacaag | tgcaaggtct | ccaacaaagg | cctcccgtcc | 1140 |
| tccatcgaga | aaaccatctc | caaagccaaa | ggtgggaccc | acggggtgcg | agggccacat | 1200 |
| ggacagaggt | cagctcggcc | caccctctgc | cctgggagtg | accgctgtgc | caacctctgt | 1260 |
| ccctacaggg | cagccccgag | agccacaggt | gtacaccctg | cccccatccc | aggaggagat | 1320 |
| gaccaagaac | caggtcagcc | tgacctgcct | ggtcaaaggc | ttctaccca | gcgacatcgc | 1380 |
| cgtggagtgg | gagagcaatg | ggcagccgga | gaacaactac | aagaccacgc | ctcccgtgct | 1440 |
| ggactccgac | ggctccttct | tcctctacag | caggctaacc | gtggacaaga | gcaggtggca | 1500 |
| ggaggggaat | gtcttctcat | gctccgtgat | gcatgaggct | ctgcacaacc | actacacaca | 1560 |
| gaagagcctc | tccctgtctc | tgggtaaa | | | | 1588 |

<210> SEQ ID NO 6
<211> LENGTH: 327
<212> TYPE: PRT
<213> ORGANISM: Homo sapiens

<400> SEQUENCE: 6

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 7
<211> LENGTH: 321
<212> TYPE: DNA
<213> ORGANISM: Homo sapiens

<400> SEQUENCE: 7

```
ctaggtcagc ccaaggctgc ccctcggtc actctgttcc cgccctcctc tgaggagctt      60
caagccaaca aggccacact ggtgtgtctc ataagtgact tctacccggg agccgtgaca     120
gtggcctgga aggcagatag cagccccgtc aaggcgggag tggagaccac cacaccctcc    180
```

```
aaacaaagca acaacaagta cgcggccagc agctacctga gcctgacgcc tgagcagtgg      240
aagtcccaca gaagctacag ctgccaggtc acgcatgaag ggagcaccgt ggagaagaca      300 gtggcccta cagaatgttc a                                                 321
```

<210> SEQ ID NO 8
<211> LENGTH: 107
<212> TYPE: PRT
<213> ORGANISM: Homo sapiens

<400> SEQUENCE: 8

```
Leu Gly Gln Pro Lys Ala Ala Pro Ser Val Thr Leu Phe Pro Pro Ser
1               5                   10                  15

Ser Glu Glu Leu Gln Ala Asn Lys Ala Thr Leu Val Cys Leu Ile Ser
            20                  25                  30

Asp Phe Tyr Pro Gly Ala Val Thr Val Ala Trp Lys Ala Asp Ser Ser
        35                  40                  45

Pro Val Lys Ala Gly Val Glu Thr Thr Thr Pro Ser Lys Gln Ser Asn
    50                  55                  60

Asn Lys Tyr Ala Ala Ser Ser Tyr Leu Ser Leu Thr Pro Glu Gln Trp
65                  70                  75                  80

Lys Ser His Arg Ser Tyr Ser Cys Gln Val Thr His Glu Gly Ser Thr
                85                  90                  95

Val Glu Lys Thr Val Ala Pro Thr Glu Cys Ser
            100                 105
```

<210> SEQ ID NO 9
<211> LENGTH: 33
<212> TYPE: DNA
<213> ORGANISM: Homo sapiens

<400> SEQUENCE: 9

```
gtagaagctt accatcgcgg atagacaaga acc                                   33
```

<210> SEQ ID NO 10
<211> LENGTH: 32
<212> TYPE: DNA
<213> ORGANISM: Homo sapiens

<400> SEQUENCE: 10

```
tgagaattcg gtgggtgctt tatttccatg ct                                    32
```

<210> SEQ ID NO 11
<211> LENGTH: 41
<212> TYPE: DNA
<213> ORGANISM: Homo sapiens

<400> SEQUENCE: 11

```
gataagcttg ccgccaccat ggaatggagc tgggtctttc t                          41
```

<210> SEQ ID NO 12
<211> LENGTH: 33
<212> TYPE: DNA
<213> ORGANISM: Homo sapiens

<400> SEQUENCE: 12

```
gatcgtctcg ggcccttggt ggaggccgat gag                                   33
```

<210> SEQ ID NO 13
<211> LENGTH: 41

<212> TYPE: DNA
<213> ORGANISM: Homo sapiens

<400> SEQUENCE: 13
gataagcttg ccgccaccat gggtgtgccc actcaggtcc t           41

<210> SEQ ID NO 14
<211> LENGTH: 23
<212> TYPE: DNA
<213> ORGANISM: Homo sapiens

<400> SEQUENCE: 14
gaagacttaa ggcagcggca gaa                              23

<210> SEQ ID NO 15
<211> LENGTH: 23
<212> TYPE: DNA
<213> ORGANISM: Homo sapiens

<400> SEQUENCE: 15
tgcattcatt ttatgtttca ggt                              23

<210> SEQ ID NO 16
<211> LENGTH: 25
<212> TYPE: DNA
<213> ORGANISM: Homo sapiens

<400> SEQUENCE: 16
ccagtgtggc cttgttggct tgaag                            25

<210> SEQ ID NO 17
<211> LENGTH: 44
<212> TYPE: DNA
<213> ORGANISM: Homo sapiens

<400> SEQUENCE: 17
ctctccctgt ctccgggtaa gctagcgcga cggccggcaa gccc       44

<210> SEQ ID NO 18
<211> LENGTH: 54
<212> TYPE: DNA
<213> ORGANISM: Homo sapiens

<400> SEQUENCE: 18
aaagctagcg gactacaagg acgacgatga caagtgagtg cgacggccgg caag    54

<210> SEQ ID NO 19
<211> LENGTH: 327
<212> TYPE: PRT
<213> ORGANISM: Homo sapiens

<400> SEQUENCE: 19

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

-continued

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 20
<211> LENGTH: 315
<212> TYPE: PRT
<213> ORGANISM: Homo sapiens

<400> SEQUENCE: 20

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Ala Pro Glu Phe Leu Gly Gly Pro Ser Val Phe Leu Phe Pro
            100                 105                 110

Pro Lys Pro Lys Asp Thr Leu Met Ile Ser Arg Thr Pro Glu Val Thr

```
                115                 120                 125
        Cys Val Val Asp Val Ser Gln Glu Asp Pro Glu Val Gln Phe Asn
        130                 135                 140

Trp Tyr Val Asp Gly Val Glu Val His Asn Ala Lys Thr Lys Pro Arg
        145                 150                 155                 160

Glu Glu Gln Phe Asn Ser Thr Tyr Arg Val Val Ser Val Leu Thr Val
                        165                 170                 175

Leu His Gln Asp Trp Leu Asn Gly Lys Glu Tyr Lys Cys Lys Val Ser
                    180                 185                 190

Asn Lys Gly Leu Pro Ser Ser Ile Glu Lys Thr Ile Ser Lys Ala Lys
                195                 200                 205

Gly Gln Pro Arg Glu Pro Gln Val Tyr Thr Leu Pro Pro Ser Gln Glu
        210                 215                 220

Glu Met Thr Lys Asn Gln Val Ser Leu Thr Cys Leu Val Lys Gly Phe
        225                 230                 235                 240

Tyr Pro Ser Asp Ile Ala Val Glu Trp Glu Ser Asn Gly Gln Pro Glu
                        245                 250                 255

Asn Asn Tyr Lys Thr Thr Pro Pro Val Leu Asp Ser Asp Gly Ser Phe
                    260                 265                 270

Phe Leu Tyr Ser Arg Leu Thr Val Asp Lys Ser Arg Trp Gln Glu Gly
                275                 280                 285

Asn Val Phe Ser Cys Ser Val Met His Glu Ala Leu His Asn His Tyr
        290                 295                 300

Thr Gln Lys Ser Leu Ser Leu Ser Leu Gly Lys
        305                 310                 315

<210> SEQ ID NO 21
<211> LENGTH: 23
<212> TYPE: DNA
<213> ORGANISM: Homo sapiens

<400> SEQUENCE: 21
tgtactttgg cctctctggg ata                                            23

<210> SEQ ID NO 22
<211> LENGTH: 29
<212> TYPE: DNA
<213> ORGANISM: Homo sapiens

<400> SEQUENCE: 22
ctggagatta aacgtacggt ggctgcacc                                      29

<210> SEQ ID NO 23
<211> LENGTH: 45
<212> TYPE: DNA
<213> ORGANISM: Homo sapiens

<400> SEQUENCE: 23
gcgactaagc ttgccgccac catggaagcc ccagctcagc ttctc                    45

<210> SEQ ID NO 24
<211> LENGTH: 44
<212> TYPE: DNA
<213> ORGANISM: Homo sapiens

<400> SEQUENCE: 24
gctgaaagct tgccgccacc atggagttgg gactgagctg gatt                     44
```

```
<210> SEQ ID NO 25
<211> LENGTH: 23
<212> TYPE: DNA
<213> ORGANISM: Homo sapiens

<400> SEQUENCE: 25
gtagtctgag cagtactcgt tgc                                            23

<210> SEQ ID NO 26
<211> LENGTH: 23
<212> TYPE: DNA
<213> ORGANISM: Homo sapiens

<400> SEQUENCE: 26
gaagacttaa ggcagcggca gaa                                            23

<210> SEQ ID NO 27
<211> LENGTH: 23
<212> TYPE: DNA
<213> ORGANISM: Homo sapiens

<400> SEQUENCE: 27
ggtcagggcg cctgagttcc acg                                            23

<210> SEQ ID NO 28
<211> LENGTH: 23
<212> TYPE: DNA
<213> ORGANISM: Homo sapiens

<400> SEQUENCE: 28
atgcaggcta ctctagggca cct                                            23

<210> SEQ ID NO 29
<211> LENGTH: 36
<212> TYPE: DNA
<213> ORGANISM: Homo sapiens

<400> SEQUENCE: 29
gaagaccgat gggcccttgg tgctagctga ggagac                              36

<210> SEQ ID NO 30
<211> LENGTH: 32
<212> TYPE: DNA
<213> ORGANISM: Homo sapiens

<400> SEQUENCE: 30
tgagaattcg gtgggtgctt tatttccatg ct                                  32

<210> SEQ ID NO 31
<211> LENGTH: 33
<212> TYPE: DNA
<213> ORGANISM: Homo sapiens

<400> SEQUENCE: 31
gtagaagctt accatcgcgg atagacaaga acc                                 33

<210> SEQ ID NO 32
<211> LENGTH: 33
<212> TYPE: DNA
<213> ORGANISM: Homo sapiens

<400> SEQUENCE: 32
ggtcccccat gcccaccatg cccgggtaag cca                                 33
```

<210> SEQ ID NO 33
<211> LENGTH: 33
<212> TYPE: DNA
<213> ORGANISM: Homo sapiens

<400> SEQUENCE: 33
tggcttaccc gggcatggtg ggcatggggg acc               33

USE OF EFFECTOR-FUNCTION-DEFICIENT ANTIBODIES FOR TREATMENT OF AUTO-IMMUNE DISEASES

FIELD OF THE INVENTION

The present invention relates to the treatment of autoimmune diseases and disorders by administration of antibodies.

BACKGROUND OF THE INVENTION

Myasthenia gravis (MG) is a chronic autoimmune neuromuscular disease characterized by varying degrees of weakness of the skeletal muscles of the body. The most common cause of MG is the presence of auto-antibodies against the nicotinic acetylcholine receptor (AChR) of the muscle.

AChR is a pentameric, transmembrane protein composed of five subunits in a stoichiometry of $\alpha 2$, $\beta$, $\gamma$, and $\delta$. In adults, the receptor $\gamma$ subunit is replaced by the $\epsilon$-subunit. AChR are located at high density in the postsynaptic membrane of the neuromuscular junction (NMJ). After binding of acetylcholine (ACh), released by the nerve terminal, AChR facilitate the depolarisation of the postsynaptic membrane, leading to the contraction of muscle fibers. Anti-AChR antibodies induce a loss of AChR, leading to an impaired neuromuscular transmission. This results in fluctuating skeletal muscle weakness that worsens with use, and improves with rest. If the concentration of AChR is very low, the effects can also be measured by electrophysiology, showing a decrementing response of the compound muscle action potential (CMAP) after repetitive nerve stimulation.

Anti-AChR antibodies of all IgG subclasses have been found in MG patients, but the only isotype that is always present is IgG1 (Rodgaard, A. et al., Clin Exp Immunol 67, 82 (1987)). Pathogenic mechanisms include: damage of the NMJ by focal lysis of the postsynaptic membrane due to complement activation, cross-linking of AChRs, which leads to increased internalization and degradation of the receptors (antigenic modulation) (Heinemann, S. et al., Proc Natl Acad Sci USA 74, 3090 (1977)) and Kao, I. et al., Science 196, 527 (1977), inhibition of or ion channel function (Lang, B. et al., J Neuroimmunol 19, 141 (1988)) and blocking of the ACh binding site (Almon, R R. et al., Science 186, 55 (1974)). The extracellular domain of the $\alpha$ subunits contains the main immunogenic region (MIR), to which a major part of the pathogenic MG antibodies is directed (Tzartos, S J et al., Proc Natl Acad Sci USA 77, 755 (1980), Tzartos, S J et al., Proc Natl Acad Sci USA 79, 188 (1982) and Tzartos, S J. et al., Immunol Rev 163, 89 (1998). Anti-MIR antibodies are also very effective in antigenic modulation.

The effects of auto-antibodies directed to the proteins of the NMJ can be studied in an animal model of MG, termed experimental autoimmune myasthenia gravis (EAMG). The original experimental model, which led to the discovery of the cause of MG, is the immunization of rabbits with the AChR from the electric organ of *Electrophorus electricus* which induced a chronic EAMG (Patrick, J. et al., Science 180, 871 (1973). Subsequently, the similarity to human MG was demonstrated by immunising rhesus monkeys (*Macaca mulatta*) with repeated doses of *Torpedo californica* AChR (Tarrab-Hazdai, R. et al., Nature 256, 128 (1975)). Electromyography showed a decreased action potential after repetitive nerve stimulation, confirming impaired neuromuscular transmission. In a rodent chronic EAMG model, a sub-population of antibodies against the *Torpedo* or *Electrophorus* AChR that cross-react with the AChR of the immunised animal were identified as the cause of the damage to the NMJ, leading to a long-lasting disease (Lindstrom, J M. et al., Ann NY Acad Sci 274, 254 (1976). Sera from MG patients, AChR-immunised animals and monoclonal anti-AChR antibodies have also been shown to induce MG symptoms when injected in naïve animals (passive transfer EAMG) (Toyka, K V et al., Science 190, 397 (1975), Toyka, K V et al., N Engl J Med 296, 125 (1977) and Lindstrom, J M et al., J Exp Med 144, 739 (1976)). Passive transfer causes a reversible muscular weakness that lasts for several days.

Several specific immunotherapy approaches have been tested in EAMG models, including anti-idiotypic Abs, mAb-competing peptide, tolerance induction, and elimination of AChR-specific T cells by genetically engineered antigen-presenting cells (Souroujon, M C et al., Neurology 36, 622 (1986), Verschuuren, J J et al., J Immunol 146, 941 (1991), Luo, G X et al., J Immunol Methods 251, 177 (2001), Wang, Z Y et al., J Neuroimmunol 44, 209 (1993), Im, S H et al., Faseb J 15, 2140 (2001), Wu, J M et al., Cell Immunol 208, 137 (2001)). None of these approaches have lead to an efficient MG therapy so far.

An alternative approach is the direct blocking of the auto-antibody binding sites of the AChR. This approach is feasible since a large fraction of the circulating autoantibodies in MG patients is directed against the MIR. It has been shown that a patient derived anti-AChR Fab-637 is capable of blocking the binding of serum derived polyclonal anti-AChR antibody derived from various unrelated MG patients to human AChR in vitro (Graus, Y F et al., J Immunol 158, 1919 (1997)). As anti-MIR Fab fragments do not have intrinsic properties to induce loss of functional AChR, since they do not activate complement, induce antigenic modulation or functionally inhibit the AChR, anti-MIR Fab fragments have been successfully used to prevent passive transfer of EAMG in rats and mice (Loutrari, H. et al., Eur J Immunol 22, 2449 (1992), Toyka, K V. et al., J Neurol Neurosurg Psychiatry 43, 836 (1980) and Papanastasiou, D K et al., J Neuroimmunol 104, 124 (2000). Human anti-human AChR Fab fragments have been cloned and their ability to block MG serum Abs explored (Rey, E. et al., Clin Immunol 96, 269 (2000), Farrar, J. et al., Int Immunol 9, 1311 (1997), Protopapadakis, E. et al., Eur J Immunol 35, 1960 (2005) and Stassen, M H et al., J Neuroimmunol 135, 56 (2003). However, no further in vivo proof of concept was obtained and Fab molecules are unsuitable for treatment of patients, inter alia due to their short half-life.

In general, five methods of treatment are currently used in MG (Sieb, J P, Curr Opin Pharmacol 5, 303 (2005): 1) Enhancement of neuromuscular transmission using acetylcholinesterase (AChE) inhibitors, such as neostigmine and pyridostigmine, prolonging the action of acetyl choline, which helps improve neuromuscular transmission and increase muscle strength, 2) immunosuppression, using drugs such as prednisone, cyclosporine, and azathioprine, aiming to suppress the production of auto-antibodies, 3) thymectomy, 4) elimination of auto-antibodies by plasma exchange, and 5) modulation of the autoimmune response by intravenous immunoglobulins.

However, none of these methods of treatment is very efficacious or specific and thus, there is a need for improved methods for treating myasthenia gravis and other auto-immune diseases.

SUMMARY OF THE INVENTION

The present invention provides the use of an effector-function-deficient antibody for the preparation of a pharmaceutical composition for treatment of an antibody-mediated autoimmune disease or disorder in a subject, wherein said effector-function-deficient antibody is capable of competing with one or more of the auto-antibodies involved in mediating the antibody-mediated auto-immune disease or disorder for binding to a target auto-antigen, and wherein said effector-function-deficient antibody is a multivalent antibody.

In one embodiment, said effector-function-deficient antibody is of the IgG4 isotype. IgG4 has a half life similar to IgG1 and is deficient in effector-functions, such as complement activation and Fc receptor binding.

Specifically, the present invention discloses the use of an IgG4 variant based on a patient derived Fab (IgG4-637) for prevention of the pathogenic effect of anti-AChR antibodies. In contrast to an IgG1 full antibody 637 that is able to induce signs of MG in rhesus monkeys, IgG4-637 does not induce any signs of experimental MG. Surprisingly, it was observed that IgG4-637 is capable of blocking the pathogenic effects of IgG1-637 when administered simultaneously in excess to the IgG1-637, even though the IgG4-637 that was injected in the monkeys was capable of cross-linking AChRs in vitro. This has been described in Examples 1 to 7 herein.

Without being bound by any specific theory, the results described in Example 8 herein suggest that IgG4-637 may exchange with monkey immunoglobulins in vivo, resulting in a modified molecule which only binds monovalently to AChR and therefore has lost the ability of cross-linking AChRs. Without being bound by any specific theory, this could suggest that monovalent antibodies may also be used for the treatment of antibody-mediated auto-immune diseases provided inter alia that an acceptable pharmacokinetic profile can be obtained. As demonstrated in Examples 9 to 16, monovalent antibodies that are modified in the hinge region fulfil this criterion.

Thus, in a related aspect, the invention provides the use of an effector-function-deficient antibody for the preparation of a pharmaceutical composition for treatment of an antibody-mediated auto-immune disease or disorder in a subject, wherein said effector-function-deficient antibody is capable of competing with one or more of the auto-antibodies involved in mediating the antibody-mediated auto-immune disease or disorder for binding to a target auto-antigen, and wherein said effector-function-deficient antibody is a monovalent antibody comprising a light chain and a heavy chain, wherein
a) said light chain comprises the amino acid sequence of the variable ($V_L$) region of a selected antigen specific antibody and the amino acid sequence of the constant ($C_L$) region of an Ig, and wherein, in case of an IgG1 subtype, the amino sequence of the constant ($C_L$) region has been modified so that it does not contain any amino acids capable of participating in the formation of disulfide bonds or covalent bonds with other peptides comprising an identical amino acid sequence of the constant ($C_L$) region of the Ig, and
b) said heavy chain comprises the amino acid sequence of the variable ($V_H$) region of said selected antigen specific antibody and the amino acid sequence of the constant ($C_H$) region of human Ig, wherein the amino acid sequence of the constant ($C_H$) region has been modified so that the hinge region and, as required by the Ig subtype, other regions of the $C_H$ region, such as the $C_H3$ region, does not contain any amino acid residues which participate in the formation of disulphide bonds or covalent or non-covalent inter-heavy chain bonds with other peptides comprising an identical amino acid sequence of the constant ($C_H$) region of the human Ig.

BRIEF DESCRIPTION OF THE FIGURES

FIG. 1: Primer details.

FIG. 9: Compound muscle action potentials (CMAP) of the extensor digitorum brevis muscle during RNS of the peroneal nerve (A, B, C: 3 Hz stimulation; D, E, F: 5 Hz stimulation). (A, D) CMAP in an animal that received 5 mg/kg IgG1 637. (B, E) CMAP in an animal that received 15 mg/kg IgG4-637. (C, F) CMAP in an animal that received 15 mg/kg IgG4-637 and 5 mg/kg IgG1-637.

FIG. 11: Analysis of compound muscle action potentials from rhesus monkeys as described in Example 7.

FIG. 12: In vivo competition of IgG4-637 with IgG1-637.

FIG. 13: Antigenic modulation of surface AChR of TE671 cells by serum from IgG1-637 and/or IgG4-637 treated monkeys. (A) AChR loss by means of antigenic modulation was determined on TE671 cells by the addition of monkey sera taken at different time points after start of antibody treatment. Monkeys were injected with the respective antibodies on day 0, 1 and 2. Confluent TE671 cells were treated with cycloheximide and sera, diluted to a final concentration of 637 antibody concentration of 0.1 nM. (B) Protection from antigenic modulation was studied by treating TE671 cells with 1 nM IgG1 637 and monkey sera, diluted to a final concentration of 637 antibody concentration of 10, 1 or 0.1 nM.

BRIEF DESCRIPTION OF SEQUENCE LISTING

Figure 2:
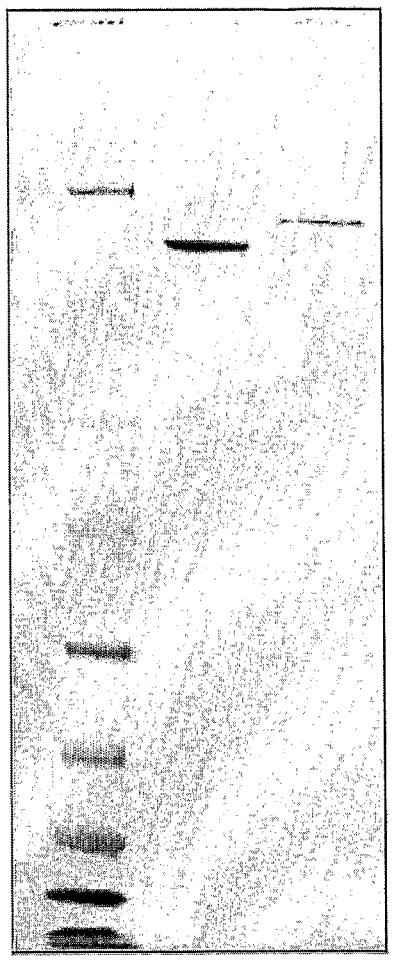
FIG. 2: The IgG4-637 antibody was evaluated on non-reducing SDS-PAGE. Lane 1: Marker SeuBlue plus2 prestained (Invitrogen BV, The Netherlands), Lane 2: internal control, lane 3: IgG4-637.

SEQ ID No: 1 shows the nucleic acid sequence of the $V_H$ region of IgG4-637.
SEQ ID No: 2 shows the amino acid sequence of the $V_H$ region of IgG4-637.
SEQ ID No: 3 shows the nucleic acid sequence of the $V_L$ region of IgG4-637.
SEQ ID No: 4 shows the amino acid sequence of the $V_L$ region of IgG4-637.
SEQ ID No: 5 shows the nucleic acid sequence of the $C_H$ region of IgG4-637.
SEQ ID No: 6 shows the amino acid sequence of the $C_H$ region of IgG4-637.
SEQ ID No: 7 shows the nucleic acid sequence of the constant λ chain of region of IgG4-637.
SEQ ID No: 8 shows the amino acid sequence of the constant λ chain of region of IgG4-637.
SEQ ID No: 9 to 18 and 21 to 33 show the nucleic acid sequences of oligonucleotides used as primers in recombinant DNA techniques.
SEQ ID No: 19: The amino acid sequence of the wildtype $C_H$ region of human IgG4.
SEQ ID No: 20: The amino acid sequence of the hingeless $C_H$ region of a human IgG4.

DETAILED DESCRIPTION OF THE INVENTION

The present invention provides a use of an effector-function-deficient antibody for the preparation of a pharmaceutical composition for treatment of an antibody-mediated auto-immune disease or disorder in a subject, wherein said effector-function-deficient antibody is capable of competing with one or more of the auto-antibodies involved in mediating the antibody-mediated auto-immune disease or disorder for binding to a target auto-antigen, and wherein said effector-function-deficient antibody is:

a multivalent antibody; or a monovalent antibody comprising a light chain and a heavy chain, wherein a) said light chain comprises the amino acid sequence of the variable ($V_L$) region of a selected antigen specific antibody and the amino acid sequence of the constant ($C_L$) region of an Ig, and wherein, in case of an IgG1 subtype, the amino sequence of the constant ($C_L$) region has been modified so that it does not contain any amino acids capable of participating in the formation of disulfide bonds or covalent bonds with other peptides comprising an identical amino acid sequence of the constant ($C_L$) region of the Ig, and b) said heavy chain comprises the amino acid sequence of the variable ($V_H$) region of said selected antigen specific antibody and the amino acid sequence of the constant ($C_H$) region of human Ig, wherein the amino acid sequence of the constant ($C_H$) region has been modified so that the hinge region and, as required by the Ig subtype, other regions of the $C_H$ region, such as the $C_H3$ region, does not contain any amino acid residues which participate in the formation of disulphide bonds or covalent or non-covalent inter-heavy chain bonds with other peptides comprising an identical amino acid sequence of the constant ($C_H$) region of the human Ig.

The present invention also provides a method for treatment of an antibody-mediated auto-immune disease or disorder, which method comprises administration of an effector-function-deficient antibody to a subject in need thereof, wherein said effector-function-deficient antibody is capable of competing with one or more of the auto-antibodies involved in mediating the antibody-mediated auto-immune disease or disorder for binding to a target auto-antigen, and wherein said effector-function-deficient antibody is:

a multivalent antibody; or a monovalent antibody comprising a light chain and a heavy chain, wherein a) said light chain comprises the amino acid sequence of the variable ($V_L$) region of a selected antigen specific antibody and the amino acid sequence of the constant ($C_L$) region of an Ig, and wherein, in case of an IgG1 subtype, the amino sequence of the constant ($C_L$) region has been modified so that it does not contain any amino acids capable of participating in the formation of disulfide bonds or covalent bonds with other peptides comprising an identical amino acid sequence of the constant ($C_L$) region of the Ig, and b) said heavy chain comprises the amino acid sequence of the variable ($V_H$) region of said selected antigen specific antibody and the amino acid sequence of the constant ($C_H$) region of human Ig, wherein the amino acid sequence of the constant ($C_H$) region has been modified so that the hinge region and, as required by the Ig subtype, other regions of the $C_H$ region, such as the $C_H3$ region, does not contain any amino acid residues which participate in the formation of disulphide bonds or covalent or non-covalent inter-heavy chain bonds with other peptides comprising an identical amino acid sequence of the constant ($C_H$) region of the human Ig.

The present invention also provides an effector-function-deficient antibody, which is capable of competing with one or more auto-antibodies involved in mediating an antibody-mediated auto-immune disease or disorder for binding to a target auto-antigen, wherein said effector-function-deficient antibody is:

a multivalent antibody; or a monovalent antibody comprising a light chain and a heavy chain, wherein a) said light chain comprises the amino acid sequence of the variable ($V_L$) region of a selected antigen specific antibody and the amino acid sequence of the constant ($C_L$) region of an Ig, and wherein, in case of an IgG1 subtype, the amino sequence of the constant ($C_L$) region has been modified so that it does not contain any amino acids capable of participating in the formation of disulfide bonds or covalent bonds with other peptides comprising an identical amino acid sequence of the constant ($C_L$) region of the Ig, and b) said heavy chain comprises the amino acid sequence of the variable ($V_H$) region of said selected antigen specific antibody and the amino acid sequence of the constant ($C_H$) region of human Ig, wherein the amino acid sequence of the constant ($C_H$) region has been modified so that the hinge region and, as required by the Ig subtype, other regions of the $C_H$ region, such as the $C_H3$ region, does not contain any amino acid residues which participate in the formation of disulphide bonds or covalent or non-covalent inter-heavy chain bonds with other peptides comprising an identical amino acid sequence of the constant ($C_H$) region of the human Ig.

The term antibody in the context of the present invention refers to an immunoglobulin molecule, a fragment of an immunoglobulin molecule, or a derivative of either thereof, which has the ability to specifically bind to an antigen under typical physiological conditions with a half life of significant periods of time such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen).

The term immunoglobulin refers to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$) and a heavy chain constant region. The heavy chain constant region typically is comprised of three domains, $C_H1$, $C_H2$, and $C_H3$. Each light chain typically is comprised of a light chain variable region (abbreviated herein as $V_L$) and a light chain constant region. The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs).

Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Typically, the numbering of amino acid residues in this region is performed by the method described in Kabat et al., Sequences of Proteins of Immunological Interest, 5th Ed. Public Health Service, National Institutes of Health, Bethesda, Md. (1991) (phrases such as variable domain residue numbering as in Kabat or according to Kabat herein refer to this numbering system for heavy chain variable domains or light chain variable domains). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of $V_H$ CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The variable regions of the heavy and light chains of the immunoglobulin molecule contain a binding domain that interacts with an antigen. The constant regions of the immunoglobulin molecules have different functions, and may thus for instance mediate the binding of the immunoglobulin to host tissues or factors, including various cells of the immune system (such as effector cells) and the first component (C1q) of the classical complement system or to for instance the neonatal Fc receptor (FcRn) which protects IgG from intracellular degradation following endocytosis.

As indicated above, the term antibody herein, unless otherwise stated or clearly contradicted by context, includes fragments of an antibody that retain the ability to specifically bind to an antigen. It has been shown that the antigen-binding function of an antibody may be performed by fragments of a full-length antibody. Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Other forms of single chain antibodies, such as diabodies are included within the term antibody. Although such fragments are generally included within the meaning of antibody, they collectively and each independently are unique features of the present invention, exhibiting different biological properties and utility. These and other useful antibody fragments in the context of the present invention are discussed further herein.

It also should be understood that the term antibody also generally, unless otherwise stated or clearly contradicted by context, includes polyclonal antibodies, monoclonal antibodies (mAbs), antibody-like polypeptides, such as chimeric antibodies and humanized antibodies, anti-idiotypic (anti-Id)

antibodies to antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

In one embodiment, the effector-function-deficient antibody is a polyclonal antibody, for instance in form of an antibody cocktail of different IgG4 antibodies or other effector-function-deficient antibodies.

In one embodiment, the effector-function-deficient antibody is a monoclonal antibody. The term "monoclonal antibody" as used herein refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal nonhuman animal, such as a transgenic mouse, having a genome comprising a human heavy chain transgene and a light chain transgene, fused to an immortalized cell.

In a further embodiment, the effector-function-deficient antibody is a human monoclonal antibody. In another further embodiment, the effector-function-deficient antibody is a humanized antibody. In another further embodiment, the effector-function-deficient antibody is a chimeric antibody. In another further embodiment, the effector-function-deficient antibody is a monoclonal antibody originating entirely from a mammalian species different from humans. In a further embodiment, the effector-function-deficient antibody is a fully murine monoclonal antibody.

A monoclonal antibody refers to a composition comprising a homogeneous antibody population having a uniform structure and specificity. Typically a monoclonal antibody is an antibody obtained from a population of substantially homogeneous antibodies, i.e., the individual antibodies comprised within the population are identical except for possible naturally occurring mutations that may be present in minor amounts. Monoclonal antibodies are highly specific and each monoclonal antibody is typically directed against a single epitope, which is in contrast to polyclonal antibody preparations which typically include different antibodies directed against different epitopes. That an antibody is monoclonal is not to be construed as requiring production of the antibody by any particular method. For example, the monoclonal antibodies of the present invention may be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991).

Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

In one embodiment, the effector-function-deficient antibody is a human antibody.

The term "human antibody", as used herein, is intended to include antibodies having variable and constant regions derived from human germline immunoglobulin sequences. The human antibodies of the present invention may include amino acid residues not encoded by human germline immunoglobulin sequences (for instance mutations introduced by random or site-specific mutagenesis in vitro or by somatic mutation in vivo).

As used herein, a human antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germlne immunoglobulin gene. Typically, outside the heavy chain CDR3 region, a human antibody derived from a particular human germlne sequence will display no more than 10 amino acid differences, such as no more than 5, for instance no more than 4, 3, 2, or 1 amino acid difference from the amino acid sequence encoded by the germline immunoglobulin gene.

Human monoclonal antibodies suitable for use in the present invention may be generated using transgenic or transchromosomal mice carrying parts of the human immune system rather than the mouse system. Such transgenic and transchromosomic mice include mice may be referred to as HuMAb mice and KM mice, respectively, and are collectively referred to herein as "transgenic mice".

The HuMAb mouse contains a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al., Nature 368, 856-859 (1994)). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci 764 536-546 (1995)). The preparati of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat No. 5,545,806, U.S. Pat. No. 5,569, 825, U.S. Pat. No. 5,625,126, U.S. Pat. No. 5,633,425, U.S. Pat. No. 5,789,650, U.S. Pat. No. 5,877,397, U.S. Pat. No. 5,661,016, U.S. Pat. No. 5,814,318, U.S. Pat. No. 5,874,299, U.S. Pat. No. 5,770,429, U.S. Pat. No. 5,545,807, WO 98/24884, WO 94/25585, WO 93/1227, WO 92/22645, WO 92/03918 and WO 01/09187.

The HCo7 mice have a JKD disruption in their endogenous light chain (κ) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo7 human heavy chain transgene (as described in U.S. Pat. No. 5,770,429). The HCo12 mice have a JKD disruption in their endogenous light chain (kappa)

genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo12 human heavy chain transgene (as described in Example 2 of WO 01/14424). In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human κ light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478. The KM mouse contains a human heavy chain transchromosome and a human kappa light chain transgene. The endogenous mouse heavy and light chain genes also have been disrupted in the KM mice such that immunization of the mice leads to production of human immunoglobulins rather than mouse immunoglobulins. Construction of KM mice and their use to raise human immunoglobulins is described in detail in WO 02/43478.

Splenocytes from these transgenic mice may be used to generate hybridomas that secrete human monoclonal antibodies according to well known techniques. Such transgenic mammals, mammals comprising an operable nucleic acid sequence coding for expression of an antibody suitable for use in the present invention, mammals stably transfected with one or more such nucleic acid sequences, and the like, are additional features of the present invention.

Antibodies suitable for use according to the present invention may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. No. 5,827,690, U.S. Pat. No. 5,756,687, U.S. Pat. No. 5,750,172 and U.S. Pat. No. 5,741,957.

Further, human antibodies of the present invention or antibodies of the present invention from other species may be generated through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hoganboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized, for instance as described elsewhere herein.

In one embodiment, the antibody suitable for use according to the present invention is a "recombinant human antibody", as used herein, includes all human antibodies that are prepared, expressed, created or isolated by recombinant means, such as (a) antibodies isolated from an animal (such as a mouse) that is transgenic or trans-chromosomal for human immunoglobulin genes or a hybridoma prepared therefrom (described further elsewhere herein), (b) antibodies isolated from a host cell transformed to express the antibody, such as from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies may be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

A humanized antibody is an antibody that is derived from a non-human species, in which certain amino acids in the framework and constant domains of the heavy and light chains have been mutated so as to avoid or abrogate an immune response in humans. Humanized forms of non-human (for instance murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. A humanized antibody optionally also will comprise at least a portion of an immunoglobulin constant region (Fc), typically that of a human immunoglobulin. For further details, see Jones et al., Nature 321, 522-525 (1986), Riechmann et al., Nature 332, 323-329 (1988) and Presta, Curr. Op. Struct. Biol. 2, 593-596 (1992). Humanized monoclonal antibodies suitable for use according to the present invention may be generated by fusing the constant domains from a human antibody to the variable domains of a non-human species. Examples of how to make humanized antibodies may be found in for instance U.S. Pat. No. 6,054,297, U.S. Pat. No. 5,886,152 and U.S. Pat. No. 5,877,293. A humanized antibody is designed to have greater homology to a human immunoglobulin than animal-derived monoclonal antibodies. Non-human amino acid residues from an "import" (animal) variable domain typically are transfected into a human "backbone". Humanization may essentially be performed following the method of Winter and co-workers (Jones et al., Nature 321, 522-525 (1986), Riechmann et al., Nature 332, 323-327 (1988), Verhoeyen et al., Science 239, 1534-1536 (1988)), by substituting rodent complementarity determining regions ("CDRs") or CDR sequences for the corresponding sequences of a human antibody.

The term "chimeric antibody" refers to an antibody that contains one or more regions from one antibody and one or more regions from one or more other antibodies. A bivalent chimeric antibody is tetramer ($H_2L_2$) formed by two HL dimers associated through at least one disulfide bridge. Typically, a chimeric antibody refers to an antibody in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see for instance U.S. Pat. No. 4,816,567 and Morrison et al., PNAS USA 81, 6851-6855 (1984)). Chimeric antibodies are produced by recombinant processes well known in the art (see for instance Cabilly et al., PNAS USA 81, 3273-3277 (1984), Morrison et al., PNAS USA 81, 6851-6855 (1984), Boulianne et al., Nature 312, 643-646 (1984), EP125023, Neuberger et al., Nature 314, 268-270 (1985), EP171496, EP173494, WO86/01533, EP184187, Sahagan et al., J. Immunol. 137, 1066-1074 (1986), WO87/02671, Liu et al., PNAS USA 84, 3439-3443 (1987), Sun et al., PNAS USA 84, 214-218 (1987), Better et al., Science 240, 1041-1043 (1988) and Harlow et al., Antibodies: A Laboratory Manual, Cold Spring Harbor Laboratory Press, Cold Spring Harbor, N. Y., (1988)). Also, the use of Ig cDNA for construction of chimeric immunoglobulin genes is known in the art (see for instance Liu et al., PNAS USA 84, 3439 (1987) and J. Immunol. 139, 3521 (1987)). mRNA is isolated from a hybridoma or other cell producing the antibody and used to produce cDNA: The cDNA of interest may be amplified by the polymerase chain reaction using specific primers (U.S. Pat. No. 4,683,195 and U.S. Pat. No. 4,683,202). Alternatively, a library is made and screened to isolate the sequence of interest. The DNA sequence encoding the variable region of the antibody is then fused to human constant region sequences. Sequences of human constant regions (as well as variable regions) may be found in Kabat et al., (1991) Sequences of Proteins of Immunological Interest, N.I.H. publication no. 91-3242 and more recent and related data may be accessed at http://www.biochem.ucl.ac.uk/~martin/abs/GeneralInfo.html. The choice of isotype typically will be guided by the desired effector functions, such as complement fixation, or activity in antibody-dependent cellular cytotoxicity. Exemplary isotypes are IgG1, IgG2, IgG3, and IgG4. Either of the human light chain constant regions, kappa or lambda, may be used. The chimeric, humanized antibody may then be expressed by conventional methods.

Antibodies suitable for use according to the present invention may be recovered from or derived from antibodies recovered from recombinant combinatorial antibody libraries, such as a scFv phage display library, which may be made with human $V_L$ and $V_H$ cDNAs prepared from mRNA derived from human lymphocytes. Methods for preparing and screening such libraries are known in the art. There are a number of commercially available kits for generating phage display libraries. There are also other methods and reagents that may be used in generating and screening antibody display libraries (see for instance U.S. Pat. No. 5,223,409, WO 92/18619, WO 91/17271, WO 92/20791, WO 92/15679, WO 93/01288, WO 92/01047, WO 92/09690, Fuchs et al., Bio/Technology 9, 1370-1372 (1991), Hay et al., Hum. Antibod. Hybridomas 3, 81-85 (1992), Huse et al., Science 246, 1275-1281 (1989), McCafferty et al., Nature 348, 552-554 (1990), Griffiths et al., EMBO J 12, 725-734 (1993), Hawkins et al., J. Mol. Biol. 226, 889-896 (1992), Clackson et al., Nature 352, 624-628 (1991), Gram et al., PNAS USA 89, 3576-3580 (1992), Garrad et al., Bio/Technology 9, 1373-1377 (1991), Hoogenboom et al., Nuc Acid Res 19, 4133-4137 (1991) and Barbas et al., PNAS USA 88, 7978-7982 (1991)). Suitable $V_L$ and $V_H$ nucleic acid sequences may be selected using any appropriate method. For example, $V_L$ and $V_H$ nucleic acids may be selected by employing the epitope imprinting methods described in WO 93/06213. Antibody libraries, such as scFv libraries may be prepared and screened using known and suitable methods, such as those described in for instance WO92/01047, McCafferty et al., Nature 348, 552-554 (1990) and Griffiths et al., EMBO J 12, 725-734 (1993).

To further improve the quality and/or diversity of antibodies suitable for use according to the present invention, the $V_L$ and $V_H$ segments of $V_L/V_H$ pair(s) may be randomly mutated, for instance within the CDR3 region of $V_H$ and/or $V_L$, in a process analogous to the in vivo somatic mutation process responsible for affinity maturation of antibodies during a natural immune response. This in vitro affinity maturation may be accomplished by amplifying $V_H$ and $V_L$ regions using PCR primers complimentary to the $V_H$ CDR3 or $V_L$ CDR3, respectively, which primers typically are "spiked" with a random mixture of the four nucleotide bases at certain positions, such that the resultant PCR products encode $V_H$ and $V_L$ segments into which random mutations have been introduced into the $V_H$ and/or $V_L$ CDR3 regions. These randomly mutated $V_H$ and $V_L$ segments may be re-screened for binding to the target auto-antigen in question.

Following screening, nucleic acid encoding a selected antibody may be recovered from the display package (e.g., from the phage genome) and subcloned into an appropriate vector by standard recombinant DNA techniques. To express a recombinant antibody isolated by screening of a combinatorial library, typically a nucleic acid comprising a sequence encoding the antibody is cloned into a recombinant expression vector and introduced into appropriate host cells (mammalian cells, yeast cells, etc.) under conditions suitable for expression of the nucleic acid and production of the antibody.

High-affinity antibody peptides, such as human single-chain Fv (scFv) and Fab antibody fragments, may also be isolated from such libraries using a panning technique in which the antigen of interest is immobilized on a solid surface, such as microtiter plates or beads (see for instance Barbas and Burton, Trends. Biotechnol. 14, 230-234 (1996) and Aujame et al., Hum. Antibodies 8, 155-68 (1997). Phage display of large naive libraries also makes it possible to isolate human antibodies directly without immunization (see for instance de Haard et al., J. Biol. Chem. 274(26), 18218-18230 (1999)).

Antibodies suitable for use according to the present invention may also be variant antibodies. A "variant" antibody is an antibody that differs from a parent antibody by one or more suitable amino acid residue alterations, that is substitutions, deletions, insertions, or terminal sequence additions, in the CDRs or other $V_H$ and/or $V_L$ sequences (provided that at least a substantial amount of the epitope binding characteristics of the parent antibody are retained, if not improved upon, by such changes).

Variations in an antibody variant may be made in each of the framework regions, the constant domain, and/or the variable regions (or any one or more CDRs thereof in a single variant antibody. Alternatively, variations may be made in only one of the framework regions, the variable regions (or single CDR thereof, or the constant domain in an antibody. Alanine scanning mutagenesis techniques, such as described by Cunningham and Wells, Science 244, 1081-1085 (1989), may be used to identify suitable residues for substitution or deletion in generating antibodies suitable for use according to the present invention comprising variant $V_L$, $V_H$, or particular CDR sequences, although other suitable mutagenesis techniques also may be applied. Multiple amino acid substitutions may also be made and tested using known methods of mutagenesis and screening, such as those disclosed by Reidhaar-Olson and Sauer, Science 241, 53-57 (1988) or Bowie and Sauer, PNAS USA 86, 2152-2156 (1989).

Thus, for example, in an antibody variant one or more amino acid residues may be introduced or inserted in or adjacent to one or more of the hypervariable regions of a parent antibody, such as in one or more CDRs. A variant of an antibody suitable for use according to the present invention may comprise any number of inserted amino acid residues, provided again that at least a substantial amount of the epitope binding characteristics of the parent antibody are retained. Such antibody variant may for example comprise from about 1-30 inserted amino acid residues, for instance from about 1-10, such as for instance from about 2-10, for instance from 2-5 or such as from about 1-5 inserted amino acid residues. Likewise, such antibody variant may for example comprise from about 1-30 deleted amino acid residues, for instance from about 1 -10, such as for instance from about 2-10, for instance from 2-5 or such as from about 1-5 deleted amino acid residues. Likewise, such antibody variant may for example comprise from about 1-30 substituted amino acid residues, for instance from about 1-10, such as for instance from about 2-10, for instance from 2-5 or such as from about 1-5 substituted amino acid residues. Likewise, such antibody variant may for example comprise from about 1-30 terminal sequence amino acid residue additions, for instance from about 1-10, such as for instance from about 2-10, for instance from 2-5 or such as from about 1-5 terminal sequence amino acid residue additions. Such antibody variant may also comprise a combination of two or more of such insertions, deletions, substitutions and terminal sequence amino acid residue additions, provided that the variant possesses at least a substantial proportion of the parent antibodies affinity, specificity, and/or selectivity with respect to the target epitope in question.

Typically, amino acid sequence alterations, such as conservative substitution variations, desirably do not substantially change the structural characteristics of the parent sequence (e.g., a replacement amino acid should not tend to disrupt secondary structure that characterizes the function of the parent sequence). Examples of art-recognized polypeptide secondary and tertiary structures are described in, e.g., Proteins, Structures and Molecular Principles (Creighton, Ed., W. H. Freeman and Company, New York (1984)), Introduction to Protein Structure (C. Branden and J. Tooze, eds., Garland Publishing, New York, N.Y. (1991)) and Thornton et at., Nature 354, 105 (1991). Additional principles relevant to the design and construction of peptide variants is discussed in for instance Collinet et al., J Biol Chem 275(23), 17428-33 (2000).

Amino acid sequence variants of an antibody may be obtained by introducing appropriate nucleotide changes into the antibody-encoding nucleic acid (e.g., by site directed mutagenesis) or by chemical peptide synthesis. Such variants include, for example, deletions from, and/or insertions into and/or substitutions of and/or terminal sequence additions of residues within the amino acid sequences of the antibodies of the examples herein. Any combination of deletions, insertions, and substitutions may be made to arrive at a desired variant, provided that the variant possesses at least a substantial proportion of epitope binding characteristics of the parent antibody. Amino acid sequence changes, with respect to a parent antibody, also may alter post-translational processes of the variant antibody with respect to a parent antibody, such as by changing the number or position of glycosylation sites.

Variant antibodies of the present invention may comprise alterations in the hypervariable region, such as in the CDRs. Examples of antibodies suitable for use according to the present invention comprising such CDR variants are described elsewhere herein.

Variant antibodies suitable for use according to the present invention may comprise framework (FR) alterations that are outside the hypervariable region, for instance in the Fc region, which alterations may be associated with advantageous properties, such as changing the functional or pharmacokinetic properties of the antibodies. For example, a substitution or other modification (insertion, deletion, terminal sequence additions or combination of any thereof) in a framework region or constant domain may be associated with an increase in the half-life of the variant antibody with respect to the parent antibody, or may be made to alter the immunogenicity of the variant antibody with respect to the parent antibody, to provide a site for covalent or non-covalent binding to another molecule, or to alter such properties as complement fixation, for instance resulting in a decrease of C1q binding and CDC or of FcγR binding and antibody-dependent cellular cytotoxicity (ADCC). Reference may be had to WO 94/29351 disclosing antibodies having mutations in the N-terminal region of the $C_H2$ domain that alter the ability of the antibodies to bind to FcRI and thereby decreases the ability of the antibodies to bind to C1q which in turn decreases the ability of the antibodies to fix complement The in vivo half-life of the antibodies may also be improved by modifying the salvage receptor epitope of the Ig constant domain or an Ig-like constant domain such that the molecule does not comprise an intact $C_H2$ domain or an intact Ig Fc region, cf. U.S. Pat. No. 6,121,022 and U.S. Pat. No. 6,194,551. The in vivo half-life may furthermore be increased by making mutations in the Fc region, e.g. by substituting threonine for leucine at position 252, threonine for serine at position 254, or threonine for phenylalanine at position 256, cf. U.S. Pat. No. 6,277,375.

In one embodiment, the present invention provides variant antibodies suitable for use according to the present invention wherein potential T cell epitopes in the antibody have been reduced or eliminated through rationale design. The design and construction of deimmunized antibodies may be accomplished by any suitable known technique (see for instance WO9852976 with respect to methods for preparing deimmunized antibodies). Immunogenicity in humans is expected to be eliminated or substantially reduced when such variant antibodies are used.

Other framework mutations may include sequence changes which may reduce susceptibility to proteolysis, reduce susceptibility to oxidation, and/or confer or modify other physicochemical or functional properties on the associated variant antibody.

Amino acid sequence variations in the framework may also result in an altered glycosylation pattern in the variant antibody with respect to a parent antibody. By altering is meant deleting one or more carbohydrate moieties found in the parent antibody, and/or adding one or more glycosylation sites that are not present in the parent antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are common recognition sequences for enzymatic attachment of the carbohydrate moiety to the asparagine side chain. Thus, the presence of either of these tripeptide sequences in a polypeptide may create a potential glycosylation site. O-linked glycosylation refers to the attachment of sugars such as N-aceylgalactosamine, galactose, or xylose to a hydroxyamino acid, most commonly serine or threonine, although 5-hydroxyproline or 5-hydroxylysine may also be used. Addition of glycosylation sites to the antibody may be conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The antibodies may also be expressed in a transfectoma which does not add the fucose unit normally attached to the carbohydrate attached to Asn at position 297 of Fc in order to enhance the affinity of Fc for FcγRIII which in turn will result in an increased ADCC of the antibodies in the presence of NK cells, cf. Shield et al., J. Biol. Chem. 277, 26733 (2002). Furthermore, modification of galactosylation may be made in order to modify CDC. Further reference may be had to WO 99/54342 and Umana et al., Nat. Biotechnol. 17, 176 (1999) disclosing a CHO cell line engineered to express GntIII resulting in the expression of monoclonal antibodies with altered glycoforms and improved ADCC activity.

There are a number of techniques known for generating CDR variants, any suitable technique or combination of which may be used in the context of the present invention for generating CDR variants of the CDRs of the antibodies of the examples. Examples of such techniques include the removal of nonessential residues as described in Studnicka et al., Protein Engineering 7, 805-814 (1994) (see also Soderlind et al., Immunotechnology. 4(3-4), 279-85 (1999), CDR walking mutagenesis and other artificial affinity maturation techniques (see for instance Yang et al., Journal of Molecular Biology 254(3), 392-403 (1995), CDR shuffling techniques wherein typically CDRs are amplified from a diverse set of gene templates optionally comprising synthetic oligonucleotides, the constant regions of the $V_L$, $V_H$, and/or CDRs are amplified, and the various fragments mixed (in single-stranded or double-stranded format) and assembled by polymerase chain reaction (PCR) to produce a set of antibody-fragment encoding gene products carrying shuffled CDR introduced into the master framework, which is amplified using external primers annealing to sites beyond inserted restriction sites to ensure production of full-length products, which are inserted into a vector of choice and used to expressed variant CDR-containing proteins. Appropriate structure may be determined by superimposition of the variant/mimetic structures and those of the parent sequences, e.g., by comparison of NMR solution structures. Useful methods for rational design of CDR sequence variants are described in for instance WO 91/09967 and WO 93/16184. Other potentially suitable techniques for preparing antibodies include CDR walking mutagenesis, antibody chain shuffling, "parsimonious mutagenesis" (Balint and Larrick, Gene 137, 109-118 (1993)), and other affinity maturation techniques (see for instance Wu et al., PNAS USA 95, 6037-42 (1998)). Repertoire cloning procedures may also be useful in the production of variant antibodies (see for instance WO 96/33279). Additional examples of such methods are provided elsewhere herein.

Antibodies suitable for use according to the present invention may also include single chain antibodies. Single chain antibodies are peptides in which the heavy and light chain Fv regions are connected, for instance by joining the heavy and light chains in the Fv of an antibody suitable for use according to the present invention with a flexible peptide linker (typically of about 10, 12, 15 or more amino acid residues) in a single peptide chain. Methods of producing such antibodies are described in for instance U.S. Pat. No. 4,946,778, Pluckthun in The Pharmacology of Monoclonal Antibodies, vol. 113, Rosenburg and Moore eds. Springer-Verlag, New York, pp. 269-315 (1994), Bird et al., Science 242, 423-426 (1988), Huston et al., PNAS USA 85, 5879-5883 (1988) and McCafferty et al., Nature 348, 552-554 (1990). A single chain antibody may be monovalent, if only a single $V_H$ and $V_L$ are used; bivalent, if two $V_H$ and $V_L$ are used; or polyvalent, if more than two $V_H$ and $V_L$ are used.

An antibodies suitable for use according to the present invention may be derivatized or linked to one or more further functional molecules, for instance another peptide or protein (such as a Fab' fragment) to generate a multispecific molecule which binds to multiple binding sites or target epitopes. For example, an antibody of the present invention may be functionally linked (for instance by chemical coupling, genetic fusion, noncovalent association or otherwise) to one or more other binding molecules, such as another antibody, peptide or binding mimetic.

In one embodiment, the multispecific molecules of the present invention comprise as a binding specificity at least one further antibody, including, e.g., an Fab, Fab', F(ab')$_2$, Fv, or a scFv. The further antibody may also be a light chain or heavy chain dimer, or any minimal fragment thereof such as a Fv or a single chain construct as described in Ladner et al., in U.S. Pat. No. 4,946,778. The antibody may also be a binding-domain immunoglobulin fusion protein as disclosed in US 2003/0118592 and US 2003/0133939.

Antibodies suitable for use according to the present invention also include antibody derivatives. Antibody derivatives may be produced by chemically conjugating a radioisotope, protein, or other agent/moiety/compound to the N-terminal side or C-terminal side of the antibody or subunit thereof (for instance an antibody H chain, L chain, or target specific/selective fragment thereof), to an appropriate substituent group or side chain or to a sugar chain in the antibody (see for instance Antibody Engineering Handbook, edited by Osamu Kanemitsu, published by Chijin Shokan (1994)). Derivatives may also be generated by conjugation at internal residues or sugars, where appropriate.

An antibody derivative may for instance be an antibody in which one or more of the amino acid residues of the antibody have been chemically modified (for instance by alkylation, acylation, ester formation, or amide formation) or covalently associated with one or more heterologous substituents (for instance a lipophilic substituent, a PEG moiety, a peptide side chain linked by a suitable organic moiety linker, etc.). In general, the antibodies described herein as suitable for use with the present invention may be modified by inclusion of any suitable number of such modified amino acids and/or associations with such conjugated substituents. Suitability in this context is generally determined by the ability to at least substantially retain selectivity, specificity and/or other antibody specific functionality associated with the non-derivatized parent antibody. The inclusion of one or more modified amino acids may be advantageous in, for example, increasing polypeptide serum half-life, reducing polypeptide antigenicity, or increasing polypeptide storage stability. Amino acid(s) are modified, for example, co-translationally or post-translationally during recombinant production (for instance by N-linked glycosylation at N-X-S/T motifs during expression in mammalian cells) or modified by synthetic means. Non-limiting examples of a modified amino acid include a glycosylated amino acid, a sulfated amino acid, a prenylated (for instance farnesylated, or geranylgeranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols On Cd-Rom, Humana Press, Towata, N.J. The modified amino acid may for instance be selected from a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

For instance, antibodies may be chemically modified by covalent conjugation to a polymer to for instance increase their circulating half-life. Exemplary polymers, and methods to attach them to peptides, are illustrated in for instance U.S. Pat. No. 4,766,106, U.S. Pat. No. 4,179,337, U.S. Pat. No. 4,495,285 and U.S. Pat. No. 4,609,546. Additional illustrative polymers include polyoxyethylated polyols and polyethylene glycol (PEG) (for instance a PEG with a molecular weight of between about 1,000 and about 40,000, such as between about 2000 and about 20,000, for instance about 3,000-12,000).

An "antibody deficient in effector function" or an "effector-function-deficient antibody" refers to an antibody which has a significantly reduced or no ability to activate one or more effector mechanisms, such as complement activation or Fc receptor binding. Thus, effector-function deficient antibodies have significantly reduced or no ability to mediate complement-dependent cytotoxicity (CDC) or antibody-dependent cell-mediated cytotoxicity (ADCC). An example of such an antibody is IgG4.

An "antibody deficient in complement activation" or a "complement activation deficient antibody" is an antibody which has a significantly reduced or no ability to activate complement in vivo, for instance by lack of ability to bind the first component (C1q) of the classical complement system, or by lack of ability to bind or activate other components of the complement system, such as lack of C3 activation.

This effector-function-deficiency may be an inherent feature of the antibody in question. The antibody may for instance be of an isotype, which is incapable of activating complement in vivo, such as for instance the IgG2 or the IgG4 isotype. The deficiency in activating effector functions may also be introduced by framework mutations, which e.g. decrease the ability of the antibodies to fix complement as described elsewhere herein.

In a preferred embodiment of the invention, the effector-function-deficient antibody is an IgG4 antibody. In a further embodiment, the antibody is a variant IgG4 antibody having even further reduced Fc receptor binding activity as compared to wild-type IgG4, e.g. due to residue substitutions as described in Reddy et al. (2000) J. Immunol. 164:1925-33. In another embodiment, the effector-function-deficient antibody is a variant IgG1, IgG2 or IgG3 which contains one or more mutations in the constant regions of the antibody that mediate effector functions.

The inability of a given antibody to activate effector functions may e.g. conveniently be determined by using an assay as described in the Example 4 of the current specification for complement activation. Other ways of determining the ability of a given antibody to activate complement are known to the person skilled in the art. Examples may be found in Current Protocols in Immunology, Eds, Coligan et al., John Wiley & Sons Inc.

In one embodiment, the ability—or lack of ability—of the complement activation deficient antibody to activate complement is compared to the ability of IgG1-637 (as described elsewhere herein) or another IgG1 antibody, which activates complement to about the same degree as IgG1-637. In one embodiment, the complement activation of the complement activation deficient antibody is less than 25%, for instance less than 50%, such as less than 75%, for instance less than 90%, such as less than 95%, for instance less than 99% of the complement activation of the IgG1 antibody.

In one embodiment, the ability—or lack of ability—of the complement activation deficient antibody to activate complement is determined by measuring the C1q binding. The ability—or lack of ability—of the complement activation deficient antibody to bind C1q is compared to the ability of IgG1-637 (as described elsewhere herein) or another IgG1 antibody, which activates complement to about the same degree as IgG1-637, to bind to C1q. In one embodiment, the C1q binding of the complement activation deficient antibody is less than 25%, for instance less than 50%, such as less than 75%, for instance less than 90%, such as less than 95%, for instance less than 99% of the C1q binding of the IgG1 antibody.

A multivalent antibody is an antibody comprising more than one identical binding specificity for the target auto-antigen in question (a bivalent antibody comprises two such binding specificities). The classic example is the typical bivalent immunoglobulin molecule.

Thus, although the discussion herein may focus on antibodies as whole immunoglobulin molecules, it should be understood that the embodiments and features of the multivalent antibodies may equally be applied to antibody fragments, such as $F(ab)_2$ and $F(ab')_2$ fragments, and scFv peptides, antibody-like peptides (peptides comprising a CDR), and bi- and multi-specific antibodies, provided that these retains at least a substantial proportion of the antigen-binding properties of the corresponding complete antibody, and provided that these are multivalent. In some instances, antibody fragments may be associated with lower antigen-binding affinity, but may offer other advantageous features that may offset for any such loss in affinity.

In one embodiment, the multivalent effector-function-deficient antibody is a bivalent antibody.

In one embodiment, the multivalent effector-function-deficient antibody is capable of modulating the activity of the target auto-antigen. Such modulation may for instance be described as modulation of expression, antigen down-modulation, antigen internalization, antigen catabolism, antigen cross-linking, and/or modulation of cellular signaling, as for instance described in Ludwig et al, Oncogene 22, 9097 (2003). An example of determining such modulation of AChR is described in Example 5.

In another embodiment, the multivalent effector-function-deficient antibody is not capable of modulating the activity of the target auto-antigen, or at least not capable of modulating the activity of the target auto-antigen in vivo, e,g., due to in vivo exchange with endogenous immunoglobulins.

The existence of competition between the effector-function-deficient antibody and one or more of the auto-antibodies involved in mediating the antibody-mediated effector-function-auto-immune disease or disorder for binding to a target antigen may be determined in a number of ways known to the person skilled in the art, for instance in an ELISA assay.

Competition in the context of the present invention refers to any detectably significant reduction in the propensity for the auto-antibody to bind the target antigen in the presence of the effector-function-deficient antibody. Typically, competition means an at least about 10%, such as an at least about 15%, for instance an at least about 20%, such as an at least about 25%, for instance an at least about 30%, such as an at least about 35%, for instance an at least about 40%, such as an at least about 45%, for instance an at least about 50%, such as an at least about 55%, for instance an at least about 60%, such as an at least about 65%, for instance an at least about 70%, such as an at least about 75%, for instance an at least about 80%, such as an at least about 85%, for instance an at least about 90%, such as an at least about 95%, for instance an at least about 99% reduction in the binding between auto-antibody and the target antigen in the presence of the effector-function-deficient antibody.

Assessing competition typically involves an evaluation of relative inhibitory binding using a first amount of a first molecule; a second amount of a second molecule; and a third amount of a third molecule (or a standard determined by binding studies that may be reasonably compared to new binding data with respect to the first and second molecules as a surrogate for actual contemporaneous data), wherein the first, second, and third amounts all are sufficient to make a comparison that imparts information about the selectivity and/or specificity of the molecules at issue with respect to the other present molecules. The first, second, and third amounts may vary with the nature of the antibodies and targets involved. Usually, for ELISA assessments about 5-50 µg (e.g., about 10-50 µg, about 20-50 µg, about 5-20 µg, about 10-20 µg, etc.) of antibodies and/or targets are required to assess whether competition exists. Conditions also should be suitable for binding. Typically, physiological or near-physiological conditions (e.g., temperatures of about 20-40° C., pH of about 7-8, etc.) are suitable for antibody-antigen binding.

Often competition is marked by a significantly greater relative inhibition than about 5% as determined by ELISA analysis. Thus, for example, it is possible to set a criterion for competitiveness wherein at least about 10% relative inhibition is detected; at least about 15% relative inhibition is detected; or at least about 20% relative inhibition is detected before a effector-function-deficient antibody and one or more of the auto-antibodies is considered sufficiently competitive. In cases where the epitope for the effector-function-deficient antibody and the auto-antibody are closely located in an antigen, and, as is described elsewhere herein, in the present case, the effector-function-deficient antibody and the auto-antibody binds the same epitope, competition may be marked by greater than about 40% relative inhibition of auto-antibody binding to the target antigen (e.g., at least about 45% inhibition, such as at least about 50% inhibition, for instance at least about 55% inhibition, such as at least about 60% inhibition, for instance at least about 65% inhibition, such as at least about 70% inhibition, for instance at least about 75% inhibition, such as at least about 80% inhibition, for instance at least about 85% inhibition, such as at least about 90% inhibition, for instance at least about 95% inhibition, or higher level of relative inhibition).

Additional methods for determining competitive inhibition may be found in for instance Harlow et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley InterScience N.Y., (1992, 1993), and Muller, Meth. Enzymol. 92, 589-601 (1983)).

The following is a list of selected further embodiments of the present invention.

Embodiment 55

In a main embodiment, the invention relates to the use of an antibody for the preparation of a pharmaceutical composition for treatment of an antibody-mediated auto-immune disease or disorder in a subject, wherein said antibody is capable of competing with one or more of the auto-antibodies involved in mediating the antibody-mediated auto-immune disease or disorder for binding to a target auto-antigen, and wherein said antibody is a monovalent antibody comprising a light chain and a heavy chain, wherein a) said light chain comprises the amino acid sequence of the variable ($V_L$) region of a selected antigen specific antibody and the amino acid sequence of the constant ($C_L$) region of an Ig, and wherein, in case of an IgG1 subtype, the amino sequence of the constant ($C_L$) region has been modified so that it does not contain any amino acids capable of participating in the formation of disulfide bonds or covalent bonds with other peptides comprising an identical amino acid sequence of the constant ($C_L$) region of the Ig, and b) said heavy chain comprises the amino acid sequence of the variable ($V_H$) region of said selected antigen specific antibody and the amino acid sequence of the constant ($C_H$) region of human Ig, wherein the amino acid sequence of the constant ($C_H$) region has been modified so that the hinge region and, as required by the Ig subtype, other regions of the $C_H$ region, such as the $C_H3$ region, does not contain any amino acid residues which participate in the formation of disulphide bonds or covalent or non-covalent inter-heavy chain bonds with other peptides comprising an identical amino acid sequence of the constant ($C_H$) region of the human Ig.

Embodiment 56. The use according to embodiment 55, wherein the human Ig is an IgG1, IgG2, IgG3, IgG4 or IgGA antibody, such as an IgG1, IgG2 or IgG4 antibody.

Embodiment 57: Use of an antibody for the preparation of a pharmaceutical composition for treatment of an antibody-mediated auto-immune disease or disorder in a subject, wherein said antibody is capable of competing with one or more of the auto-antibodies involved in mediating the antibody-mediated auto-immune disease or disorder for binding to a target auto-antigen, and wherein said antibody is a monovalent antibody comprising a light chain and a heavy chain, wherein a) said light chain comprises the amino acid sequence of the variable ($V_L$) region of a selected antigen specific antibody and the amino acid sequence of the constant ($C_L$) region of an Ig, and b) said heavy chain comprises the amino acid sequence of the variable ($V_H$) region of said selected antigen specific antibody and the amino acid sequence of the constant ($C_H$) region of human IgG4, wherein the amino acid sequence of the heavy chain has been modified such that none of any amino acid residues present in the region corresponding to the hinge region are capable of participating in the formation of disulphide bonds with other peptides comprising an identical amino acid sequence of the constant ($C_H$) region of human IgG4.

Embodiment 58: The use according to any of embodiments 55 to 57, wherein the $C_L$ region is the constant region of the kappa light chain of human IgG.

Embodiment 59: The use according to any of embodiments 55 to 58, wherein the $C_L$ region is the constant region of the lambda light chain of human IgG.

Embodiment 60: The use according to any of embodiments 55 to 59, wherein the light chain and the heavy chain are connected to each other via one or more disulphide bond.

Embodiment 61: The use according to any of embodiments 55 to 60, wherein the light chain and the heavy chain are connected to each other via an amide bond.

Embodiment 62: The use according to any of embodiments 55 to 61, wherein the amino acid sequence of the heavy chain has been modified such that the region corresponding to the hinge region does not comprise any cysteine residues.

Embodiment 63: The use according to any of embodiments 55 to 62, wherein the amino acid sequence of the heavy chain has been modified such that at least one of the amino acid residues of the region corresponding to the hinge region, including any cysteine residues, have been deleted and/or substituted with other amino acid residues.

Embodiment 64: The use according to any of embodiments 55 to 63, wherein the cysteine residues of the hinge region are substituted with amino acid residues that have an uncharged polar side chain, or a non polar side chain.

Embodiment 65: The use according to embodiment 64, wherein the amino acids with uncharged polar side chains are independently selected from glycine, asparagine, glutamine, serine, threonine, tyrosine, tryptophan, and the amino acids with the nonpolar side chain are independently selected from alanine, valine, leucine, isoleucine, proline, phenylalanine, methionine.

Embodiment 66: The use according to embodiment 65, wherein the amino acid sequence of the heavy chain has been modified such that the heavy chain comprises a $C_H$ region, wherein the amino acids corresponding to amino acids 106 and 109 of the sequence of SEQ ID No: 19 have been deleted.

Embodiment 67: The use according to embodiment 63 or embodiment 66, wherein the amino acid sequence of the heavy chain has been modified such that the heavy chain comprises a IgG4 $C_H$ region, wherein at least the amino acid residues corresponding to amino acid residues 106 to 109 of the sequence of SEQ ID No: 19 has been deleted.

Embodiment 68: The use according to any of embodiments 63 to 67, wherein the amino acid sequence of the heavy chain has been modified such that the heavy chain comprises a IgG4 $C_H$ region, wherein at least the amino acid residues corresponding to amino acid residues 99 to 110 of the sequence of SEQ ID No: 19 has been deleted.

Embodiment 69: The use according to any of embodiments 63 to 68, wherein the entire hinge region has been deleted.

Embodiment 70: The use according to any of embodiments 63 to 69, wherein the heavy chain comprises the amino acid sequence of SEQ ID No: 20.

Embodiment 71: The use according to embodiment 63, wherein the amino acid sequence of the heavy chain has been modified such that the heavy chain comprises a IgG4 $C_H$ region, wherein the amino acid residues corresponding to amino acid residues 106 and 109 of the sequence of SEQ ID No: 19 has been substituted with amino acid residues different from cysteine.

Embodiment 72: The use according to embodiment 63, wherein the amino acid sequence of the heavy chain has been modified such that the heavy chain comprises a $C_H$ region, wherein one of the amino acid residues corresponding to amino acid residues 106 and 109 of the sequence of SEQ ID No: 19 has been substituted with an amino acid residue different from cysteine, such as an amino acid residue disclosed in embodiment 67 or 68, and the other of the amino acid residues corresponding to amino acid residues 106 and 109 of the sequence of SEQ ID No: 19 has been deleted.

Embodiment 73: The use according to embodiment 72, wherein the amino acid residue corresponding to amino acid residues 106 has been substituted with an amino acid residue that is different from cysteine, such as an amino acid residue disclosed in embodiment 64 or 65, and wherein the amino acid residue corresponding to amino acid residues 109 has been deleted.

Embodiment 74: The use according to embodiment 72, wherein the amino acid residue corresponding to amino acid residues 106 has been deleted, and the amino acid residue corresponding to amino acid residues 109 has been substituted with an amino acid residue different from cysteine, such as an amino acid residue disclosed in embodiment 64 or 65.

Embodiment 75: The use according to any of embodiments 55 to 74, which monovalent antibody has a plasma concentration above 10 μg/ml for more than 7 days when administered in vivo at a dose of 4 mg per kg.

Embodiment 76: The use according to embodiment 75, wherein the monovalent antibody has a plasma concentration above 10 μg/ml for more than 7 days when administered in vivo in SCID mice at a dose of 4 mg per kg.

Embodiment 77: The use according to any of embodiments 55 to 76, which monovalent antibody has a plasma clearance, which is more than 10 times slower than the plasma clearance of a F(ab')$_2$ fragment.

Embodiment 78: The use according to embodiment 77, wherein the sequence of the F(ab')$_2$ fragment is identical to the sequence of the corresponding region of the monovalent antibody.

Embodiment 79: The use according to embodiment 77, wherein the plasma clearance is measured using SCID mice.

Embodiment 80: The use according to embodiment 79, wherein the $V_H$ region and the $V_L$ region of the F(ab')$_2$ fragment are identical to the $V_H$ region and the $V_L$ region of the monovalent antibody.

Embodiment 81: The use according to any of embodiments 55 to 80, wherein said monovalent antibody has a half-life of at least 5 days when administered in vivo.

Embodiment 82: The use according to any one of embodiments 55 to 80, wherein said monovalent antibody has a half-life of at least 14 days.

Embodiment 83: The use according to any one of embodiments 55 to 80, wherein said monovalent antibody has a half-life of at least 21 days.

Embodiment 84: The use according to embodiment 81, wherein said monovalent antibody has a half-life of at least 5 days when administered in vivo in SCID mice.

Embodiment 85: The use according to any of embodiments 55 to 84, wherein said antibody is capable of binding to FcRn.

Embodiment 86: The use according to any of embodiments 55 to 85, wherein the monovalent antibody when bound to a target molecule inhibits target molecule multimerization and/or aggregation.

Embodiment 87: The use according to any of embodiments 55 to 86, wherein the monovalent antibody is in a monovalent form in the presence of polyclonal human IgG.

Embodiment 88: The use according to any of embodiments 55 to 86, wherein the monovalent antibody is in a monovalent form when administered to a human being.

Embodiment 89: The use according to any of embodiments 55 to 86, wherein the monovalent antibody dissociates into a monovalent form in the presence of polyclonal human IgG.

Embodiment 90: The use according to any of embodiments 55 to 86, wherein the monovalent antibody dissociates into in a monovalent form when administered to a human being.

Embodiment 91: The use according to any of embodiments 55 to 90, wherein the heavy chain CDR1, CDR2 and CDR3 regions and the light chain CDR1, CDR2 and CDR3 regions of the monovalent antibody have a sequence identical to the heavy chain CDR1, CDR2 and CDR3 regions and the light chain CDR1, CDR2 and CDR3 regions, respectively, of an auto-antibody involved in mediating the antibody-mediated auto-immune disease or disorder.

Embodiment 92: The use according to any of embodiments 55 to 91, wherein the monovalent antibody is a human antibody.

Embodiment 93: The use according to any of embodiments 55 to 92, wherein the antibody-mediated auto-immune disease or disorder is myasthenia gravis.

Embodiment 94: The use according to any of embodiments 55 to 93, wherein the target auto-antigen is the nicotinic acetylcholine receptor of the muscle.

Embodiment 95: The use according to any of embodiments 55 to 94, wherein the monovalent antibody is derived from anti-AChR Fab-637.

Embodiment 96: The use according to any of embodiments 55 to 95, wherein the heavy chain CDR1, CDR2 and CDR3 regions and the light chain CDR1, CDR2 and CDR3 regions of the effector-function-deficient antibody have a sequence identical to the heavy chain CDR1, CDR2 and CDR3 regions and the light chain CDR1, CDR2 and CDR3 regions, respectively, of anti-AChR Fab-637.

Embodiment 97: The use according to any of embodiments 55 to 96, wherein the monovalent antibody comprises a $V_H$ region having the amino acid sequence of SEQ ID No: 2.

Embodiment 98: The use according to any of embodiments 55 to 97, wherein the monovalent antibody comprises a $V_L$ region having the amino acid sequence of SEQ ID No: 4.

The monovalent antibodies used in the above embodiments can be constructed by standard recombinant DNA and heterologous expression techniques, e.g. those referred to herein. Construction of such antibodies has also been described in a PCT application entitled "Recombinant monovalent antibodies and methods for production thereof" (Genmab) filed on Nov. 28, 2006, which is hereby incorporated by reference.

In a further embodiment of the use of the invention, the effector-function-deficient antibody binds to the same epitope as one or more of the auto-antibodies.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the antibody (in other words, the amino acid residue is within the footprint of the antibody). An epitope in the context of the present invention includes any peptide or peptide-derivative determinant capable of specific binding to an immunoglobulin. An epitope may comprise any suitable number of amino acids, in any suitable position, orientation, amino acid composition (and consequently, at least in part, charge). Thus, for example, an epitope may be composed of about 3-10 amino acids, typically 3-8 amino acids, in one or more contiguous or noncontiguous locations with respect to the primary sequence of the target antigen (for instance an epitope may consist essentially of 2, 3, 4, 5, 6, 7, or 8 amino acid residues distributed in 1, 2, 3, 4, or 5 noncontiguous locations in the target antigen). Alternatively, for example, an epitope may be considered to be defined by a region of about 5-40 contiguous amino acid residues (e.g., about 7-30 amino acid residues, about 5-20 amino acid residues, or about 3-15 amino acid residues) in the target antigen. In some epitopes it may be the case that just one amino acid residue or only a few amino acid residues are critical to CDR or CDR(s) recognition (and thereby most important to antibody-antigen affinity and avidity). As such, an epitope may be characterized on the basis of one or more of such critical residues, with the recognition that other residues may also make some lesser contribution to the epitope. In the case of an epitope defined by a region of amino acids, it may be that one or more amino acids in the region make only a minor contribution or even negligible contribution to antibody binding, such that the residue may be subject to substitution with an appropriate different residue without resulting in "a loss" of the epitope.

An epitope bound by an auto-antibody may be identified via standard mapping and characterization techniques, further refinement of which may be identified by any suitable technique, numerous examples of which are available to the skilled artisan. As one example of such mapping/characterization methods, an epitope for a given auto-antibody may be determined by epitope "foot-printing" using chemical modification of the exposed amines/carboxyls in the target antigen. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions may be identified at this point by peptic proteolysis, fast microbore high-performance liquid chromatography separation, and/or electrospray ionization mass spectrometry. See, e.g., Ehring H, Analytical Biochemistry, Vol. 267 (2) 252-259 (1999) and/or Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with $^{15}N$ so that only signals corresponding to the antigen and no signals from the antigen binding peptide are seen in the NMR-spectrum. Antigen signals originating from amino acids involved in the interaction with the antigen binding peptide typically will shift position in the spectra of the complex compared to the spectra of the free antigen, and the amino acids involved in the binding may be identified that way. See for instance Ernst Schering Res Found Workshop. (44), 149-67 (2004), Huang et al., Journal of Molecular Biology 281(1), 61-67 (1998) and Saito and Patterson, Methods. 9(3), 516-24 (1996).

Epitope mapping/characterization may also be performed using mass spectrometry methods. See for instance Downward, J Mass Spectrom. 35(4), 493-503 (2000) and Kiselar and Downard, Anal Chem. 71(9), 1792-801 (1999).

Protease digestion techniques may also be useful in the context of epitope mapping and identification. Antigenic determinant-relevant regions/sequences may be determined by protease digestion, e.g. by using trypsin in a ratio of about 1:50 to the target antigen o/n digestion at 37° C. and pH 7-8, followed by mass spectrometry (MS) analysis for peptide identification. The peptides protected from trypsin cleavage by the antibody may subsequently be identified by comparison of samples subjected to trypsin digestion and samples incubated with the target antigen and then subjected to digestion by e.g. trypsin (thereby revealing a foot print for the binder). Other enzymes like chymotrypsin, pepsin, etc. may also or alternatively be used in a similar epitope characterization method. An effector-function-deficient antibody, which gives the significantly same result as an auto-antibody in these measurements is deemed to be an antibody that bind the same epitope as the auto-antibody. See for instance Manca, Ann Ist Super Sanita. 27(1), 15-9 (1991) for a discussion of similar techniques.

Epitope mapping by competitive binding to the target antigen with two antibodies where one is biotinylated is another method for identifying relevant antigenic determinant regions.

Various phage display techniques may also be used to identify epitopes. See for instance Wang and Yu, Curr Drug Targets. 5(1), 1-15 (2004), Burton, Immunotechnology. 1(2), 87-94 (August 1995), Cortese et al., Immunotechnology. 1(2), 87-94 (1995) and Irving et al., Curr Opin Chem Biol. 5(3), 314-24 (2001). Consensus epitopes may also be identified through modified phage display-related techniques (see, http://www.cs.montana.edu/~mumey/papers/jcb03.pdf) for discussion.

Other methods potentially helpful in mapping epitopes include crystallography techniques, X-ray diffraction techniques (such as the X-ray diffraction/sequence study techniques developed by Poljak and others in the 1970s-1980s), and the application of Multipin Peptide Synthesis Technology. Computer-based methods such as sequence analysis and three dimensional structure analysis and docking may also be used to identify antigenic determinants. For example, an epitope may also be determined by molecular modeling using a structure of the target antigen with docking of the structure of the Fab fragment of the individual monoclonal antibody. These and other mapping methods are discussed in Epitope Mapping A Practical Approach (Westwood and Hay Eds.) 2001 Oxford University Press.

In one embodiment, the effector-function-deficient antibody, such as the multivalent effector-function-deficient antibody, is derived from an auto-antibody involved in the mediating the antibody-mediated auto-immune disease or disorder. By "derived" means that the sequence of the CDR regions of the auto-antibody is used to design the sequences of the effector-function-deficient antibody, in order to achieve an effector-function-deficient antibody which has the same binding specificities as the auto-antibody involved in the mediating the antibody-mediated auto-immune disease or disorder.

In one embodiment, the heavy chain CDR3 region of the effector-function-deficient antibody, such as the multivalent effector-function-deficient antibody, has a sequence identical to the heavy chain CDR3 region of an auto-antibody involved in the mediating the antibody-mediated auto-immune disease or disorder.

In one embodiment, the heavy chain CDR1, CDR2 and CDR3 regions and the light chain CDR1, CDR2 and CDR3 regions of the effector-function-deficient antibody, such as the multivalent effector-function-deficient antibody, have a sequence identical to the heavy chain CDR1, CDR2 and CDR3 regions and the light chain CDR1, CDR2 and CDR3 regions, respectively, of an auto-antibody involved in the mediating the antibody-mediated auto-immune disease or disorder.

An "auto-immune disease or disorder" is a disease or disorder, wherein the subject experiences an immune response against self antigens, also known as autoantigens, which immune response has an adverse effect on the body. An immune response against autoantigens is termed an auto-immune response, and it may occur to some extent in a normal healthy subject, but in a subject suffering from an auto-immune disease, the auto-immune response is pathological. A clinical sign of such an auto-immune disease or disorder is the presence of antibodies or T lymphocytes reactive with autoantigens. The self-reactive antibodies are known as autoantibodies and the cells as autoreactive T lymphocytes. An antibody-mediated auto-immune disease or disorder is a disease or disorder, where the pathological response is mediated by auto-antibodies, as exemplified by research on systemic lupus erythematosus and other auto-immune diseases (for example in Chalkiadakis et al., Am J Gastroenterol. 94, 2551 (1999); Boehm et al., Eur J Clin Invest. 24, 248 (1994); Jacob and Viard, Eur J Med. 1, 425 (1992)). An "antibody-mediated complement-dependent auto-immune disease or disorder" is an antibody-mediated auto-immune disease or disorder, wherein the presence and/or development of the antibody-mediated auto-immune disease or disorder is dependent on an active complement system. Such complement-dependency may for instance be demonstrated in disease models in complement deficient animals (for instance in Lennon and Lambert, Annals NY Acad. Sci. 377, 77 (1981)) or by demonstrating complement-deposition in autoimmune lesions or by measuring complement activation and/or consumption in patient serum, exemplified in Antonelli et al., Clin Exp Rheumatol. 15, S31 (1996)

In one embodiment, said antibody-mediated auto-immune disease or disorder is myasthenia gravis. In a further embodiment, the target antigen is an ion channel, such as the nicotinic acetylcholine receptor of the muscle. In a further embodiment, the effector-function-deficient antibody, such as the multivalent effector-function-deficient antibody, is derived from the patient derived anti-AChR Fab 637. In one embodiment, the effector-function-deficient antibody, such as the multivalent effector-function-deficient antibody, has a $V_H$ CDR3 region of the same amino acid sequence as the CDR3 region of anti-AChR Fab-637. In a further embodiment, the heavy chain CDR1, CDR2 and CDR3 regions and the light chain CDR1, CDR2 and CDR3 regions of the effector-function-deficient antibody, such as the multivalent effector-function-deficient antibody, have a sequence identical to the heavy chain CDR1, CDR2 and CDR3 regions and the light chain CDR1, CDR2 and CDR3 regions, respectively, of anti-AChR Fab-637. In one embodiment, the effector-function-deficient antibody, such as the multivalent effector-function-deficient antibody, comprises a $V_H$ region having the amino acid sequence of SEQ ID No: 2. In one embodiment, the effector-function-deficient antibody, such as the multivalent effector-function-deficient antibody, comprises a $V_L$ region having the amino acid sequence of SEQ ID No: 4. In one embodiment, the effector-function-deficient antibody, such as the multivalent effector-function-deficient antibody, competes with anti-AChR Fab-637 for binding to AChR. In one embodiment, the effector-function-deficient antibody, such as the multivalent effector-function-deficient antibody, binds to the same epitope as anti-AChR Fab-637.

In another embodiment, the antibody-mediated auto-immune disease is selected from: psoriasis, psoriatic arthritis, dermatitis, systemic scleroderma and sclerosis, inflammatory bowel disease (IBD), Crohn's disease, ulcerative colitis, respiratory distress syndrome, meningitis, encephalitis, uveitis, glomerulonephritis, eczema, asthma, atherosclerosis, leukocyte adhesion deficiency, multiple sclerosis, Raynaud's syndrome, Sjögren's syndrome, juvenile onset diabetes, Reiter's disease, Behcet's disease, immune complex nephritis, IgA nephropathy, IgM polyneuropathies, immune-mediated thrombocytopenias, such as acute idiopathic thrombocytopenic purpura and chronic idiopathic thrombocytopenic purpura, hemolytic anemia, myasthenia gravis, lupus nephritis, systemic lupus erythematosus, rheumatoid arthritis (RA), atopic dermatitis, pemphigus, Graves' disease, Hashimoto's thyroiditis, Wegener's granulomatosis, Omenn's syndrome, chronic renal failure, acute infectious mononucleosis, HIV, and herpes virus associated diseases. Further examples are severe acute respiratory distress syndrome and choreoretinitis.

In one embodiment, the antibody-mediated auto-immune disease or disorder is rheumatoid arthritis or systemic lupus erythematosus, and the target auto-antigen is calpastatin.

In one embodiment, the antibody-mediated auto-immune disease or disorder is rheumatoid arthritis, and the target auto-antigen is follistatin-related protein.

In one embodiment, the antibody-mediated auto-immune disease or disorder is rheumatoid arthritis or systemic lupus erythematosus, and the target auto-antigen is Ro60 kDa.

A "therapeutically effective amount" refers to an amount effective, at dosages and for periods of time necessary, to achieve a desired therapeutic result. A therapeutically effective amount of an antibody suitable for use according to the present invention may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

As used herein, the term "subject" includes any human or non-human primate.

"Treatment" means the administration of an effective amount of a therapeutically active compound of the present invention with the purpose of preventing, easing, ameliorating, or eradicating (curing) symptoms or disease states.

The antibodies according to the present invention are typically used in and provided in an at least substantially isolated—or simply isolated—form. A substantially isolated molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition (e.g., the composition will exhibit at least about 98%, 98%, or 99% homogeneity for the antibody in the context of all present peptide species)).

An isolated molecule refers to a molecule that is not associated with significant levels (such as more than about 1%, more than about 2%, more than about 3%, or more than about 5%) of any extraneous and undesirable physiological factors, such as biomolecules not binding to the target auto-antigen contained within a cell or animal in which the antibody is produced. An isolated molecule also refers to any molecule that has passed through such a stage of purity due to human intervention (whether automatic, manual, or both). In many of the various compositions provided by the present invention, such as in a composition comprising one or more pharmaceutically acceptable carriers, an antibody may be present in relatively small amounts in terms of numbers of total molecular species in the composition (for instance in the case of a composition comprising a large amount of a pharmaceutically acceptable carrier, stabilizer, and/or preservative). In some cases additional peptides, such as BSA, may be included in such a composition with a previously purified antibody. However, provided that such additional constituents of the composition are acceptable for the intended application of the antibody, such a composition can still be described as comprising an isolated antibody according to the present invention. Such a composition may also comprise more than one of such isolated antibodies.

The term "$k_d$" ($sec^{-1}$), as used herein, refers to the dissociation equilibrium rate of a particular antibody-antigen interaction. Said value is also referred to as the $k_{off}$ value.

The term "$k_a$" ($M^{-1} \times sec^{-1}$), as used herein, refers to the association equilibrium rate of a particular antibody-antigen interaction.

The term "$K_D$" (M), as used herein, refers to the dissociation equilibrium constant of a particular antibody-antigen interaction.

The term "$K_A$" ($M^{-1}$), as used herein, refers to the association equilibrium constant of a particular antibody-antigen interaction and is obtained by dividing the $k_a$ by the $k_d$.

As used herein, "glycosylation pattern" is defined as the pattern of carbohydrate units that are covalently attached to a protein, more specifically to an immunoglobulin (antibody) protein. A glycosylation pattern of a heterologous antibody may be characterized as being substantially similar to glycosylation patterns which occur naturally on antibodies produced by the species of the non-human transgenic animal, when one of ordinary skill in the art would recognize the glycosylation pattern of the heterologous antibody as being more similar to said pattern of glycosylation in the species of the non-human transgenic animal than to the species from which the $C_H$ genes of the transgene were derived.

As used herein, "isotype" refers to the immunoglobulin class (for instance IgG1, IgG2, IgG3, IgG4, IgD, IgA, IgE, or IgM) that is encoded by heavy chain constant region genes.

As used herein, "isotype switching" refers to the phenomenon by which the class, or isotype, of an antibody changes from one immunoglobulin class to one of the other immunoglobulin classes.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, NS/0 cells, and lymphocytic cells.

The term "regulatory sequence" is intended to include promoters, enhancers and other expression control elements (for instance polyadenylation signals) that control the transcription or translation of the antibody chain genes. Such regulatory sequences are described, for example, in Goeddel, Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Examples of regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or β-globin promoter As used herein, "specific binding" refers to the binding of an antigen binding peptide, such as an antibody, to a predetermined antigen. Typically, the antigen binding peptide, such as an antibody, binds with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte, and binds to the predetermined antigen with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antigen binding peptide, so that when the $K_D$ of the antigen binding peptide is very low (that is, the antigen binding peptide is highly specific), then the amount with which the affinity for the antigen is lower than the affinity for a non-specific antigen may be at least 10,000 fold. The phrases "an antigen binding peptide recognizing an antigen" and "an antigen binding peptide specific for an antigen" are used interchangeably herein with the term "an antigen binding peptide which binds specifically to an antigen". Likewise, the phrases "an antibody recognizing an antigen" and "an antibody specific for an antigen" are used interchangeably herein with the term "an antibody which binds specifically to an antigen".

The term "transfectoma", as used herein, includes recombinant eukaryotic host cells expressing the antibody, such as CHO cells, NS/0 cells, HEK293 cells, plant cells, or fungi, including yeast cells.

The terms "transgenic, non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human antibodies against a given target antigen, when immunized with said antigen and/or cells expressing said antigen. The human heavy chain transgene may be integrated into the chromosomal DNA of the mouse, as is the case for transgenic mice, for instance HuMAb mice, such as HCo7 or HCo12 mice, or the human heavy chain transgene may be maintained extrachromosomally, as is the case for transchromosomal KM mice as described in WO02/43478. Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching. Transgenic, nonhuman animal can also be used for production of antibodies against a specific antigen by introducing genes encoding such specific antibody, for example by operatively linking the genes to a gene which is expressed in the milk of the animal.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (for instance bacterial vectors having a bacterial origin of replication and episomal mammalian vectors). Other vectors (such as non-episomal mammalian vectors) may be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (such as replication defective retroviruses, adenoviruses and adeno-associated viruses), which serve equivalent functions.

In one embodiment, the present invention provides a nucleic acid encoding an antibody suitable for use according to the present invention.

The term "nucleic acid molecule", as used herein, is intended to include DNA molecules and RNA molecules. A nucleic acid molecule may be single-stranded or double-stranded, but is preferably double-stranded DNA. The nucleic acids may be present in whole cells, in a cell lysate, or in a partially purified or substantially pure form. A nucleic acid is "isolated" or "rendered substantially pure" when purified away from other cellular components or other contaminants, such as other cellular nucleic acids or proteins, by standard techniques, including alkaline/SDS treatment, CsCl banding, column chromatography, agarose gel electrophoresis and others well known in the art. See, F. Ausubel et al., ed. Current Protocols in Molecular Biology, Greene Publishing and Wiley InterScience New York (1987).

Such nucleic acid may have any suitable characteristics and comprise any suitable features or combination thereof. Thus, for example, such nucleic acid may be in the form of DNA, RNA, or a hybrid thereof, and may include nonnaturally-occurring bases, a modified backbone (e.g., a phosphothioate backbone that promotes stability of the nucleic acid), or both. The nucleic acid advantageously comprises features that promote desired expression in target host cell(s), replication, and/or selection. Examples of such features include an origin of replication component, a selection gene component, a promoter component, an enhancer element component, a $V_H$ coding region, a $V_L$ coding region, a constant heavy chain coding region, a constant light chain coding region, a polyadenylation sequence component, a termination component, and the like.

In one embodiment, the present invention provides a vector comprising such nucleic acid. A vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. The vector may for instance be suitable for expression of the antibody in a bacterial cell, in a yeast system or in a mammalian system.

A nucleic acid encoding an antibody suitable for use according to the present invention may comprise or be associated with any suitable promoter, enhancer, and other expression-facilitating elements. In one embodiment, the nucleic acid may be positioned in and/or delivered to the host cell or host animal via a viral vector.

Other features of the present invention include recombinant cells, such as yeast, bacterial, and mammalian cells (e.g., immortalized mammalian cells) comprising such a nucleic acid, vector, or combinations of either or both thereof. For example, in one embodiment, the present invention provides a cell comprising a nucleic acid stably integrated into the cellular genome that comprises a sequence coding for expression of an antibody suitable for use according to the present invention. In one embodiment, the present invention provides a cell comprising a non-integrated nucleic acid, such as a plasmid, cosmid, phagemid, or linear expression element, which comprises a sequence coding for expression of an antibody suitable for use according to the present invention.

An antibody suitable for use according to the present invention may for instance be prepared by recombinant expression in any suitable type of cells or animals. Recombinant antibodies suitable for use according to the present invention also include antibodies isolated from a recombinant, combinatorial human antibody library, antibodies isolated from an animal, such as a transgenic animal, or antibodies prepared, expressed, created or isolated by any other means that involves splicing of human immunoglobulin-encoding nucleic acid sequences to other nucleic acid sequences exogenous to the human immunoglobulin-encoding nucleic acids and human immunoglobulin-encoding genes. Recombinant human antibodies typically have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and, thus, the amino acid sequences of the $V_H$ and $V_L$ regions of the recombinant antibodies may be sequences that, while derived from and related to human germline $V_H$ and $V_L$ sequences, may not naturally exist within the human antibody germline repertoire in vivo. Both types of human antibodies are provided by the present invention. Suitable methods for antibody production are known in the art and include those described in for instance Harlow et al., Antibodies: A Laboratory Manual, Cold Spring Harbor Laboratory Press, Cold Spring Harbor, N.Y., (1988), Harlow and Lane: Using Antibodies: A Laboratory Manual (Cold Spring Harbor Laboratory Press (1999)), U.S. Pat. No. 4,376,110 and Ausubel et al., eds., Current Protocols In Molecular Biology, Greene Publishing Assoc. and Wiley InterScience N.Y., (1987, 1992). Monoclonal antibodies may be made using the hybridoma method first described by Kohler et al., Nature 256, 495 (1975), or by other well-known, subsequently-developed methods (see, e.g., Goding, Monoclonal Antibodies: Principles and Practice, pp. 59-103 (Academic Press, 1986)). Hybridomas useful in the production of an antibody suitable for use according to the present invention are also provided by the present invention. Transformed immortalized B cells may also be used to efficiently produce antibodies of the present invention and are also provided by the present invention. Thus, stable and continuous and/or immortalized cells and cell lines expressing antibodies suitable for use according to the present invention are a feature of the present invention. Transgenic animals, such as non-human primates, rodents (for instance hamsters, guinea pigs, and rats—including modified strains thereof such as severe combined immunodeficient (SCID) mice and other immunocompromised animal strains), dogs, etc., expressing an antibody suitable for use according to the present invention are also provided by the present invention.

Recombinant cells comprising exogenous nucleic acids encoding an antibody suitable for use according to the present invention may be prepared by any suitable technique (for instance transfection/transformation with a naked DNA plasmid vector, viral vector, invasive bacterial cell vector or other whole cell vector, etc., comprising an antibody-encoding sequence (or sequences) delivered into the cell by calcium phosphate-precipitation facilitated transfection, receptor-mediated targeting and transfection, biolistic delivery, electroporation, dextran-mediated transfection, liposome-mediated transformation, protoplast fusion, direct microinjection, etc.). Methods of transforming/transfecting cells are well known in the art (see, e.g., Sambrook et al., Molecular Cloning: A Laboratory Manual, Cold Spring Harbor Laboratory Press (2d Edition, 1989 and 3rd Edition, 2001) and F. Ausubel et al., ed. Current Protocols in Molecular Biology, Greene Publishing and Wiley InterScience New York (1987). Such recombinant cells are a feature of the present invention.

Cell lines available as hosts for recombinant protein expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, and a number of other cell lines. Other cell lines that may be used are insect cell lines, such as Sf9 cells. When nucleic acids (or nucleic acid-containing vectors) encoding antibodies suitable for use according to the present invention are introduced into mammalian host cells, antibodies may be produced by culturing the host cells for a period of time sufficient to allow for expression of the antibody in the host cells or by secretion of the antibody into the culture medium in which the host cells are grown. Antibodies may be recovered from the culture medium using standard protein purification methods. Antibodies may also be recovered from host cell lysates when directly expressed without a secretory signal.

An antibody suitable for use according to the present invention may also be produced by a variety of other techniques, for instance phage display techniques using libraries of human antibody genes. In one embodiment, antibodies suitable for use according to the present invention of the present invention produced by use of hybridomas generated in a murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

To generate a fully human monoclonal antibody suitable for use according to the present invention, transgenic or transchromosomal mice containing human immunoglobulin genes (e.g., HCo12, HCo7, HCo17, HCo20 or KM mice) may be immunized with an enriched preparation of the specific target antigen and/or cells expressing the target antigen, as described, for example, by Lonberg et al., (1994), supra, Fishwild et al., (1996), supra, and WO 98/24884. Alternatively, mice may be immunized with DNA encoding the target antigen.

An IgG4 antibody having the same antigen specificity as an auto-antibody may be generated by introducing the $V_L$ and $V_H$ coding region of an auto-antibody into an expression vector encoding the constant region of human IgG4, using standard cloning and expression techniques.

Antibodies suitable for use according to the present invention may also be produced in a host cell transfectoma using, for example, a combination of recombinant DNA techniques and gene transfection methods as is well known in the art, see for instance Morrison, S., Science 229, 1202 (1985). For example, to express the antibodies, or antibody fragments thereof, DNAs encoding partial or full-length light and heavy chains, may be obtained by standard molecular biology techniques (for instance PCR amplification, site directed mutagenesis) and may be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene may be inserted into separate vectors or, more typically, both genes are inserted into the same expression vector. The antibody genes may be inserted into the expression vector by standard methods (e.g., ligation of complementary restriction sites on the antibody gene fragment and vector, or blunt end ligation if no restriction sites are present). The light and heavy chain variable regions of the antibodies described herein may be used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the CL segment within the vector. Additionally or alternatively, the recombinant expression vector may encode a signal peptide that facilitates secretion of the antibody chain from a host cell. The antibody chain gene may be cloned into the vector such that the signal peptide is linked in-frame to the amino terminus of the antibody chain gene. The signal peptide may be an immunoglobulin signal peptide or a heterologous signal peptide (i.e., a signal peptide from a non-immunoglobulin protein).

In addition to the antibody chain genes, the recombinant expression vectors of the present invention carry regulatory sequences that allows and control the expression of the antibody chain genes in a host cell.

In addition to the antibody chain genes and regulatory sequences, the recombinant expression vectors of the present invention may carry additional sequences, such as sequences that regulate replication of the vector in host cells (e.g., origins of replication) and selectable marker genes. The selectable marker gene facilitates selection of host cells into which the vector has been introduced (see for instance U.S. Pat. No. 4,399,216, U.S. Pat. No. 4,634,665 and U.S. Pat. No. 5,179,017). For example, typically the selectable marker gene confers resistance to drugs, such as G418, hygromycin or methotrexate, on a host cell into which the vector has been introduced. Examples of selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The host cells may be prokaryotic or eukaryotic, such as mammalian, host cells. For instance antigen binding fragments may be expressed in prokaryotic host cells and full-length antibodies may be expressed in eukaryotic host cells.

In one embodiment the antibodies are expressed in eukaryotic cells, such as mammalian host cells. Examples of mammalian host cells for expressing the recombinant antibodies of the present invention include CHO cells (including dhfr-CHO cells, described in Urlaub and Chasin, PNAS USA 77, 4216-4220 (1980), used with a DHFR selectable marker, for instance as described in R. J. Kaufman and P. A. Sharp, Mol. Biol. 159, 601-621 (1982)), NS/0 myeloma cells, COS cells, HEK293 cells and SP2.0 cells. In particular for use with NS/0 myeloma cells, another example of a expression system is the GS (glutamine synthetase) gene expression system disclosed in WO87/04462, WO89/01036 and EP338 841.

In one embodiment, the present invention provides a pharmaceutical composition comprising an antibody suitable for use according to the present invention. The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995. The pharmaceutically acceptable carriers or diluents as well as any other known adjuvants and excipients should be suitable for the chosen antibody and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.) on antigen binding. A pharmaceutical composition of an antibody suitable for use according to the present invention may also include diluents, fillers, salts, buffers, detergents (e. g., a nonionic detergent, such as Tween-80), stabilizers, stabilizers (e. g., sugars or protein-free amino acids), preservatives, tissue fixatives, solubilizers, and/or other materials suitable for inclusion in a pharmaceutical composition.

The actual dosage levels of the antibody in the pharmaceutical composition may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular antibody employed, or the ester, salt or amide thereof, the route of administration, the time of administration, the rate of excretion of the particular antibody being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a compound of the present invention in vivo and in vitro are well known in the art and may be selected by those of ordinary skill in the art. The antibodies suitable for use according to the present invention may be administered via any suitable route.

In one embodiment, the pharmaceutical composition is administered parenterally. The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion. In one embodiment that pharmaceutical composition is administered by intravenous or subcutaneous injection or infusion. In one embodiment the antibody is administered in crystalline form by subcutaneous injection, cf. Yang et al., PNAS USA 100(12), 6934-6939 (2003).

The pharmaceutical compositions may be administered with medical devices known in the art. For example, in one embodiment, a pharmaceutical composition of the present invention may be administered with a needleless hypodermic injection device, such as the devices disclosed in U.S. Pat. No. 5,399,163, U.S. Pat. No. 5,383,851, U.S. Pat. No. 5,312,335, U.S. Pat. No. 5,064,413, U.S. Pat. No. 4,941,880, U.S. Pat. No. 4,790,824, or U.S. Pat. No. 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

As mentioned elsewhere, the pharmaceutical compositions may be formulated for particular routes of administration, such as oral, nasal, topical (including buccal, transdermal and sublingual), rectal, vaginal and/or parenteral administration. The pharmaceutical compositions may conveniently be presented in unit dosage form and may be prepared by any methods known in the art of pharmacy. The amount of active ingredient which may be combined with a carrier material to produce a single dosage form will vary depending upon the subject being treated, and the particular mode of administration. The amount of active ingredient which may be combined with a carrier material to produce a single dosage form will generally be that amount of the composition which produces a therapeutic effect. Generally, out of one hundred per cent, this amount will range from about 0.01% to about 99% of active ingredient, such as from about 0.1% to about 70%, for instance from about 1% to about 30%.

Regardless of the route of administration selected, the antibodies suitable for use according to the present invention, which may be used in the form of a pharmaceutically acceptable salt or in a suitable hydrated form, and/or the pharmaceutical compositions are formulated into pharmaceutically acceptable dosage forms by conventional methods known to those of skill in the art. A "pharmaceutically acceptable salt" refers to a salt that retains the desired biological activity of the parent compound and does not impart any undesired toxicological effects (see for instance Berge, S. M. et al., J. Pharm. Sci. 66, 1-19 (1977)). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous acids and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention. Examples of suitable aqueous and nonaqueous carriers which may be employed in the pharmaceutical compositions include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts. Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the antibody, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

The pharmaceutical compositions may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. The pharmaceutical compositions may also comprise isotonicity agents, such as sugars, polyalcohols such as mannitol, sorbitol, glycerol or sodium chloride in the compositions Pharmaceutically acceptable diluents include saline and aqueous buffer solutions.

The pharmaceutical compositions may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. Antibodies suitable for use according to the present invention may for instance be admixed with lactose, sucrose, powders (e.g., starch powder), cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol. Other examples of adjuvants are QS21, GM-CSF, SRL-172, histamine dihydrochloride, thymocartin, Tio-TEPA, monophosphoryl-lipid A/micobacteria compositions, alum, incomplete Freund's adjuvant, montanide ISA, ribi adjuvant system, TiterMax adjuvant, syntex adjuvant formulations, immune-stimulating complexes (ISCOMs), gerbu adjuvant, CpG oligodeoxynucleotides, lipopolysaccharide, and polyinosinic:polycytidylic acid.

Prevention of presence of microorganisms may be ensured both by sterilization procedures and by the inclusion of various antibacterial and antifungal agents, for example, paraben, chlorobutanol, phenol, sorbic acid, and the like. In addition, prolonged absorption of the injectable pharmaceutical form may be brought about by the inclusion of agents which delay absorption such as aluminum monostearate and gelatin.

Pharmaceutical compositions of the present invention comprising an antibody suitable for use according to the present invention may also include a suitable salt therefore. Any suitable salt, such as an alkaline earth metal salt in any suitable form (e.g., a buffer salt), may be used in the stabilization of the antibody. Suitable salts typically include sodium chloride, sodium succinate, sodium sulfate, potassium chloride, magnesium chloride, magnesium sulfate, and calcium chloride. In one embodiment, an aluminum salt is used to stabilize an antibody suitable for use according to the present invention in a pharmaceutical composition, which aluminum salt also may serve as an adjuvant when such a composition is administered to a patient.

The pharmaceutical compositions may be in a variety of suitable forms. Such forms include, for example, liquid, semi-solid and solid dosage forms, such as liquid solutions (e.g., injectable and infusible solutions), dispersions or suspensions, emulsions, microemulsions, gels, creams, granules, powders, tablets, pills, powders, liposomes, dendrimers and other nanoparticles (see for instance Baek et al., Methods Enzymol. 362, 240-9 (2003), Nigavekar et al., Pharm Res. 21(3), 476-83 (2004), microparticles, and suppositories. The optima form depends on the chosen mode of administration, the nature of the composition, and the therapeutic application. Formulations may include, for instance, powders, pastes, ointments, jellies, waxes, oils, lipids, lipid (cationic or anionic) containing vesicles, DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing may be appropriate in treatments and therapies in accordance with the present invention, provided that the antibody in the pharmaceutical composition is not inactivated by the formulation and the formulation is physiologically compatible and tolerable with the route of administration. See also for instance Powell et al., "Compendium of excipients for parenteral formulations" PDA J Pharm Sci Technol. 52, 238-311 (1998) and the citations therein for additional information related to excipients and carriers well known to pharmaceutical chemists.

The antibodies suitable for use according to the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See e.g., Sustained and Controlled Release Drug Delivery Systems, J. R. Robinson, ed., Marcel Dekker, Inc., New York, 1978.

To administer antibodies suitable for use according to the present invention by certain routes of administration, it may be necessary to coat the compound with, or co-administer the antibody with, a material to prevent its inactivation. For example, the antibody may be administered to a subject in an appropriate carrier, for example, liposomes, or a diluent. Liposomes include water-in-oil-in-water CGF emulsions as well as conventional liposomes (Strejan et al., J. Neuroimmunol. 7, 27 (1984)).

Depending on the route of administration, the antibody may be coated in a material to protect the compound from the action of acids and other natural conditions that may inactivate the compound. For example, the antibody may be administered to a subject in an appropriate carrier, for example, liposomes. Liposomes include water-in-oil-in-water CGF emulsions as well as conventional liposomes (Strejan et al., J. Neuroimmunol. 7, 27 (1984)).

In one embodiment, the antibodies suitable for use according to the present invention may be formulated to ensure proper distribution in vivo. To ensure that the therapeutic compounds of the present invention cross the BBB (if desired), they may be formulated, for example, in liposomes. For methods of manufacturing liposomes, see for instance U.S. Pat. No. 4,522,811, U.S. Pat. No. 5,374,548 and U.S. Pat. No. 5,399,331. The liposomes may comprise one or more moieties which are selectively transported into specific cells or organs, thus enhance targeted drug delivery (see for instance V. V. Ranade J. Clin. Pharmacol. 29, 685 (1989)). Exemplary targeting moieties include folate or biotin (see for instance U.S. Pat. No. 5,416,016), mannosides (Umezawa et al., Biochem. Biophys. Res. Commun. 153, 1038 (1988)), antibodies (P. G. Bloeman et al., FEBS Lett. 357, 140 (1995), M. Owais et al., Antimicrob. Agents Chemother. 39, 180 (1995)), surfactant protein A receptor (Briscoe et al., Am. J. Physiol. 1233, 134 (1995)), different species of which may comprise the pharmaceutical compositions of the present inventions, as well as components of the invented molecules, p120 (Schreier et al., J. Biol. Chem. 269, 9090 (1994)), see also K. Keinanen, M. L. Laukkanen, FEBS Lett. 346, 123 (1994) and J. J. Killion, I. J. Fidler, Immunomethods 4, 273 (1994).

The antibodies suitable for use according to the present invention may be formulated in liposomes, such as liposomes including a targeting moiety. The antibodies in the liposomes may be delivered by bolus injection to a site proximal to the desired area, e.g., the site of inflammation or infection, or the site of a tumor. The composition should be fluid to the extent that easy syringability exists. It should be stable under the conditions of manufacture and storage and should be preserved against the contaminating action of microorganisms such as bacteria and fungi.

The antibodies suitable for use according to the present invention may be formulated to prevent or reduce their transport across the placenta. This may be done by methods known in the art, e.g., by PEGylation of the compounds or by use of F(ab')$_2$ fragments. Further reference can be made to Cunningham-Rundles C et al., J Immunol Methods. 152, 177-190 (1992) and to Landor M., Ann Allergy Asthma Immunol 74, 279-283 (1995).

Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active antibody, use thereof in the pharmaceutical compositions is contemplated. Supplementary active compounds may also be incorporated into the compositions.

Pharmaceutical compositions for injection must typically be sterile and stable under the conditions of manufacture and storage. The composition may be formulated as a solution, microemulsion, liposome, or other ordered structure suitable to high drug concentration. The carrier may be a aqueous or nonaqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active antibody in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

The pharmaceutical composition may contain one antibody suitable for use according to the present invention or a combination of antibodies suitable for use according to the present invention.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the antibodies suitable for use according to the present invention may be determined by the persons skilled in the art. An exemplary, non-limiting range for a therapeutically effective amount of an antibody suitable for use according to the present invention is about 0.1-100 mg/kg, such as about 0.1-50 mg/kg, for example about 0.1-20 mg/kg, such as about 0.1-10 mg/kg, for instance about 0.5, about such as 0.3, about 1, or about 3 mg/kg.

A physician or veterinarian having ordinary skill in the art may readily determine and prescribe the effective amount of the pharmaceutical composition required. For example, the physician or veterinarian could start doses of the antibodies at levels lower than that required in order to achieve the desired therapeutic effect and gradually increase the dosage until the desired effect is achieved. In general, a suitable daily dose of an antibody suitable for use according to the present invention will be that amount of the compound which is the lowest dose effective to produce a therapeutic effect. Such an effective dose will generally depend upon the factors described above. Administration may be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for an antibody to be administered alone, it is preferable to administer the compound as a pharmaceutical composition as described above.

In one embodiment, the antibodies suitable for use according to the present invention may be administered by infusion in a weekly dosage of from 10 to 500 mg/m$^2$, such as of from 200 to 400 mg/m$^2$. Such administration may be repeated, e.g., 1 to 8 times, such as 3 to 5 times. The administration may be performed by continuous infusion over a period of from 2 to 24 hours, such as of from 2 to 12 hours.

In one embodiment, the antibodies suitable for use according to the present invention may be administered by slow continuous infusion over a long period, such as more than 24 hours, in order to reduce toxic side effects.

In one embodiment the antibodies suitable for use according to the present invention may be administered in a weekly dosage of from 250 mg to 2000 mg, such as for example 300 mg, 500 mg, 700 mg, 1000 mg, 1500 mg or 2000 mg, for up to 8 times, such as from 4 to 6 times. The administration may be performed by continuous infusion over a period of from 2 to 24 hours, such as of from 2 to 12 hours. Such regimen may be repeated one or more times as necessary, for example, after 6 months or 12 months. The dosage may be determined or adjusted by measuring the amount of compound of the present invention in the blood upon administration by for instance taking out a biological sample and using anti-idiotypic antibodies which target the antigen binding region of the antibodies suitable for use according to the present invention.

In one embodiment, the antibodies suitable for use according to the present invention may be administered by maintenance therapy, such as, e.g., once a week for a period of 6 months or more.

In one embodiment, the antibodies suitable for use according to the present invention may be administered by a regimen including one infusion of an antibody suitable for use according to the present invention followed by an infusion of an antibody suitable for use according to the present invention conjugated to a radioisotope. The regimen may be repeated, e.g., 7 to 9 days later.

As non-limiting examples, treatment according to the present invention may be provided as a daily dosage of an antibody suitable for use according to the present invention in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

The pharmaceutical compositions comprising an antibody suitable for use according to the present invention may also be administered in combination therapy, i.e., combined with other therapeutic agents relevant for the disease or condition to be treated. Such administration may be simultaneous, separate or sequential. For simultaneous administration the agents may be administered as one composition or as separate compositions, as appropriate. The present invention thus also provides methods for treating a disorder as described elsewhere, which methods comprise administration of an antibody suitable for use according to the present invention combined with one or more additional therapeutic agents as described below.

In one embodiment, the combination therapy may include administration of an antibody suitable for use according to the present invention together with high dose Ig I.V.

In one embodiment, the combination therapy may include administration of an antibody suitable for use according to the present invention together with at least one anti-inflammatory agent, at least one immunosuppressive and/or immunomodulatory agent, an enhancer of neuromuscular transmission, and/or such combination therapy may comprise the elimination of auto-antibodies by plasma exchange.

In one embodiment, the present invention provides a method for treating an antibody-mediated auto-immune disease or disorder in a subject, which method comprises administration of a therapeutically effective amount of an antibody suitable for use according to the present invention and at least one anti-inflammatory agent to a subject in need thereof.

In one embodiment, the present invention provides a method for treating or preventing myasthenia gravis, which method comprises administration of a therapeutically effective amount of an antibody suitable for use according to the present invention and at least one anti-inflammatory agent to a subject in need thereof.

In one embodiment, the present invention provides the use of an antibody suitable for use according to the present invention for the preparation of a pharmaceutical composition to be administered with at least one anti-inflammatory agent for treating or preventing myasthenia gravis.

In one embodiment, such an anti-inflammatory agent may be selected from a steroidal drug and a NSAID (nonsteroidal anti-inflammatory drug).

In one embodiment, such an anti-inflammatory agent may be selected from aspirin and other salicylates, Cox-2 inhibitors (such as rofecoxib and celecoxib), NSAIDs (such as ibuprofen, fenoprofen, naproxen, sulindac, diclofenac, piroxicam, ketoprofen, diflunisal, nabumetone, etodolac, oxaprozin, and indomethacin), anti-IL6R antibodies, anti-IL8 antibodies, anti-IL15 antibodies, anti-IL15R antibodies, anti-CD4 antibodies, anti-CD11a antibodies (e.g., efalizumab), anti-alpha-4/beta-1 integrin (VLA4) antibodies (e.g natalizumab), CTLA4-Ig for the treatment of inflammatory diseases, prednisolone, prednisone, disease modifying anti-rheumatic drugs (DMARDs) such as methotrexate, hydroxychloroquine, sulfasalazine, pyrimidine synthesis inhibitors (such as leflunomide), IL-1 receptor blocking agents (such as anakinra), TNF-α blocking agents (such as etanercept, infliximab, and adalimumab) and similar agents.

In one embodiment, the present invention provides a method for treating an antibody-mediated auto-immune disease or disorder in a subject, which method comprises administration of a therapeutically effective amount of an antibody suitable for use according to the present invention and at least one immunosuppressive and/or immunomodulatory agent to a subject in need thereof.

In one embodiment, the present invention provides a method for treating or preventing myasthenia gravis, which method comprises administration of a therapeutically effective amount of an antibody suitable for use according to the present invention and at least one immunosuppressive and/or immunomodulatory agent to a subject in need thereof.

In one embodiment, the present invention provides the use of an antibody suitable for use according to the present invention for the preparation of a pharmaceutical composition to be administered with at least one immunosuppressive and/or immunomodulatory agent for treating or preventing myasthenia gravis.

In one embodiment, such an immunosuppressive and/or immunomodulatory agent may be selected from cyclosporine, azathioprine, mycophenolic acid, mycophenolate mofetil, corticosteroids such as prednisone, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin, thymopentin, thymosin-α and similar agents.

In one embodiment, such an immunosuppressive and/or immunomodulatory agent may be selected from immunosuppressive antibodies, such as antibodies binding to p75 of the IL-2 receptor, or antibodies binding to for instance MHC, CD2, CD3, CD4, CD7, CD20, CD28, B7, CD40, CD45, IFNγ, TNF-α, IL-4, IL-5, IL-6R, IL-7, IL-8, IL-10, CD11a, or CD58, or antibodies binding to their ligands.

In one embodiment, such an immunosuppressive and/or immunomodulatory agent may be selected from soluble IL-15R, IL-10, B7 molecules (B7-1, B7-2, variants thereof, and fragments thereof), ICOS, and OX40, an inhibitor of a negative T cell regulator (such as an antibody against CTLA4) and similar agents.

In one embodiment, the antibodies suitable for use according to the present invention may be administered in combination with two or more immunosuppressive and/or immunomodulatory agents, such as in combination with prednisone and cyclosporine; prednisone, cyclosporine and azathioprine; or prednisone, cyclosporine and mycophenolate mofetil.

As described above, a pharmaceutical composition comprising an antibody suitable for use according to the present invention may be administered in combination therapy, i.e., combined with one or more agents relevant for the disease or condition to be treated either as separate pharmaceutical compositions or with a compound of the present invention coformulated with one or more additional therapeutic agents as described above. Such combination therapies may require lower dosages of the antibody and/or the co-administered agents, thus avoiding possible toxicities or complications associated with the various monotherapies.

In one embodiment, the present invention provides a method for treating an antibody-mediated auto-immune disease or disorder in a subject, which method comprises administration of a therapeutically effective amount of an antibody suitable for use according to the present invention and at least one enhancer of neuromuscular transmission to a subject in need thereof. Such enhancement may for instance be achieved by use of acetylcholinesterase (AChE) inhibitors, such as neostigmine and pyridostigmine, prolonging the action of acetyl choline, which helps improve neuromuscular transmission and increase muscle strength.

In one embodiment, the present invention provides an antibody suitable for use according to the present invention that is conjugated to an immunomodulator, such as an immunomodulating cytokine, stem cell growth factor, lymphotoxin (such as a TNF such as TNFα), or a hematopoietic factor. Examples of such molecules that may be useful as conjugates include IL-1, IL-2, IL-3, IL-6, IL-10, IL-12, IL-18, and IL-21, colony stimulating factors (such as granulocyte-colony stimulating factor (G-CSF) and granulocyte macrophage-colony stimulating factor (GM-CSF)), interferons (such as IFNα, IFNβ, and IFNγ) the stem cell growth factor designated "S1 factor," erythropoietin, and thrombopoietin, active fragments thereof, derivatives thereof, variants thereof, or a combination of any thereof.

The present invention also provides kits comprising a pharmaceutical composition of a compound of the present invention and instructions for use. The kit may further contain one or more additional therapeutic agents or one or more additional antibodies suitable for use according to the present invention. A kit of the present invention may also include diagnostic agents and/or other therapeutic agents. In one embodiment, a kit of the present invention includes an antibody suitable for use according to the present invention and a diagnostic agent that may be used in a diagnostic method for diagnosing the state or existence of a disorder treatable by administration of such antibodies. In one embodiment, the kit includes an antibody suitable for use according to the present invention in a highly stable form (such as in a lyophilized form) in combination with pharmaceutically acceptable carrier(s) that may be mixed with the highly stabile composition to form an injectable composition.

The following is a list of selected embodiments of the present invention.

Embodiment 1: Use of a multivalent complement activation deficient antibody for the preparation of a pharmaceutical composition for treatment of an antibody-mediated complement-dependent auto-immune disease or disorder in a subject, wherein said complement activation deficient antibody competes with one or more of the auto-antibodies involved in mediating the antibody-mediated complement-dependent auto-immune disease or disorder for binding to a target auto-antigen.

Embodiment 2: Use according to embodiment 1, wherein the multivalent complement activation deficient antibody is a bivalent antibody.

Embodiment 3: Use according to embodiment 1 or embodiment 2, wherein the multivalent complement activation deficient antibody is an IgG4 antibody.

Embodiment 4: Use according to any of embodiments 1 to 3, wherein the multivalent complement activation deficient antibody is capable of modulating the activity of the target auto-antigen.

Embodiment 5: Use according to any of embodiments 1 to 4, wherein the multivalent complement activation deficient antibody binds to the same epitope as an auto-antibody involved in mediating the antibody-mediated complement-dependent auto-immune disease or disorder.

Embodiment 6: Use according to any of embodiments 1 to 5, wherein the multivalent complement activation deficient antibody is derived from an auto-antibody involved in mediating the antibody-mediated complement-dependent auto-immune disease or disorder.

Embodiment 7: Use according to any of embodiments 1 to 6, wherein the heavy chain CDR3 region of the multivalent complement activation deficient antibody has a sequence identical to the heavy chain CDR3 region of an auto-antibody involved in the mediating the antibody-mediated complement-dependent auto-immune disease or disorder.

Embodiment 8: Use according to embodiment 7, wherein the heavy chain CDR1, CDR2 and CDR3 regions and the light chain CDR1, CDR2 and CDR3 regions of the multivalent complement activation deficient antibody have a sequence identical to the heavy chain CDR1, CDR2 and CDR3 regions and the light chain CDR1, CDR2 and CDR3 regions, respectively, of an auto-antibody involved in the mediating the antibody-mediated complement-dependent auto-immune disease or disorder.

Embodiment 9: Use according to any of embodiments 1 to 8, wherein the antibody is a human antibody.

Embodiment 10: Use according to any of embodiments 1 to 9, wherein the antibody-mediated complement-dependent auto-immune disease or disorder is myastenia gravis.

Embodiment 11: Use according to embodiment 10, wherein the target auto-antigen is the nicotinic acetylcholine receptor of the muscle.

Embodiment 12: Use according to embodiment 11, wherein the multivalent complement activation deficient antibody is derived from the patient derived anti-AChR Fab-637.

Embodiment 13. Use according to embodiment 11 or embodiment 12, wherein the multivalent complement activation deficient antibody has a $C_H$ CDR3 region of the same amino acid sequence as the CDR3 region of anti-AChR Fab-637.

Embodiment 14: Use according to embodiment 13, wherein the heavy chain CDR1, CDR2 and CDR3 regions and the light chain CDR1, CDR2 and CDR3 regions of the multivalent complement activation deficient antibody have a sequence identical to the heavy chain CDR1, CDR2 and CDR3 regions and the light chain CDR1, CDR2 and CDR3 regions, respectively, of anti-AChR Fab-637.

Embodiment 15: Use according to any of embodiments 11 to 14, wherein the multivalent complement activation deficient antibody comprises a $V_H$ region having the amino acid sequence of SEQ ID No: 2.

Embodiment 16: Use according to any of embodiments 11 to 15, wherein the multivalent complement activation deficient antibody comprises a $V_L$ region having the amino acid sequence of SEQ ID No: 4.

Embodiment 17: Use according to any of embodiments 11 to 16, wherein the multivalent complement activation deficient antibody competes with anti-AChR Fab-637 for binding to AChR.

Embodiment 18: Use according to any of embodiments 11 to 16, wherein the multivalent complement activation deficient antibody binds to the same epitope as anti-AChR Fab-637.

Embodiment 19: A method for treatment of an antibody-mediated complement-dependent auto-immune disease or disorder in a subject, which method comprises administration of a multivalent complement activation deficient antibody to a subject in need thereof, wherein said complement activation deficient antibody competes with one or more of the auto-antibodies involved in mediating the antibody-mediated complement-dependent auto-immune disease or disorder for binding to a target auto-antigen.

Embodiment 20: Method according to embodiment 19, wherein the multivalent complement activation deficient antibody is a bivalent antibody.

Embodiment 21: Method according to embodiment 19 or embodiment 20, wherein the multivalent complement activation deficient antibody is an IgG4 antibody.

Embodiment 22: Method according to any of embodiments 19 to 21, wherein the multivalent complement activation deficient antibody is capable of modulating the activity of the target auto-antigen.

Embodiment 23: Method according to any of embodiments 19 to 22, wherein the multivalent complement activation deficient antibody binds to the same epitope as an auto-antibody involved in mediating the antibody-mediated complement-dependent auto-immune disease or disorder.

Embodiment 24: Method according to any of embodiments 19 to 23, wherein the multivalent complement activation deficient antibody is derived from an auto-antibody involved in mediating the antibody-mediated complement-dependent auto-immune disease or disorder.

Embodiment 25: Method according to any of embodiments 19 to 24, wherein the heavy chain CDR3 region of the multivalent complement activation deficient antibody has a sequence identical to the heavy chain CDR3 region of an auto-antibody involved in the mediating the antibody-mediated complement-dependent auto-immune disease or disorder.

Embodiment 26: Method according to embodiment 25, wherein the heavy chain CDR1, CDR2 and CDR3 regions and the light chain CDR1, CDR2 and CDR3 regions of the multivalent complement activation deficient antibody have a sequence identical to the heavy chain CDR1, CDR2 and CDR3 regions and the light chain CDR1, CDR2 and CDR3 regions, respectively, of an auto-antibody involved in the mediating the antibody-mediated complement-dependent auto-immune disease or disorder.

Embodiment 27: Method according to any of embodiments 19 to 26, wherein the antibody is a human antibody.

Embodiment 28: Method according to any of embodiments 19 to 27, wherein the antibody-mediated complement-dependent auto-immune disease or disorder is myastenia gravis.

Embodiment 29: Method according to embodiment 28, wherein the target auto-antigen is the nicotinic acetylcholine receptor of the muscle.

Embodiment 30: Method according to embodiment 29, wherein the multivalent complement activation deficient antibody is derived from the patient derived anti-AChR Fab-637.

Embodiment 31: Method according to embodiment 29 or embodiment 30, wherein the multivalent complement activation deficient antibody has a $C_H$ CDR3 region of the same amino acid sequence as the CDR3 region of anti-AChR Fab-637.

Embodiment 32: Method according to embodiment 31, wherein the heavy chain CDR1, CDR2 and CDR3 regions and the light chain CDR1, CDR2 and CDR3 regions of the multivalent complement activation deficient antibody have a sequence identical to the heavy chain CDR1, CDR2 and CDR3 regions and the light chain CDR1, CDR2 and CDR3 regions, respectively, of anti-AChR Fab-637.

Embodiment 33: Method according to any of embodiments 29 to 32, wherein the multivalent complement activation deficient antibody comprises a $V_H$ region having the amino acid sequence of SEQ ID No: 2.

Embodiment 34: Method according to any of embodiments 29 to 33, wherein the multivalent complement activation deficient antibody comprises a $V_L$ region having the amino acid sequence of SEQ ID No: 4.

Embodiment 35: Method according to any of embodiments 29 to 34, wherein the multivalent complement activation deficient antibody competes with anti-AChR Fab-637 for binding to AChR.

Embodiment 36: Method according to any of embodiments 29 to 34, wherein the multivalent complement activation deficient antibody binds to the same epitope as anti-AChR Fab-637.

Embodiment 37: A multivalent complement activation deficient antibody, which competes with one or more auto-antibodies involved in mediating an antibody-mediated complement-dependent auto-immune disease or disorder for binding to a target auto-antigen.

Embodiment 38: A multivalent complement activation deficient antibody according to embodiment 37, wherein the multivalent complement activation deficient antibody is a bivalent antibody.

Embodiment 39: A multivalent complement activation deficient antibody according to embodiment 37 or embodiment 38, wherein the multivalent complement activation deficient antibody is an IgG4 antibody.

Embodiment 40: A multivalent complement activation deficient antibody according to any of embodiments 37 to 39, wherein the multivalent complement activation deficient antibody is capable of modulating the activity of the target auto-antigen.

Embodiment 41: A multivalent complement activation deficient antibody according to any of embodiments 37 to 40, wherein the multivalent complement activation deficient antibody binds to the same epitope as an auto-antibody involved in mediating the antibody-mediated complement-dependent auto-immune disease or disorder.

Embodiment 42: A multivalent complement activation deficient antibody according to any of embodiments 37 to 41, wherein the multivalent complement activation deficient antibody is derived from an auto-antibody involved in mediating the antibody-mediated complement-dependent auto-immune disease or disorder.

Embodiment 43: A multivalent complement activation deficient antibody according to any of embodiments 37 to 42, wherein the heavy chain CDR3 region of the multivalent complement activation deficient antibody has a sequence identical to the heavy chain CDR3 region of an auto-antibody involved in the mediating the antibody-mediated complement-dependent auto-immune disease or disorder.

Embodiment 44: A multivalent complement activation deficient antibody according to embodiment 43, wherein the heavy chain CDR1, CDR2 and CDR3 regions and the light chain CDR1, CDR2 and CDR3 regions of the multivalent complement activation deficient antibody have a sequence identical to the heavy chain CDR1, CDR2 and CDR3 regions and the light chain CDR1, CDR2 and CDR3 regions, respectively, of an auto-antibody involved in the mediating the antibody-mediated complement-dependent auto-immune disease or disorder.

Embodiment 45: A multivalent complement activation deficient antibody according to any of embodiments 37 to 44, wherein the antibody is a human antibody.

Embodiment 46: A multivalent complement activation deficient antibody according to any of embodiments 37 to 45, wherein the antibody-mediated complement-dependent auto-immune disease or disorder is myastenia gravis.

Embodiment 47: A multivalent complement activation deficient antibody according to embodiment 46, wherein the target auto-antigen is the nicotinic acetylcholine receptor of the muscle.

Embodiment 48: A multivalent complement activation deficient antibody according to embodiment 47, wherein the multivalent complement activation deficient antibody is derived from the patient derived anti-AChR Fab-637.

Embodiment 49: A multivalent complement activation deficient antibody according to embodiment 47 or embodiment 48, wherein the multivalent complement activation deficient antibody has a $C_H$ CDR3 region of the same amino acid sequence as the CDR3 region of anti-AChR Fab-637.

Embodiment 50: A multivalent complement activation deficient antibody according to embodiment 49, wherein the heavy chain CDR1, CDR2 and CDR3 regions and the light chain CDR1, CDR2 and CDR3 regions of the multivalent complement activation deficient antibody have a sequence identical to the heavy chain CDR1, CDR2 and CDR3 regions and the light chain CDR1, CDR2 and CDR3 regions, respectively, of anti-AChR Fab-637.

Embodiment 51: A multivalent complement activation deficient antibody according to any of embodiments 47 to 50, wherein the multivalent complement activation deficient antibody comprises a $V_H$ region having the amino acid sequence of SEQ ID No: 2.

Embodiment 52: A multivalent complement activation deficient antibody according to any of embodiments 47 to 51, wherein the multivalent complement activation deficient antibody comprises a $V_L$ region having the amino acid sequence of SEQ ID No: 4.

Embodiment 53: A multivalent complement activation deficient antibody according to any of embodiments 47 to 52, wherein the multivalent complement activation deficient antibody competes with anti-AChR Fab-637 for binding to AChR.

Embodiment 54: A multivalent complement activation deficient antibody according to any of embodiments 47 to 52, wherein the multivalent complement activation deficient antibody binds to the same epitope as anti-AChR Fab-637.

All patents, pending patent applications and other publications cited herein are hereby incorporated by reference in their entirety.

The present invention is further illustrated by the following examples which should not be construed as further limiting.

EXAMPLES

Example 1

Generation of IgG1-637 and IgG4-637
Oligonucleotide Primers and PCR Amplification Oligonucleotide primers were synthesized and quantified by Isogen Bioscience (Maarssen, The Netherlands). Primers were dissolved in $H_2O$ to 100 pmol/μl and stored at −20° C. A summary of all PCR and sequencing primers is tabulated in FIG. 1. For PCR, PfuTurbo® Hotstart DNA polymerase (Stratagene, Amsterdam, The Netherlands) was used according to the manufacturer's instructions. Each reaction mix contained 200 μM mixed dNTPs (Roche Diagnostics, Almere, The Netherlands), 6.7 pmol of both the forward and reverse primer, 100 ng of genomic DNA or 1 ng of plasmid DNA and 1 unit of PfuTurbo® Hotstart DNA polymerase in PCR reaction buffer (supplied with polymerase) in a total volume of 20 μl. PCR reactions were carried out with a TGradient Thermocycler 96 (Whatman Biometra, Goettingen, Germany) using a 32-cycle program: denaturing at 95° C. for 2 min; 30 cycles of 95° C. for 30 sec, a 60-70° C. gradient (or another specific annealing temperature) for 30 sec, and 72° C. for 3 min; final extension at 72° C. for 10 min. If appropriate, the PCR mixtures were stored at 4° C. until further analysis or processing.

Agarose Gel Electrophoresis

Agarose gel electrophoresis was performed according to Sambrook (Sambrook J. and Russel, D. V. Molecular Cloning: A Laboratory Manual, 3nd Ed., Cold Spring Harbor, 2000) using gels of 50 ml, in 1×Tris Acetate EDTA buffer. DNA was visualized by the inclusion of ethidium bromide in the gel and observation under UV light. Gel images were recorded by a CCD camera and an image analysis system (GeneGnome; Syngene, via Westburg B. V., Leusden, The Netherlands).

Analysis and Purification of PCR Products and Enzymatic Digestion Products

Purification of desired PCR fragments was carried out using a MinElute PCR Purification Kit (Qiagen, via Westburg, Leusden, The Netherlands; product #28006), according to the manufacturer's instructions. Isolated DNA was quantified by UV spectroscopy and the quality was assessed by agarose gel electrophoresis.

Alternatively, PCR or digestion products were separated by agarose gel electrophoresis (for instance when multiple fragments were present) using a 1% Tris Acetate EDTA agarose gel. The desired fragment was excised from the gel and recovered using the QIAEX II Gel Extraction Kit (Qiagen; product #20051), according to the manufacturer's instructions.

Quantification of DNA by UV Spectroscopy

Optical density of nucleic acids was determined using a NanoDrop ND-1000 Spectrophotometer (Isogen Life Science, Maarssen, The Netherlands) according to the manufacturer's instructions. The DNA concentration was measured by analysis of the optical density (OD) at 260 nm (one $OD_{260nm}$ unit/cm=50 μg/ml). For all samples, the buffer in which the nucleic acids were dissolved was used as a reference.

Restriction Enzyme Digestions

Restriction enzymes and supplements were obtained from New England Biolabs (Beverly, Mass., USA) or Fermetas (Vilnius, Lithuania) and used according to the manufacturer's instructions.

DNA (100 ng) was digested with 5 units of enzyme(s) in the appropriate buffer in a final volume of 10 μl (reaction volumes were scaled up as appropriate). Digestions were incubated at the recommended temperature for a minimum of 60 min. For fragments requiring double digestions with restriction enzymes which involve incompatible buffers or temperature requirements, digestions were performed sequentially. If necessary digestion products were purified by agarose gel electrophoresis and gel extraction.

Ligation of DNA Fragments

Ligations of DNA fragments were performed with the Quick Ligation Kit (New England Biolabs) according to the manufacturer's instructions. For each ligation, vector DNA was mixed with approximately three-fold molar excess of insert DNA.

Transformation of E. coli

Plasmid DNA (1-5 μl of DNA solution, typically 2 μl of DNA ligation mix) was transformed into One Shot DH5α-T1$^R$ or MACH-1 T1$^R$ competent E. coli cells (Invitrogen, Breda, The Netherlands; product #12297-016) using the heatshock method, according to the manufacturer's instructions. Next, cells were plated on Luria-Bertani (LB) agar plates containing 50 μg/ml ampicillin. Plates were incubated for 16-18 hours at 37° C. until bacterial colonies became evident.

Screening of Bacterial Colonies by PCR

Bacterial colonies were screened for the presence of vectors containing the desired sequences via colony PCR using the HotStarTaq Master Mix Kit (Qiagen; product #203445) and the appropriate forward and reverse primers. Selected colonies were lightly touched with a 20 μl pipette tip and touched briefly in 2 ml LB for small scale culture, and then resuspended in the PCR mix. PCR was performed with a TGradient Thermocycler 96 using a 35-cycle program: denaturation at 95° C. for 15 min; 35 cycles of 94° C. for 30 sec, 55° C. for 30 sec and 72° C. for 2 min; followed by a final extension step of 10 min at 72° C. If appropriate, the PCR mixtures were stored at 4° C. until analysis by agarose gel electrophoresis.

Plasmid DNA Isolation from E. coli Culture

Plasmid DNA was isolated from E. coli cultures using the following kits from Qiagen (via Westburg, Leusden, The Netherlands), according to the manufacturer's instructions. For bulk plasmid preparation (50-150 ml culture), either a HiSpeed Plasmid Maxi Kit (product #12663) or a HiSpeed Plasmid Midi Kit (product #12643) was used. For small scale plasmid preparation (±2 ml culture) a Qiaprep Spin Miniprep Kit (product #27106) was used and DNA was eluted in 50 µl elution buffer (supplied with kit).

DNA Sequencing

Plasmid DNA samples were sent to AGOWA (Berlin, Germany) for sequence analysis. Sequences were analyzed using Vector NTI advanced software (Informax, Oxford, UK).

Transient Expression in HEK-293F Cells

Freestyle™ 293-F (a HEK-293 subclone adapted to suspension growth and chemically defined Freestyle medium, e. g. HEK-293F) cells were obtained from Invitrogen and transfected according to the manufacturer's protocol using 293fectin (Invitrogen).

Generation of IqG1-637

The light chain and the Fd coding sequences of Fab-637 (Graus, Y F et al., J Immunol 158, 1919 (1997)) were cloned from the pComb3 bacterial expression vector to the mammalian vector pIgG1 , which contains the sequence for the human IgG1 Fc. The Fd sequence was cloned using XhoI and BstEII, XbaI and SacI were used for the light chain sequence. The resulting plasmid was named pIgG1-637. In pIgG1-637, the expression of each chain was regulated by a human cytomegalovirus promoter/enhancer (hCMV P/E) element, the secretion of the H chain by a mouse H chain leader peptide and the secretion of the L chain by a mouse κ leader peptide. CHO-K1 cells (ATCC Number CCL-61) were cultured in HAM's F12 (Gibco/Invitrogen), supplemented with 10% fetal bovine serum (Bodinco, Alkmaar, The Netherlands). Cells were transfected with pIgG1-637 using Lipofectin (Gibco/Invitrogen), according to the manufacturer's manual. Transfected cells were adapted to suspension culture. Monoclonal stable transfected cells were obtained by auxotroph-based selection and limiting dilution. The highest producer was selected for large-scale production. A hollow fibre culture yielded 558 mg protein G-purified IgG1-637.

Generation of IgG1-637 Flag

A flag tag was added to the carboxy-terminus of the IgG1-637 heavy chain for competition experiments. A fragment of 3268 bp containing the stop codon of the HC was subcloned from pIgG1-637 to pBluescribe IIKS+ (Invitrogen) using XhoI and SalI resulting in the plasmid pBS-HC. A NheI restriction site replacing the stop codon was inserted by mutagenesis using the primer ON-NheI-mutm (FIG. 1) and the complementary primer with the QuickChange XL Site-directed Mutagenesis Kit (Stratagene, La Jolla, Calif., USA), according to the manufacturer's manual, resulting in the vector pBS-HC-NheI. The region between the stop codon and the SalI site of pBS-HC was amplified by PCR using the forward primer ON-NheI-Flag (FIG. 1). The primer ON-NheI-Flag added a NheI site and the coding sequence of the flag tag (DYKDDDDK) followed by a stop codon to the PCR product. The fragment was purified and cloned into pBS-HC-NheI with NheI and SalI resulting in the plasmid pBS-HC-NheI-flag The XhoI-SgrAI fragment from pBS-HC-NheI-flag was subcloned into pIgG1-637.

Construction of pConLamMG: A Vector for Production of the Light Chain of IgG4-637

The $V_L$ coding region of anti-MG was amplified by PCR from pIgG1-637, using the primers MGLCexfor and RACElambda1 (FIG. 1), introducing suitable restriction sites for cloning into pConLam2 and an ideal Kozak sequence. The PCR product and the pConLam2 (Lonza Biologics) vector were digested with HindIII and AvrII and purified from gel. The $V_L$ fragment and the pConLam2HindIII-AvrII fragment were ligated and transformed into competent DH5α-T1$^R$ cells. 10 colonies were checked by colony PCR (using primers pConG1seq1 and pEE13.4seqrev (FIG. 1) and 8 were found to containing the correct insert size. From two positive colonies 50 ml cultures were grown. Plasmid DNA was isolated and the constructs were checked by sequence analysis of the insert and found to be correct. One clone was chosen for further propagation and named pConLamMG.

Construction of pTomG4; A Vector for the Expression of Variable Heavy Chain Regions of Human IgG with the Constant Region of Human IgG4

Genomic DNA was isolated from a blood sample of a volunteer and used as a template in a PCR with primers IgG4gene2f and IgG4gene2r (FIG. 1), amplifying the complete genomic constant region of the heavy chain of IgG4 and introducing suitable restriction sites for cloning into the mammalian expression vector pEE6.4 (Lonza Biologics). The PCR fragment was purified and cloned into pEE6.4. For this the PCR product was digested with HindIII and EcoRI, followed by heat inactivation of the restriction enzymes. The pEE6.4 vector was digested HindIII and EcoRI, followed by heat inactivation of the restriction enzymes and dephosphorylation of the vector fragment with shrimp alkaline phosphatase, followed by heat inactivation of the phosphatase. The IgG4 fragment and the pEE6.4HindIII/EcoRI dephosphorylated vector were ligated and transformed into competent MACH1-T1$^R$ cells (Invitrogen). Three clones were grown in LB and plasmid DNA was isolated from a small culture (1.5 ml). Restriction digestion revealed a pattern consistent with the cloning of the IgG4 fragment in the pEE6.4 vector. Plasmid DNA from two clones was transformed in DH5α-T1$^R$ E. coli and plasmid DNA was isolated and the constructs were checked by sequence analysis of the insert and one clone was found to be identical to a genomic IgG4 clone from the Genbank database, apart from some minor differences in introns. These differences are presumably either polymorphisms or PCR-introduced changes in the Genbank sequence. The plasmid was named pTomG4.

Construction of pTomG4MG: A Vector for the Production of the Heavy Chain of IgG4-637

The $V_H$ coding region of anti-MG was amplified by PCR from pIgG1637, using the primers MGHCexfor and MGH-Cexrev (FIG. 1), introducing suitable restriction sites for cloning into pTomG4 and an ideal Kozak sequence. The PCR fragment was gel purified and cloned into pTomG4. For this the PCR product was digested with HindIII and Esp3I and gel purified. The pTomG4 vector was digested with HindIII and Bsp120I and the vector fragment was isolated from gel. The $V_H$ fragment and the pTomG4HindIII-Bsp120I fragment were ligated and transformed into competent DH5α-T1$^R$ cells. 12 colonies were checked by colony PCR (using primers pConG1seq1 and pEE13.4seqrev) and found to be all containing the correct insert size. From two positive colonies 50 ml cultures were grown. Plasmid DNA was isolated and the constructs were checked by sequence analysis of the insert and found to be correct apart from 2 nucleotide substitutions which were different from the sequence which was provided with the pIgG1-637 plasmid. These two substitutions were silent and it was concluded that they were the result from mistakes in the original sequence but without consequence. A selected clone was named pTomG4MG.

Stable Co-Transfection of pTomG4MG and pConLamMG in CHO-K1SV Cells for the Production of IqG4-637

The pTomG4MG and pConLamMG vectors were linearized with SalI and purified. The linearized vectors were transfected in CHO-K1SV cells (Lonza Biologics), by nucleofection using a nucleofector (Amaxa), according to the manufacturer's instructions. 50 µM MSX in glutamine deficient medium was used to select for stable integration of the vectors and a clone was selected which produces the highest amount of IgG4. The final clone was grown in CD-CHO (Invitrogen) as a 5 l batch culture in spinner flasks.

Electron microscopy. Intercostal muscle biopsy fragments of 3 mm diameter were submerged in fixation buffer (2.5% glutaraldehyde in 0.1 M phosphate buffer pH=7.4) and post-fixed with 1% osmiumtetroxide in 0.1 phosphate buffer, pH 7.4, dehydrated through a graded ethanol series and embedded in epoxy resin (Glycid ether 100, Serva, Heidelberg, Germany). Endplates were located in toluidine blue-stained semi-thin sections. Ultra-thin sections from selected areas were contrasted with uranyl acetate and lead citrate and analyzed with a Philips CM 100 electron microscope.

Example 2

Purification of IgG4-637 Antibody

IgG4-637 was purified from tissue culture supernatants. First the supernatants were filtered over 0.20 µM dead-end filter. Then, the supernatant was loaded on a 5 ml Protein A column (rProtein A FF, Amersham Bioscience) and eluted with 0.1 M citric acid-NaOH, pH 3. The eluate was immediately neutralized with 2 M Tris-HCl, pH 9 and dialyzed overnight to 12.6 mM sodium phosphate, 140 mM NaCl, pH 7.4 (B. Braun, Oss, The Netherlands). After dialysis samples were sterile filtered over 0.20 µM dead-end filter.

Samples were tested on concentration of IgG by nephelometry and absorbance at 280 nm.

Example 3

Non-Reduced SDS-PAGE Analysis of IgG4-637 Antibody

After purification as described in Example 2, IgG4-637 was analysed on non-reducing SDS-PAGE. The Bis-Tris electrophoresis method used is a modification of the Laemmli method (Laemmli, UK, Nature 227, 680 (1970)), where the samples were run at neutral pH. The SDS-PAGE gels were stained with Coomassie and digitally imaged using the GeneGenius (Synoptics, Cambridge, UK).

As can be seen in FIG. 2, IgG4-637 is shown to have, besides the major band representing the tetrameric IgG4 molecule, a substantial amount of half-molecules (i.e. one heavy chain, one light chain) as has been described in literature (Schuurman, J. et al., Mol Immunol 38, 1 (2001), Angal, S. et al., Mol Immunol 30, 105 (1993), Colcher, D. et al., Cancer Res 49, 1738 (1989), King, D J et al., Biochem J 281(Pt 2), 317 (1992), Petersen, J G et al., J Biol Chem 249, 5633 (1974)).

Example 4

Analysis of Complement Binding of IgG1-637 and IgG4-637 Antibody

The complement binding of IgG1-637, IgG4-637 and polyclonal isotype controls were tested by ELISA. In short, microtiter ELISA plates (Greiner, Germany) were coated overnight at room temperature with the test antibodies, serially diluted from 10 µg/ml to 0.15 µg/ml in PBS. Plates were emptied and wells were blocked with 200 µl C1q buffer (PBS supplemented with 0.1% w/v gelatine and 0.05% v/v Tween-20) per well for the C1q ELISA, and with 200 µl PBS/BSA buffer (PBS supplemented with 1% BSA) per well for C3 and C4 ELISA. ELISAs were incubated at room temperature for 60 minutes. Subsequently, plates were emptied. For the C3 and C4 ELISAs the wells were washed 3 times with 200 µl PBST (PBS supplemented with 0.05% (v/v) tween-20). Subsequently, for C1q ELISA, wells were incubated with 2 µg/mi human C1q (Quidel, San Diego, Calif., USA, A400) in C1q buffer (100 µl/well, 37° C., 1 h). For the C4 and C4 ELISA, the wells were incubated with 100 µl human pooled serum 1:33 diluted in TBS buffer (15 mM Tris pH 7.45, 145 mM NaCl, 10 mM CaCl2, 5 mM MgCl2, 0.2% BSA, 1 hr 37° C.). After washing the plates (3×) with PBST for the C3 and C4 ELISA and C1q buffer for the C1q ELISA, for the C1q ELISA wells were incubated with rabbit anti-human C1q (DAKO, Glostrup, Denmark, A0136), diluted in C1q buffer (1:1000, 100 µl/well, room temperature, 1 h). For the C3 ELISA, the plates were incubated with mouse anti-human C3, (DAKO, clone HAV3-4, M0836), 1:100 diluted in PBST/BSA (PBST supplemented with 0.1% BSA), (1:100, 100 µl/well, room temperature, 1 hr). For the C4 ELISA the plates were incubated with mouse anti-human C4 (Brunschwig, Basel, Switzerland, Hyb 162-02) diluted in PBST/BSA (1:2000, 100 µl/well, room temperature, 1 hr). After washing the plates (3×) with PBST for the C3 and C4 ELISA and C1q buffer for the C1q ELISA, for the C1q ELISA wells were incubated with HRP-conjugated swine anti-rabbit IgG-Fc (DAKO, P0399) diluted in ELISA buffer (1:2500, 100 µl/well, room temperature, 1 h). For the C3 and C4 ELISA, wells were incubated with HRP conjugated rabbit anti-mouse IgG (Jackson Immuno Research, Westgrove, USA, 315-035-046), diluted in PBST 0.1% BSA, 100 µl/well, 1 hr room temperature), Thereafter, plates were washed thrice and assays were developed with freshly prepared 1 mg/ml ABTS solution (ABTS: 2,2'-azino-bis[3-ethylbenzthiazoline-6-sulfonic acid]; 2 tablets of 5 mg in 10 ml ABTS buffer, Boehringer Mannheim, Ingelheim, Germany) at room temperature in the dark for 30 minutes. Absorbance was measured at 405 nm in an ELISA plate reader (Biotek Instruments Inc., Winooski, USA). To analyze, if complement activation by human IgG isotypes depends on the source of the complement, both human and rhesus serum were tested.

Figure 3:
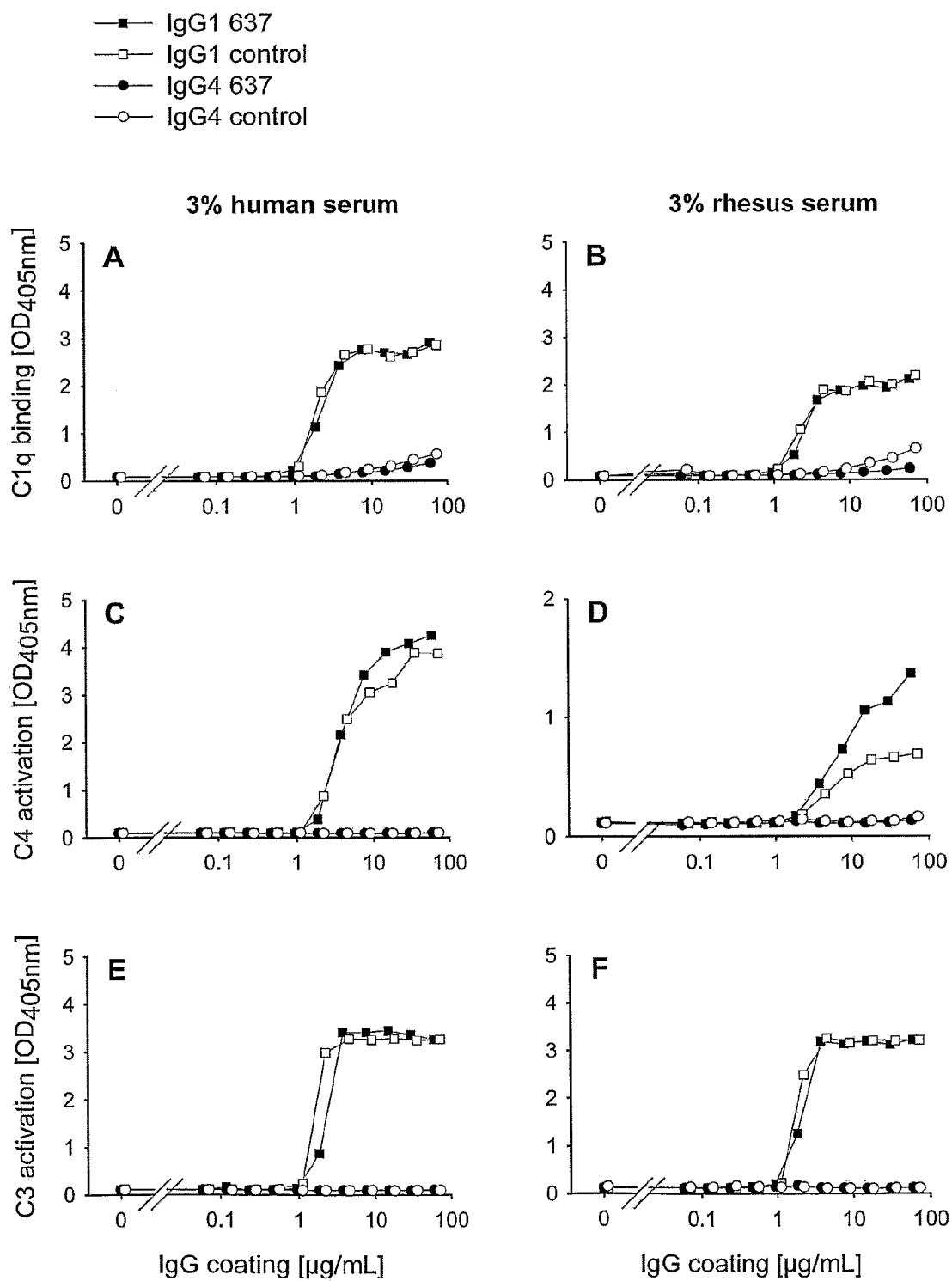
FIG. 3: C1q binding and complement activation of IgG1-637 (closed squares), IgG4-637 (closed circles) and human IgG1 and IgG4 isotype controls (corresponding open symbols). The complement activation was determined by ELISA at different stages: (A and B) C1q binding; (C and D) C4b deposition; (E and F) C3b deposition. Human serum was used in A, C and E and rhesus serum in B, D and F.

As shown in FIG. 3, the purified IgG1-637 bound and activated complement as efficient as polyclonal human IgG1. The IgG4-637 and the polyclonal IgG4 control did not bind or activate complement.

Example 5

Analysis of Specificity and Binding Properties of IqG1-637, IgG1-637-Flag and IgG4-637 Antibody Determination of Specificity by Radioimmunoassay The specificity of IgG1-637, IgG1-637-flag and IgG4-637 was determined by radioimmunoassay (Lindstrom, J B et al., Methods Enzymol 74(Pt C), 432 (1981)), using human AChR (prepared from the human TE671 rhabdomyosarcoma cell line (Luther, M A et al., J Neurosci 9, 1082 (1989)), Torpedo AChR (prepared from Torpedo californica), hybrid AChR (human α1 subunit and Torpedo β, γ and δ subunits (Loutrari, H et al., Clin Exp Immunol 109, 538 (1997)) or recombinant human α1-210 peptide. The AChR was labelled with $^{125}$I-labeled α-bungarotoxin (Amersham) and incubated with different sample concentrations and human serum as co-precipitant. Human IgG was precipitated by incubation with polyclonal goat anti-human Ig, for 4 h at 4° C. and centrifugation at 15000 g for 10 min. The pellets were washed twice with 0.5% Triton X-100 PBS and measured in a γ-counter.

Figure 4:
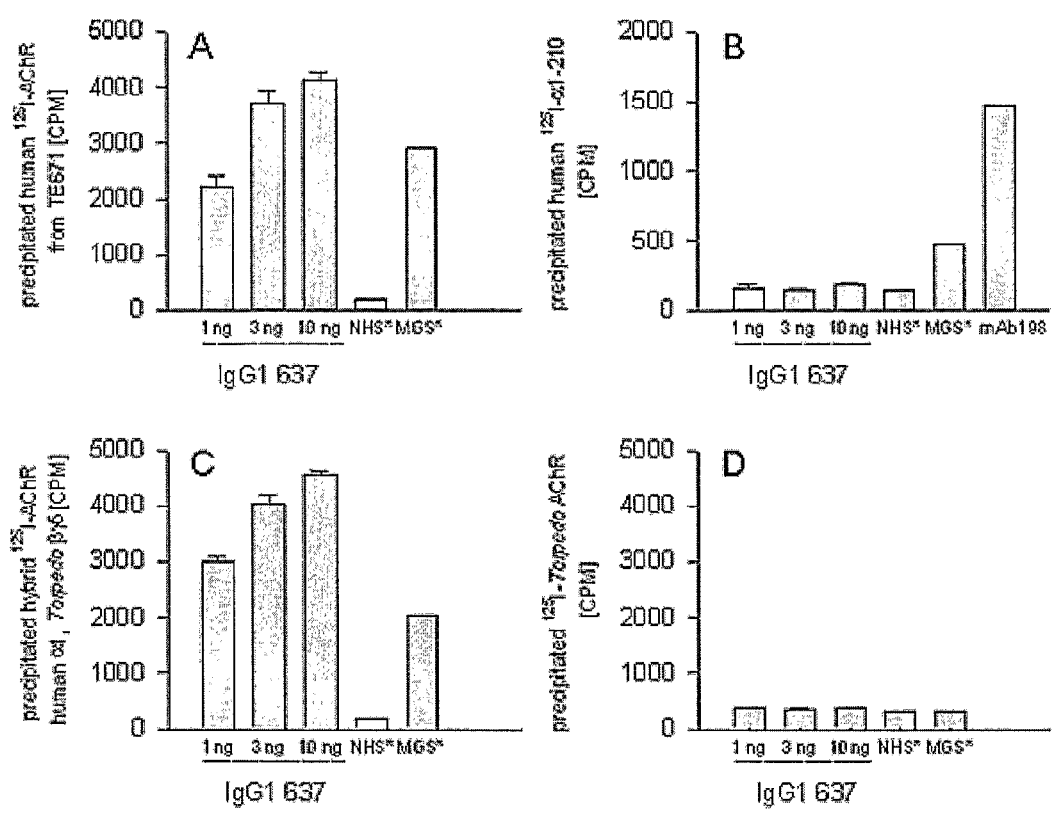
FIG. 4: Specificities of the human anti-AChR mAb IgG1-637 determined by radioimmunoassay. (A) IgG1-637 binds to the human AChR from membrane extracts from TE671 cells. (B) There was no binding to the recombinant peptide α1-210, representing the extracellular part of the alpha subunit of the human AChR. (C) IgG1-637 binds to a recombinant hybrid AChR from membrane extracts of cells expressing the human α1 and the Torpedo βγδ subunits. (D) IgG1-637 does not bind to the wildtype Torpedo AChR. Also control MG sera did not crossreact with Torpedo AChR. *NHS—normal human serum; *MGS—serum from myasthenia gravis patients.

IgG1-637 bound to human AChR from membrane extracts of TE671 cells (FIG. 4A). The specificity of Fab-637 for the human alpha subunit of the AChR was preserved in the full size IgG1-637: it bound to recombinant human/Torpedo hybrid AChR (FIG. 4C), with the human α1 and the Torpedo βγδ subunits, but did not bind to wildtype Torpedo AChR (FIG. 4D). IgG1-637 also did not bind to the recombinant human α1-210 peptide (FIG. 4B), confirming the specificity for a conformational epitope. Other than the human AChR, IgG1-637 bound to AChR of rhesus monkeys, but not common marmoset monkeys, as found by immunohistochemical staining of primate muscles.

Figure 5:
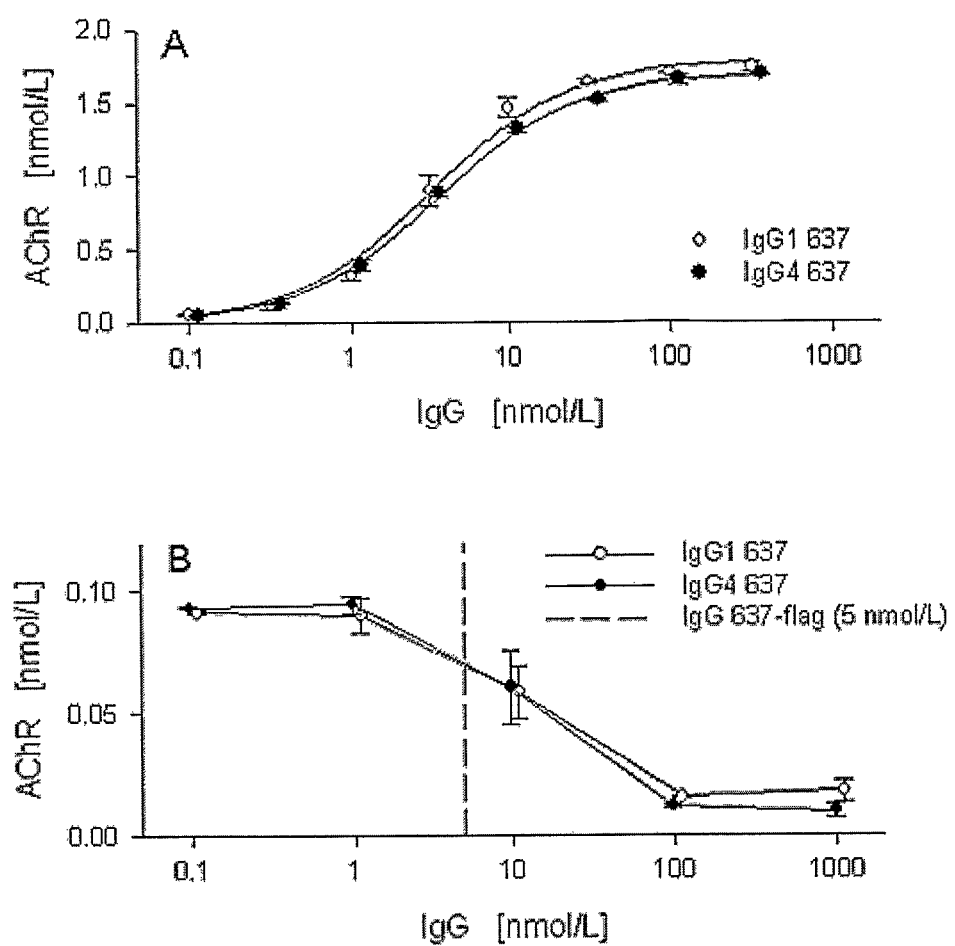
FIG. 5: Binding of IgG1-637 and IgG4-637 to AChR from TE671 cells measured by radioimmunoassay. (A) Binding curves using dilutions of antibody and a fixed amount of AChR. Data were fitted to a rectangular hyperbola. The Kd is 1.7 nmol/L for both antibodies. (B) Competition of IgG1-637 with IgG4-637. Fixed amounts of AChR and IgG1-637-flag were incubated with competitor antibody. Flag tagged antibodies were specifically precipitated with mouse anti flag mAb M2. The binding of IgG1-637-flag was reduced equally by IgG1-637 and IgG4-637, if the concentrations exceeded their Kd.

The binding of IgG1-637 and IgG4-637 to human AChR was compared by a radioimmunoassay using iodinated bungarotoxin. The results in FIG. 5A show that both antibodies bind the human AChR with the same dissociation constant of approximately 1.7 nM.

Measurement of Binding to AChR Using Flow Cytometry

The binding of IgG1-637 to AChR expressed on TE671 or MITC cells (Wakkach, A. et al., Am J Pathol 155, 1229 (1999)) was measured by flow cytometry (FACSCalibur, Becton Dickinson Immunocytometry Systems, Mountain View, Calif., USA). Trypsinized cells were incubated with sample antibody and subsequently with FITC-conjugated goat anti-human Ig. The signal was amplified by EAS Kit (Flow-Amp Systems, Cleveland, USA). For detection of IgG1-637 binding to cytoplasmic AChR, cells were permeabilised with paraformaldehyde solution (2%).

Figure 6:
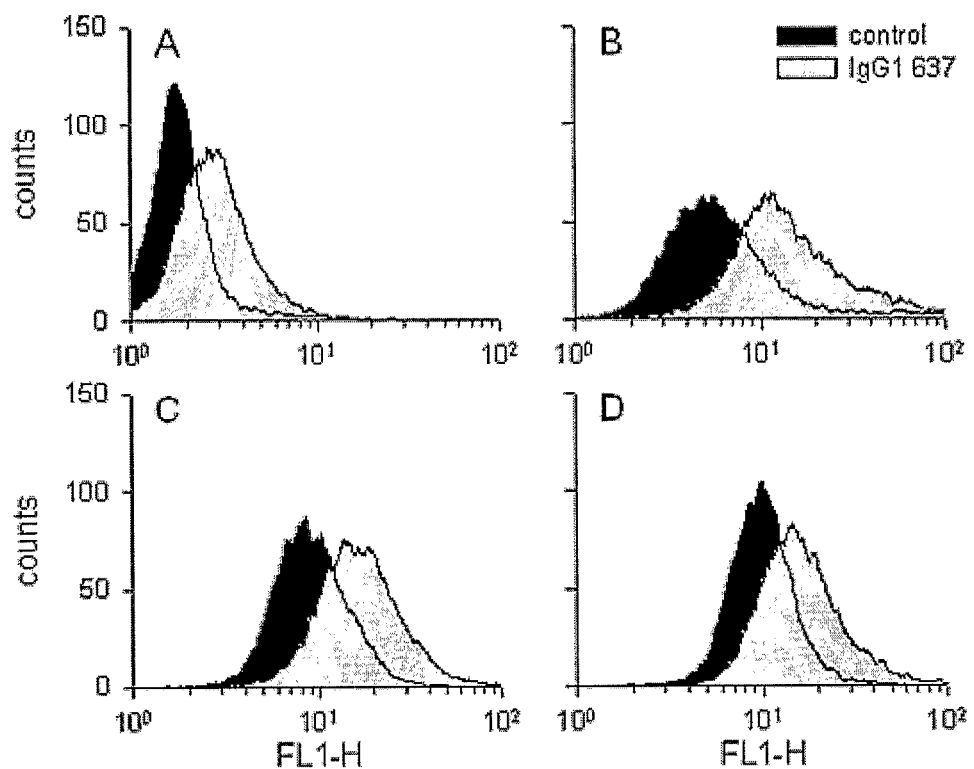
FIG. 6: FACS analysis of IgG1-637. The human fetal muscle AChR expressing cell line TE671 was incubated with IgG1-637. Shown are the FL-1 intensities of subsequent staining with goat anti-human Ig FITC (A) or goat anti-human Ig FITC followed by signal amplification using the EAS Kit (B) (specific staining is shown in grey, black indicates the background staining). In (C) staining of permeabilised TE671 cells is shown. The human fetal and adult muscle AChR-expressing cell line MITC was incubated with IgG1-637 and stained with goat anti-human Ig FITC (D).

As can be seen in FIG. 6, IgG1-637 bound to intact TE671 and MITC cells, and to cytoplasmic AChR.

Measurement of Competition of IgG1-637 and IgG4-637 with IgG1-637-Flag in a Radioimmunoassay The competition of IgG4-637 and IgG1-637 with IgG1-637-flag was measured by radioimmunoassay using AChR from TE671 cell membrane extract. For this purpose different concentrations of IgG1-637 or IgG4-637 were pre-mixed with a fixed concentration of IgG1-637-flag, which was then incubated with human AChR labelled with $^{125}$I-α-bungarotoxin: Approximately 2 nmol of AChR were labelled with an excess of $^{125}$I-α-bungarotoxin and incubated for 8 h at 4° C. with 5 nmol IgG1-637-flag and different concentrations of IgG1-637 or IgG4-637 in a total volume of 75 μL. To each sample 2 μg mouse anti-FLAG M2 (Sigma) and 1 μl normal mouse serum (co-precipitant) were added and incubated at for another 12 h. The mouse antibodies were precipitated with 100 μL preabsorbed goat serum containing polyclonal goat anti mouse antibodies for 4 h at 4° C. The preabsorbed goat serum was prepared by incubation with human serum (1:1 (v/v)) at 37° C. for 2 h and cleared by centrifugation and filter-sterilisation. The samples were then centrifuged and processed as described above.

As can be seen in FIG. 5B, the precipitation of the flag tagged antibody was decreased dose-dependently, to approximately 50% at two fold excess of IgG1-637 or IgG4-637. This confirms the similarity of the binding properties of IgG1-637 and IgG4-637.

Antigenic Modulation of AChR

The enhanced degradation of surface AChR of TE671 cells by antibodies was measured by incubating confluent cells with serial dilutions of IgG1-637, IgG4-637 and human IVIg. Cells were incubated for 3 hours with antibodies diluted in DMEM supplemented with 40 μM cycloheximide. The remaining AChR was labelled with an excess of 125I-labeled α-bungarotoxin in the same medium without antibodies for one hour and washed 3 times with PBS. Unspecific binding was measured by incubating cells with unlabelled bungarotoxin prior to incubation with $^{125}$I-α-bungarotoxin.

Figure 7:
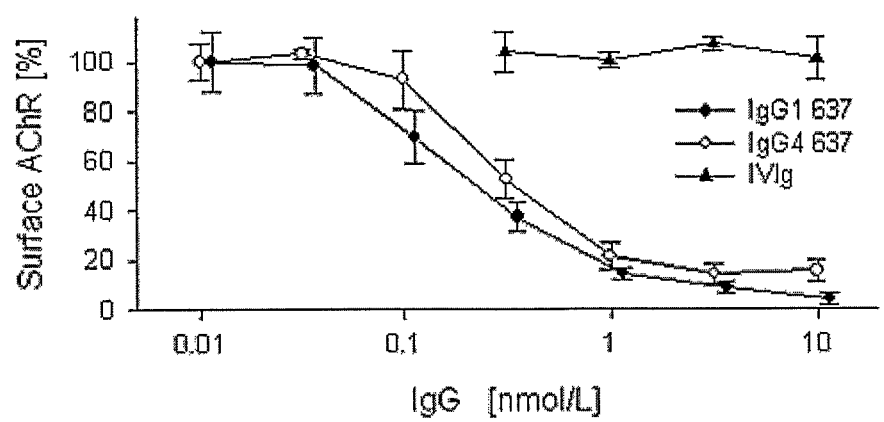
FIG. 7: Antigenic modulation of surface AChR of TE671 cells. Confluent cells were incubated with cycloheximide and antibodies. IgG1-637 and IgG4-637 equally reduced surface AChR levels, while human immunoglobulin (IVIg) had no effect compared to medium without antibodies.

FIG. 7 shows that both IgG1-637 and IgG4-637 were capable of modulating the antigen by reducing the AChR levels on the cell surface of cultured TE671 cells. Control immunoglobulin from human IVIg preparations had no effect on the AChR levels.

Example 6

Establishment of a Passive Transfer Model for MG Using IgG1-637

In order to test the ability of IgG4-637 to compete with IgG1-637 in vivo, an animal model was established. Since IgG1-637 only binds to the human and macaque AChR, a passive transfer experiment with IgG1-637 in rhesus monkeys (*Macaca mulatta*) was performed.

Animal experiments were performed at the Biomedical Primate Research Center (Rijswijk, The Netherlands) with permission of the Committee on Animal Welfare (DEC), according to Dutch governmental rules. First, the binding of IgG1-637 to endplates in human and monkey biopsies was analysed by immunohistochemisty. By qualitative comparison of staining intensities, it was estimated that IgG1-637 bound to the monkey receptor with 10 fold reduced affinity compared to human receptor. From this it was calculated that three doses of 0.5 mg/kg or 1 mg/kg could be used safely. Female *Macaca mulatta* monkeys between 3 and 4 kg were injected with 3 doses of antibody on consecutive days. Acetylcholine esterase treatment was ready to be injected in case animals developed a myasthenic crisis with respiratory problems. However, none of the treated monkeys showed clinical symptoms of MG (Table 1).

Seven days after the first injection, the animals were anesthetised and the neuromuscular transmission was tested by measuring the muscle compound action potential (CMAP) after repetitive nerve stimulation. For this, decrement in compound muscle action potential (CMAP) was measured in the flexi digiti quinti. Monkeys were anesthetized with ketamine. For stimulation and recording, two small monopolar needle electrodes were placed subcutaneously. To detect a decremental response, 10 repetitive stimuli of 0.2 ms were given at 3, 5 and 10 Hz with an EMG system (Nicolet Biomedical Inc., Madison, Wis., USA). The test was considered positive when the average of three consecutive measurements of the same muscle showed a decrement of at least 10% of both the amplitude and the area of the negative (upward) peak op the CMAP. The animal injected with 0.5 mg/kg/day had a normal neuromuscular transmission, but the monkey injected with 1 mg/kg/day had a decrementing response of the CMAP, which is a typical sign of MG.

Figure 8:
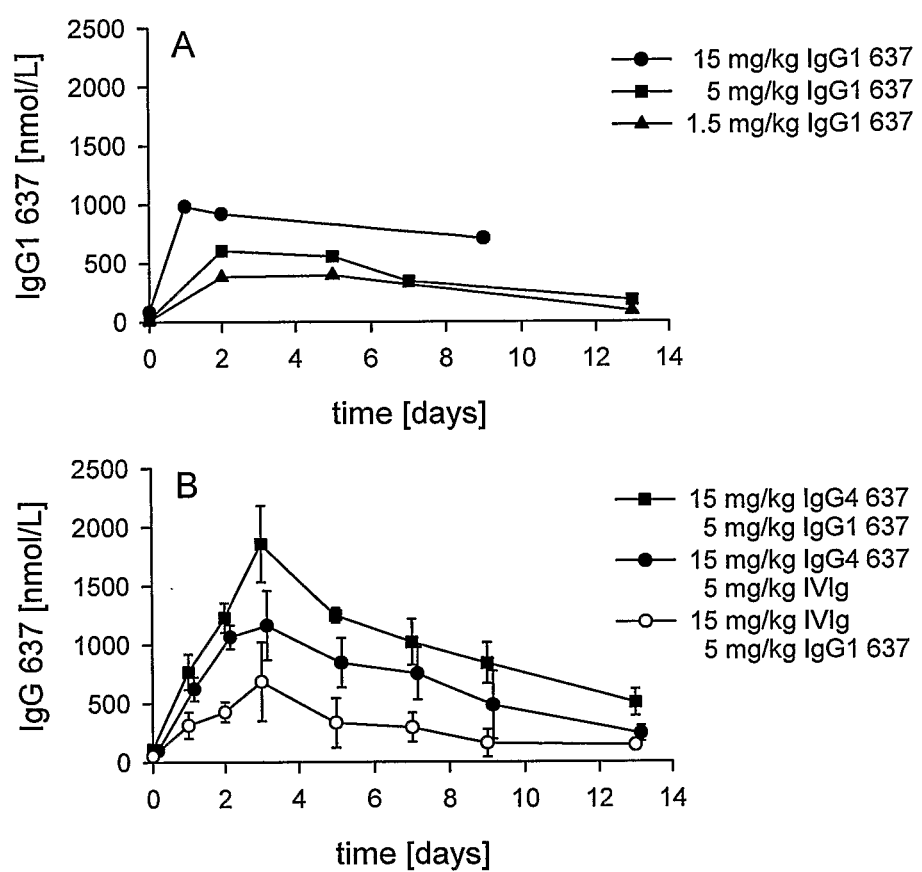
FIG. 8: Anti-AChR antibody titer in the serum of rhesus monkeys. (A) Anti-AChR antibody titer in monkeys injected with different doses of IgG1-637 on day 0, 1 and 2. (B) Average anti-AChR antibody titer (±SD) in monkeys injected on day 0, 1, and 2 with IgG1-637 (n=4), IgG4-637 (n=2) and IgG1-637+IgG4-637+IVIg (n=5). Additional injections of IVIg were given to obtain an equal total dose of human antibody.

Subsequently higher doses of IgG1-637 were tested. At 1.7 mg/kg/day and 5 mg/kg/day (3 doses of antibody on consecutive days, total dose 5 mg/kg and 15 mg/kg) IgG1-637 caused clinical symptoms in all animals (Table 1 and FIG. 12). Symptoms started between 1 and 3 days after the first injection and lasted up to 7 days. At the peak of the disease animals were hypo-active, could not climb because of weakness of the limbs, hands and feet, and had difficulty eating (Osserman grade 2a (Osserman, K E. et al., Mt Sinai J Med 38, 497 (1971)), but no respiratory problems. This phase lasted for 2-3 days. All animals injected with 1.7 mg/kg/day or 5 mg/kg/day IgG1-637 had a decrementing response of the CMAP 7 days after the first injection, even if their condition had already begun to improve. The clinical symptoms paralleled the antibody titre in the serum of the animals, which declined slowly after the second injection of IgG1-637 (FIG. 8, total doses are indicated in the figure).

TABLE 1

Passive transfer of IgG1-637

| number of animals | 3 doses of | decremental response after repetitive nerve stimulation | clinical symptoms |
|---|---|---|---|
| 1 | 0.5 mg/kg | − | − |
| 1 | 1.0 mg/kg | + | − |
| 1 | 5.0 mg/kg | + | + |

Example 7

Proof of Principle: Effect of IgG4-637 in an in vivo Competition Experiment Using the Passive Transfer Model for MG The effect of IgG4-637 was tested in an in vivo competition experiment (FIG. 12): 5 mg/kg/day (total dose 15 mg/kg) of IgG4-637 or human intravenous immunoglobulin (IVIg) were injected in the mornings on 3 consecutive days. Six hours after the first injection, animals received a second injection of 1.7 mg/kg/day (total dose 5 mg/kg) IgG1-637 or IVIg on each of the three experimental days. Blood samples were taken on different days and analysed for anti-human AChR titre using the Acetylcholine Receptor Autoantibody RRA Kit (IBL, Hamburg, Germany).

The animals (n=4) receiving 5 mg/kg/day IVIg and 1.7 mg/kg/day IgG1-637 were clinically ill and had a decremental response of the CMAP. Both the area and the amplitude of the negative (upward) peak decreased more than 22% at 3 and 5 Hz. (FIGS. 9A and 9D, total doses are indicated in the figure). Two animals receiving 5 mg/kg/day IgG4-637 and IVIg did not show any clinical symptoms (FIG. 12) and also the neuromuscular transmission in this animal was normal (FIGS. 9B and 9E). Interestingly, the animals (n=5) which received IgG4-637 in the mornings and IgG1-637 later on the experimental days, did not develop any clinical symptoms (FIG. 12). These animals also did not have an impaired neuromuscular transmission (FIGS. 9C and 9F), despite the fact that these developed the highest titre of antibodies against the AChR (FIG. 8B).

Biopsies of intercostal muscle were taken on day 7 after the first injection of antibodies. The biopsies were frozen immediately on melting isopentane and stored at −80° C. To visualize the administered IgG1-637 and IgG4-637, mouse-antibodies directed against human allotype Gm1(a) (HP6184) and human IgG4 (HP6196) were used. In this respect it is important to note that HP6184 is specific for only a subset of human IgG1, including IgG1-637 (allotype a). In addition both HP6184 and HP6196 were selected for detection of human IgG1 and IgG4 in rhesus monkey, since both mouse antibodies showed to be not cross-reactive with endogenous IgG of rhesus monkey as determined by immunohistochemistry.

For immunohistochemistry frozen biopsies of intercostal muscle were cut at 6 μm using a cryotome, fixated in acetone (10 min, room temperature), blocked for endogenous peroxidase and blocked for aspecific binding to Fc-receptors using 10% normal goat serum. Cryosections were incubated with HP6184 and HP6196 at predetermined optimal dilution and subsequently incubated with FITC conjugated goat-anti-mouse IgG (GaM IgG-FITC) (1:100; 30 min.) and peroxidase conjugated sheep-anti-FITC (Sh-anti-FITC-PO) (1:100; 30 min). Peroxidase (activity) was visualized with amino-ethyl-carbazole (AEC; red color)) and nuclei were stained with hematoxylin (blue). To confirm the localization of AchR in the rhesus muscle, cryosections were stained with Alexa 495 conjugated bungarotoxin (1:300, 30 min).

Figure 10:
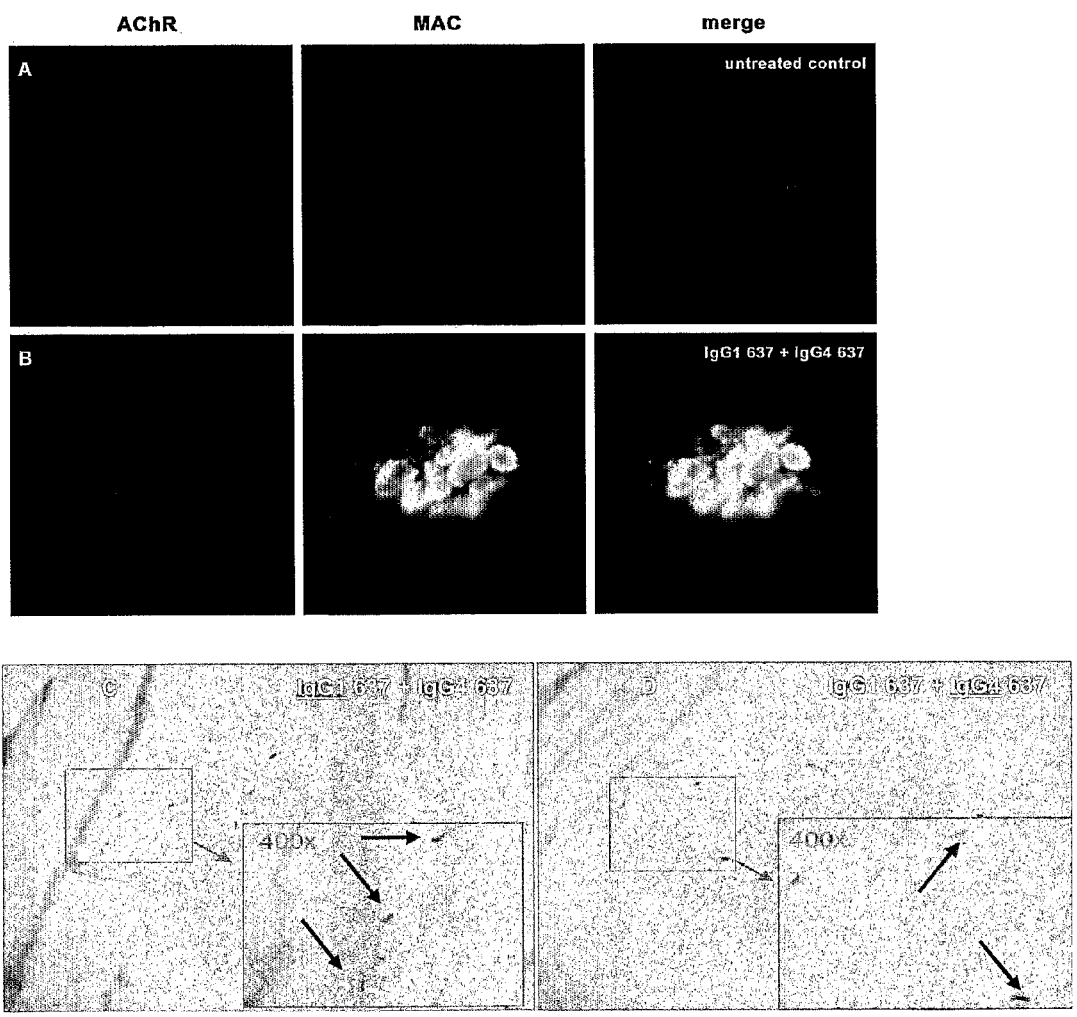
FIG. 10: Analysis of endplates in an intercostals biopsy from (A) an untreated control rhesus monkey and (B-D), a rhesus monkey 7 days after the first injection of 5 mg/kg/day IgG4-637 and 1.7 mg/kg/day IgG1-637. (A,B) Cryosection were double stained for the AChR using rhodamine labeled α-bungarotoxin and for the membrane attack complex of complement using mAb aE11. (C,D) Staining of human IgG1 and IgG4. Both antibodies are present at the neuromuscular junctions (thick arrows) as detected with mouse-anti-human IgG1 (HP6184) and mouse-anti-human IgG4 (MH164-4), respectively. Nuclei were stained with hematoxylin. (E) electron micrograph of an endplate region. Arrows indicate some of the intact folds postsynaptic membrane, the asterisks show the nerve terminal and the arrow head indicates a preparatory artifact. (F) Electron micrograph of endplate regions in intercostals muscles. The asterisks show the nerve terminals, and arrows and arrowheads indicate the folding of the postsynaptic membrane. (10F-A) Endplate region of an animal treated with 5 mg/kg IgG1-637. (10F-B) Endplate region of an animal treated with 15 mg/kg IgG4-637. (10F-C and 10F-D) Endplate regions of two animals treated with 5 mg/kg IgG1-637 and 15 mg/kg IgG4-637.
Figure 10:
Figure 10:
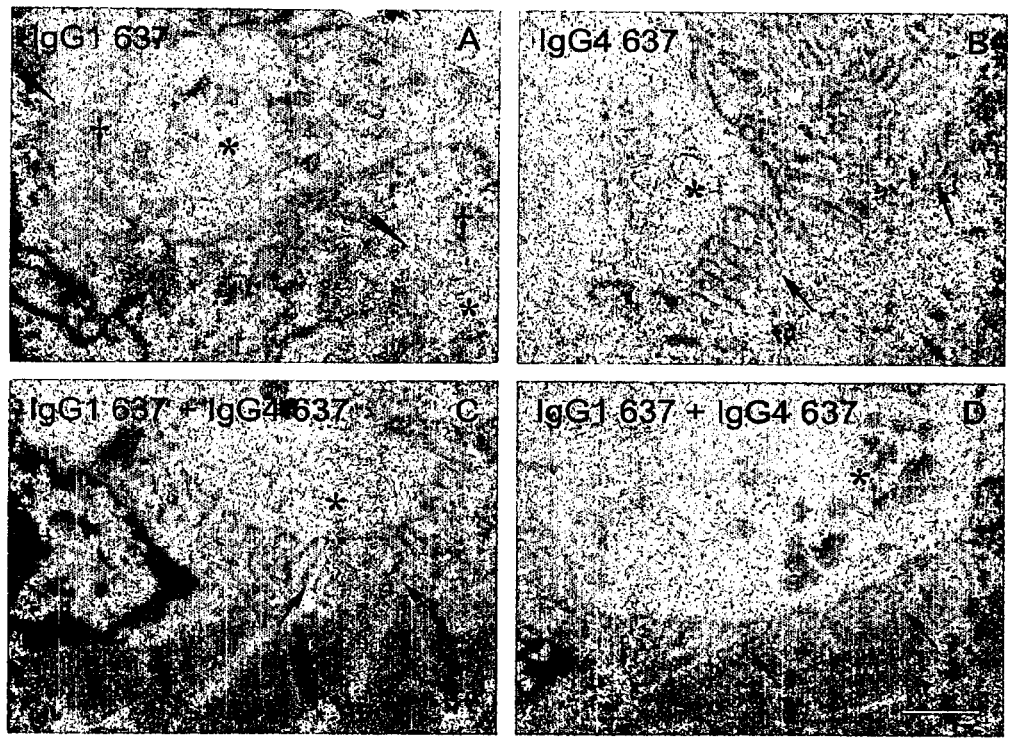

An intercostal biopsy taken from an animal treated with IgG1-637 and IgG4-637 on day 7 showed that both IgG1-637 and IgG4-637 are located at the neuromuscular junctions (FIG. 10C, 10D). Omission of HP6184 or HP6196 resulted in negative staining. The localization of neuromuscular junctions in the muscle biopsy was confirmed by positive staining with bungarotoxin.

The endplates double stained intensively for both AChR (using α-bungarotoxin, FIG. 10B, left), and membrane attack complex (MAC, C5b-9) (FIG. 10B, middle). The same result was obtained using a staining for the complement protein C4 (not shown). No activated complement proteins were found on endplates of an untreated control animal (FIG. 10A). Thus, it seems that IgG4-637 bound to the rhesus monkey endplates but did not completely prevent IgG1-637 binding and complement activation. However, electron microscopic analysis of the biopsies showed that, the ultrastructure of postsynaptic membrane was preserved (FIG. 10E). The typical myasthenic destruction of the postsynaptic folding was absent, indicating that the postsynaptic membrane tolerated some degree of complement activation.

FIG. 10F shows electron micrographs of endplate regions in intercostals muscles. The asterisks show the nerve terminals, and arrows and arrowheads indicate the folding of the postsynaptic membrane. FIG. 10F-A shows the endplate region of an animal treated with 5 mg/kg IgG1-637. This animal had mild muscle weakness but no decrement of the CMAP. The postsynaptic membrane is severely damaged: synaptic cleft is widened (indicated by daggers) and the postsynaptic folds are shallow and widened (indicated by arrowheads). FIG. 10F-B shows the endplate region of an animal treated with 15 mg/kg IgG4-637. The arrows indicate intact postsynaptic folds; the synaptic cleft is adjacent to the nerve terminal. FIGS. 10F-C and 10F-D show endplate regions of two animals treated with 5 mg/kg IgG1-637 and 15 mg/kg IgG4-637. The folding of the postsynaptic membranes is intact (arrows).

An analysis of compound muscle action potentials from rhesus monkeys is shown in FIG. 11 (total doses are indicated in this figure).

Example 8

Antigenic Modulation of Surface AChR of TE671 Cells by Serum from IgG1-637 and/or IgG4-637 Treated Monkeys.

The ability to induce AChR loss by means of antigenic modulation was determined in sera obtained from the antibody treated monkeys, at different timepoints after treatment (FIG. 13A). The same monkeys as indicated in Example 7 were used in short, monkeys were injected as described in example 7 with the respective antibodies on day 0, 1 and 2. Confluent TE671 cells were treated with cycloheximide and sera from antibody treated monkeys; sera were diluted to a final concentration of 637 antibody concentration of 0.1 nM. Serum from IgG1-637 treated animals induced maximum degradation of surface AChR by day 3. Serum from IgG4-637 treated animals did not induce antigenic modulation at the same antibody concentration. Serum from the monkeys injected with the combination of IgG1-637 and IgG4-637 induced an intermediate level of antigenic modulation. Thus, the ability of IgG4-637 to induce antigenic modulation changed after presence of this antibody in the rhesus monkey (compare to example 5 and FIG. 7). This could indicate that during the presence in the rhesus monkey the properties of IgG4-637 changed in such way that IgG4-637 obtained monovalent binding properties, thereby loosing the ability to cross-link the AChR. One mechanism by which IgG4-637 could obtain monovalent binding properties would be in vivo exchange with monkey IgG4, similar to a mechanism proposed in humans (Aalberse and Schuurman (2002) Immunology 105:9-19).

To investigate the protective effect of the sera derived from the 637 treated monkeys, TE671 cells were treated with 1 nM IgG1 637 and dilutions of the monkey sera (diluted to a final concentration of 637 antibody concentration of 10, 1 or 0.1 nM) (FIG. 13B). Addition of serum of monkeys treated with IgG1-637 aggravated AChR loss. Serum obtained at day 5 from monkeys treated with IgG4-637 almost completely prevented antigenic modulation. This again indicates that the properties of IgG4-637 changed after incubation in the rhesus monkey, suggesting that IgG4-637 obtained monovalent binding properties capable of blocking the antigen-modulation induced by IgG1-637.

Example 9

Construction of pConG1f7D8: A Vector for Production of the Heavy Chain of 7D8-IgG1

The $V_H$ coding region of CD20 specific HuMab-7D8 (WO 04/035607) was amplified by PCR from a pGemT (Promega, Madison, USA) vector containing this region using the primers 7D8VHexfor and 2F8HCexrev (FIG. 1), introducing suitable restriction sites for cloning into pConG1f0.4 (Lonza Biologics, Slough, UK), a mammalian expression vector containing the genomic constant region (allotype f) of human IgG1, and an ideal Kozak sequence (GCCGCCACC, (Kozak M et al., Gene 234(2), 187-208 (1999)). The PCR fragment was cloned in pPCR-Script CAM (Stratagene, Amsterdam, The Netherlands) using a PCR-Script® Cam Cloning Kit (Stratagene), according to the manufacture's instructions. Several clones were sequenced and a clone containing the predicted sequence was chosen for further use.

The $V_H$ fragment was gel purified and cloned into pConG1f0.4. For this the $V_H$ fragment was isolated from the pPCR-Script CAM vector after digestion with HindIII and ApaI and gel purification.

The pConG1f0.4 vector was digested with HindIII and ApaI and the vector fragment was isolated from gel, followed by dephosphorylation with Shrimp Alkaline Phosphatase (New England Biolabs) The $V_H$ fragment and the pConG1f0.4HindIII-ApaI dephosphorylated fragment were ligated and transformed into competent DH5α-T1$^R$ cells (Invitrogen). Eight colonies were checked by colony PCR (using primers pConG1seq1 and HCseq5 (FIG. 1) and all colonies were found to contain the correct insert size. A clone was chosen for further study and named pConG1f7D8.

Example 10

Construction of pConK7D8: A Vector for Production of the Light Chain of 7D8-IgG1, 7D8-IgG4 and 7D8-HG The $V_L$ coding region of CD20 specific HuMab-7D8 (WO 04/035607) was amplified from a plasmid containing this region using the primers 7D8VLexfor and 7D8VLexrev (FIG. 1), introducing suitable restriction sites for cloning into pConKappa0.4 (Lonza Biologics), a mammalian expression vector containing the constant kappa light chain region (allotype km3) of human IgG, and an ideal Kozak sequence.

The PCR product and the pConKappa0.4 vector were digested with HindIII and BsiWI. The vector and $V_L$ fragment were purified and the vector was dephosphorylated with Shrimp Alkaline Phosphatase. The $V_L$ fragment and the pConKappa0.4HindIII-BsiWI digested vector were ligated and transformed into competent DH5α T1$^R$ *E. coli*. Ten colonies were checked by colony PCR (using primers pConKseq1 and LCseq3 (FIG. 1) and 9 colonies were found to contain the correct insert size.

From 4 clones plasmid DNA was isolated and the $V_L$ region was sequenced. 3 clones contained the predicted sequence and one clone was chosen for further use and named pConK7D8.

Example 11

Construction of pTomG4: A Vector for the Expression of Variable Heavy Chain Regions of Human IgG with the Constant Region of Human IgG4

Genomic DNA was isolated from a blood sample of a volunteer and used as a template in a PCR with primers IgG4gene2f and IgG4gene2r (FIG. 1), amplifying the complete genomic constant region of the heavy chain of IgG4 and introducing suitable restriction sites for cloning into the mammalian expression vector pEE6.4 (Lonza Biologics). The PCR fragment was purified and cloned into pEE6.4. For this the PCR product was digested with HindIII and EcoRI, followed by heat inactivation of the restriction enzymes. The pEE6.4 vector was digested HindIII and EcoRI, followed by heat inactivation of the restriction enzymes and dephosphorylation of the vector fragment with shrimp alkaline phosphatase, followed by heat inactivation of the phosphatase. The IgG4 fragment and the pEE6.4HindIII/EcoRI dephosphorylated vector were ligated and transformed into competent MACH1-T1$^R$ cells (Invitrogen). Three clones were grown in LB and plasmid DNA was isolated from a small culture (1.5 ml). Restriction digestion revealed a pattern consistent with the cloning of the IgG4 fragment in the pEE6.4 vector. Plasmid DNA from two clones was transformed in DH5α-T1$^R$ *E. coli* and plasmid DNA was isolated and the constructs were checked by sequence analysis of the insert and one clone was found to be identical to a genomic IgG4 clone from the Genbank database, apart from some minor differences in introns. These differences are presumably either polymorphisms or sequence faults in the Genbank sequence. The plasmid was named pTomG4. SEQ ID No: 14 shows the sequence of the IgG4 region encoded by pTomG4.

Example 12

Construction of pTomG47D8: A Vector for the Production of the Heavy Chain of 7D8-IgG4

Plasmid DNA from pConG1f7D8 was digested with HindIII and ApaI and the $V_H$ fragment was gel purified. The pTomG4 vector was digested with HindIII and ApaI and the vector fragment was isolated from gel. The $V_H$ fragment and the pTomG4HindIII-ApaI fragment were ligated and transformed into competent DH5α-T1$^R$ cells. Four colonies were checked by colony PCR (using primers pConKseq1 and HCseq11 (FIG. 1)) and two were found to contain the correct insert size and the presence of the pTomG4 backbone was confirmed by a digestion with MspI on the colony PCR fragment. One of the clones was chosen for further use. This plasmid was named pTomG47D8.

Example 13

Construction of pTomG47D8HG; A Vector for the Expression of the Heavy Chain of 7D8-HG Site directed mutagenesis was used to destroy the splice donor site of the hinge exon of IgG4 in the pTomG47D8 plasmid. A site-directed mutagenesis reaction was done according to the QuickChange XL site-directed mutagenesis method using primers IgG4S228Pf and IgG4S228Pr. 24 colonies were screened by colony PCR and XmaI digestion (an extra XmaI site was introduced during mutagenesis) and all colonies appeared to contain the correct nucleotide changes. Two positive colonies were grown overnight, plasmid DNA was isolated and sequenced to confirm that the correct mutation was introduced. Both did contain the correct sequence and one was chosen for further propagation and named pTomG47D8HG. To exclude the introduction of additional mutations during the mutagenesis process, the whole IgG4 coding region of pTomG47D8HG was resequenced and no additional mutations were found. The final vector was named pTomG47D8HG.

Example 14

Production of 7D8-IgG4 and 7D8-HG (hingeless), by Transient Expression in Hek-293F Cells Antibodies were produced of all constructs by cotransfecting the relevant heavy and light chain vectors in HEK-293F cells using 293fectin according to the manufacturer's instructions. For 7D8-IgG1, pConG1f7D8 and pConK7D8 were coexpressed. For 7D8-IgG4, pTomG47D8 and pConK7D8 were coexpressed. For 7D8-HG, pTomG47D8HG and pConK7D8 were coexpressed.

Example 15

Purification of IgG4 and IgG4-Hingeless Antibodies

All IgG4 and hingeless antibodies were purified. First the supernatants were filtered over 0.20 µM dead-end filter. Then, the supernatant was loaded on a 5 ml Protein A column (rProtein A FF, Amersham Bioscience) and eluted with 0.1 M citric acid-NaOH, pH 3. The eluate was immediately neutralized with 2 M Tris-HCl, pH 9 and dialyzed overnight to 12.6 mM sodium phosphate, 140 mM NaCl, pH 7.4 (B. Braun, Oss, The Netherlands). After dialysis samples were sterile filtered over 0.20 µM dead-end filter.

Antibodies were deglycosylated by overnight incubation at 37° C. with 1 unit PNgase F (Roche)/µg antibody, followed by purification on protein A.

Samples were analysed for concentration of IgG by nephelometry and absorbance at 280 nm.

Example 16

Pharmacokinetic Evaluation of an IgG4 Hingeless Mutant Antibody in Human IgG-supplemented SCID Mice.

Sixteen SCID mice (C.B-17/lcrCrl-scid-BR, Charles-River) with body weights between 18 and 22 g were used for the experiment. The mice were housed in a barrier unit of the Central Laboratory Animal Facility (Utrecht, The Netherlands) and kept under sterile conditions in filter-top cages with water and food provided ad libitum. All experiments were approved by the Utrecht University animal ethics committee.

Immunodeficient SCID mice were chosen for studying the pharmacokinetics of the hingeless IgG4 variant, because these mice do not develop antibody responses to human proteins which may affect clearance studies with durations of more than one week. These IgG-deficient mice were supplemented with a high dose of intravenous immunoglobulin (human multidonor polyclonal IgG) to study the clearance of hingeless IgG4 mutant in the presence of human IgG at physiologically relevant concentrations. This provides a mouse model which closely represents the conditions in humans, because 1) association of hingeless IgG4 into a bivalent form is prevented by the presence of IVIG, and 2) hingeless IgG4 has to compete with other IgG for binding to the neonatal Fc receptor (FcRn). Binding to FcRn protects IgG from intracellular degradation after endocytosis and is responsible for its long plasma half-life.

In this model the plasma clearance was studied of variants from the human CD20 specific human mAb clone 7D8. The clearance rate of the hingeless IgG4 variant (7D8-HG, lot 992-001-EP) was compared with that of normal human IgG4 (7D8-IgG4, lot 992-002-EP), of F(ab')$_2$ fragments from 7D8 IgG1 (7D8-F(ab')$_2$, lot 892-020-XX). In addition, a preparation of the hingeless variant tested that was enzymatically deglycosylated (TH3001-7D8-HG deglyc, lot 991-004-EP). Each antibody was administered to 4 mice via the tail vein, at a dose of 0.1 mg in 200 µl, corresponding to a dose of about 5 mg per kg of body weight. The monoclonal antibodies were administered in a 1:1 mixture with Intravenous Immunoglobulin (60 mg/ml, Sanquin, The Netherlands, JFK108ST, charge #04H04H443A). The total injected volume was 400 µl/mouse, giving an IVIG dose of 12.5 mg per mouse.

Fifty µl blood samples were collected from the saphenal vein at 15 minutes, 5 hours, 24 hours, 2 days, 3 days, 7 days, and 10 days after administration. Blood was collected into heparin containing vials and centrifuged for 10 minutes at 14,000 g. Plasma was stored at −20° C. for determination of mAb concentrations. Plasma concentrations of the 7D8 variants were determined using a sandwich ELISA. A mouse mAb anti-7D8-idiotype antibody (clone 2F2 SAB 1.1 (LD2), lot 0347-028-EP) was used as capturing antibody. After blocking plates with PBS supplemented with 0.05% Tween and 2% chicken serum, samples were added, serially diluted in ELISA buffer (PBS supplemented with 0.05% Tween 20 and 2% chicken serum), and incubated on a plate shaker for 2 h at room temperature (RT). The infused antibodies were used as reference. After washing, the plates were subsequently incubated with peroxidase-labeled goat anti-human F(ab')$_2$ specific (109-035-097, Jackson Immunoresearch, West Grace, Pa.) and developed with 2,2'-azino-bis(3-ethylbenz-thiazoline-6-sulfonic acid) (ABTS; Roche, Mannheim, Germany). Absorbance was measured in a microplate reader (Biotek, Winooski, Vt.) at 405 nm. Total human IgG plasma concentrations were determined using a similar ELISA. Mouse mAb anti-human IgG-kappa clone MH16 (#M1268, CLB Sanquin, The Netherlands) was used as capturing antibody. Peroxidase-labeled goat anti-human IgG immunoglobulin (#109-035-098, Jackson, West Grace, Pa.) was used for detection.

Pharmacokinetic analysis was done by determining the area under the curve (AUC) from the concentration—time curves, with tail correction. The plasma clearance rate was calculated as Dose/AUC (ml/day). Statistical testing was performed using GraphPad PRISM vs. 4 (Graphpad Software).

Figure 14:
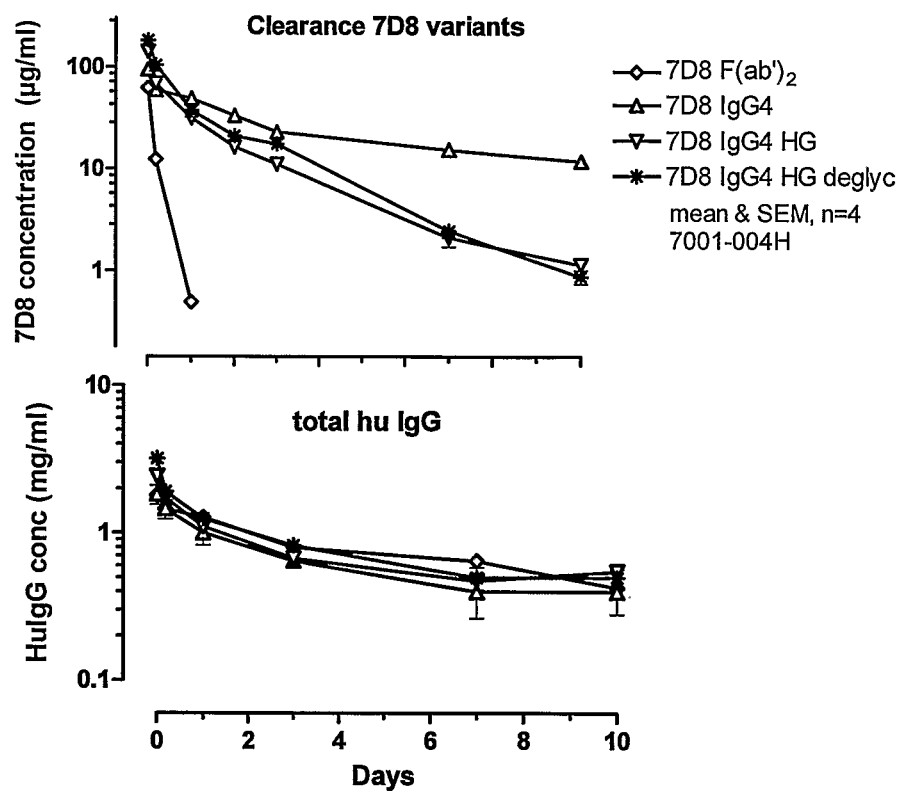
FIG. 14: Clearance of 7D8 variants in IVIG supplemented SCID mice. The figure shows in the upper panel semi-logarithmic plots of the concentrations of the mAb 7D8 variants in time and in the lower panel the total human IgG concentrations.

FIG. 14 shows in the upper panel semi-logarithmic plots of the concentrations of the mAb 7D8 variants in time and in the lower panel the total human IgG concentrations. The initial total human IgG concentrations were on average 2.3 mg/ml and declined to 0.47 mg/ml after 10 days. The initial plasma concentrations of 7D8 IgG4 and IgG4 HG variants were in the range of 94 to 180 µg/ml, which is consistent with an initial distribution into the plasma compartment of the mice. For the F(ab')2 fragments the initial concentrations were somewhat lower, on average 62 µg/ml. The upper panel makes clear that the clearance of the hingeless variant, including the deglycosylated preparation, is somewhat faster than that of intact IgG4, but much slower than that of F(ab')2 fragments. The table below shows the clearance rates calculated from the concentration-time curves. The clearance rate of the hingeless variant was 2 to 3 times higher than that of normal IgG4. However, it was almost 10 times slower than that of F(ab')$_2$ fragments. Importantly, deglycosylation had no significant effect on the rate of clearance of the hingeless IgG4 variant.

| PLASMA CLEARANCE RATE (D/AUC) in ml/day per kg | IgG1 F(ab')2 | IgG4 | IgG4 HG | IgG4 HG deglyc |
|---|---|---|---|---|
| Mean | 380 | 14 | 39 | 29 |
| Lower 95% CI of mean | 346 | 12 | 25 | 19 |
| Upper 95% CI of mean | 415 | 17 | 53 | 38 |
| Number of values | 4 | 4 | 4 | 4 |

Thus, in the presence of human IgG in pnysiologically relevant concentrations the clearance of the hingeless variant is much slower than that of F(ab')2 fragments, which have a comparable molecular size. This experiment demonstrates that, in the presence of competing human IgG at physiologically relevant concentrations, the hingeless IgG4 variant is capable of functional interaction with the neonatal Fc receptor (FcRn). Furthermore, this experiment indicates that the glycosylation of the hingeless IgG4 variant does not affect plasma clearance and that non-glycosylated hingeless IgG4 has a similar half-life in vivo as the fully glycosylated form.

SEQUENCE LISTING

SEQ ID No: 1
```
  1 gaggttcagc tgctcgagtc tggggggagac ttggtcaagc ctggagggtc 51 cctgagactc tcctgtgcag cctctggatt caaatccact gactactaca 101 tggcctgggt ccgccaggct ccagggaggg ggctggagtg ggtctcattc 151 attagtggtc gtgttttcac aaactacacc gcctctgtga ggggccgatt 201 caccgtcttc agagaggacg acaacacctc ggtgtatctt cagatgagcc 251 gcctgagagt cgaagacacg gccgtctact actgtgcgag actgcgggga 301 atttttcgag ggccctcaa accctagag tactacttcg atctctgggg 351 ccgtggcacc ctggtcactg tctcatcg
```

SEQ ID No: 2
```
  1 EVQLLESGGD LVKPGGSLRL SCAASGFKST DYYMAWVRQA PGRGLEWVSF

51 ISGRVFTNYT ASVRGRFTVF REDDNTSVYL QMSRLRVEDT AVYYCARLRG

101 IFRGPLKPLE YYFDLWGRGT LVTVSS
```

SEQ ID No: 3
```
  1 gagatcgagc tcactcagcc ccactctgtg tcggagtctc cggggaagac 51 ggtaaccatc tcctgcaccc gcagcagtgg cagcattgcc agcaactatg 101 tgcagtggta ccagcagcgc ccgggcagtt cccccaccac tgtgatctat 151 gaggataacc aaagaccctc tggggtccct gatcggttct ctggctccat 201 cgacagctcc tccaactctg cctccctcac catctctgga ctgaagactg 251 aggacgaggc tgactactac tgtcagtctt atgatagcaa ctctgggggg 301 agggtgttcg gcggagggac caagctgacc gtc
```

SEQ ID No: 4
```
  1 EIELTQPHSV SESPGKTVTI SCTRSSGSIA SNYVQWYQQR PGSSPTTVIY

51 EDNQRPSGVP DRFSGSIDSS SNSASLTISG LKTEDEADYY CQSYDSNSGG

101 RVFGGGTKLT V
```

SEQUENCE LISTING

SEQ ID No: 5

```
   1 gctagcacca agggcccatc cgtcttcccc ctggcgccct gctccaggag
  51 cacctccgag agcacagccg ccctgggctg cctggtcaag gactacttcc
 101 ccgaaccggt gacggtgtcg tggaactcag gcgccctgac cagcggcgtg
 151 cacaccttcc cggctgtcct acagtcctca ggactctact ccctcagcag
 201 cgtggtgacc gtgccctcca gcagcttggg cacgaagacc tacacctgca
 251 acgtagatca caagcccagc aacaccaagg tggacaagag agttggtgag
 301 aggccagcac agggagggag ggtgtctgct ggaagccagg ctcagccctc
 351 ctgcctggac gcacccggc tgtgcagccc agcccaggg cagcaaggca
 401 tgccccatct gtctcctcac ccggaggcct ctgaccaccc cactcatgct
 451 cagggagagg gtcttctgga ttttccacc aggctccggg cagccacagg
 501 ctggatgccc ctaccccagg ccctgcgcat acaggggcag gtgctgcgct
 551 cagacctgcc aagagccata tccgggagga ccctgcccct gacctaagcc
 601 caccccaaag gccaaactct ccactccctc agctcagaca ccttctctcc
 651 tcccagatct gagtaactcc caatcttctc tctgcagagt ccaaatatgg
 701 tcccccatgc ccatcatgcc caggtaagcc aacccaggcc tcgccctcca
 751 gctcaaggcg ggacaggtgc cctagagtag cctgcatcca gggacaggcc
 801 ccagccgggt gctgacgcat ccacctccat ctcttcctca gcacctgagt
 851 tcctggggg accatcagtc ttcctgttcc ccccaaaacc caaggacact
 901 ctcatgatct cccggacccc tgaggtcacg tgcgtggtgg tggacgtgag
 951 ccaggaagac cccgaggtcc agttcaactg gtacgtggat ggcgtggagg
1001 tgcataatgc caagacaaag ccgcgggagg agcagttcaa cagcacgtac
1051 cgtgtggtca gcgtcctcac cgtcctgcac caggactggc tgaacggcaa
1101 ggagtacaag tgcaaggtct ccaacaaagg cctcccgtcc tccatcgaga
1151 aaaccatctc caaagccaaa ggtgggaccc acggggtgcg agggccacat
1201 ggacagaggt cagctcggcc cacctctgc cctgggagtg accgctgtgc
1251 caacctctgt ccctacaggg cagccccgag agccacaggt gtacaccctg
1301 cccccatccc aggaggagat gaccaagaac caggtcagcc tgacctgcct
1351 ggtcaaaggc ttctacccca gcgacatcgc cgtggagtgg gagagcaatg
1401 ggcagccgga gaacaactac aagaccacgc ctcccgtgct ggactccgac
1451 ggctccttct cctctacag caggctaacc gtggacaaga gcaggtggca
1501 ggaggggaat gtcttctcat gctccgtgat gcatgaggct ctgcacaacc
1551 actacacaca gaagagcctc tccctgtctc tgggtaaa
```

SEQ ID No: 6

```
   1 ASTKGPSVFP LAPCSRSTSE STAALGCLVK DYFPEPVTVS WNSGALTSGV
  51 HTFPAVLQSS GLYSLSSVVT VPSSSLGTKT YTCNVDHKPS NTKVDKRVES
 101 KYGPPCPSCP APEFLGGPSV FLFPPKPKDT LMISRTPEVT CVVVDVSQED
 151 PEVQFNWYVD GVEVHNAKTK PREEQFNSTY RVVSVLTVLH QDWLNGKEYK
```

```
201 CKVSNKGLPS SIEKTISKAK GQPREPQVYT LPPSQEEMTK NQVSLTCLVK

251 GFYPSDIAVE WESNGQPENN YKTTPPVLDS DGSFFLYSRL TVDKSRWQEG

301 NVFSCSVMHE ALHNHYTQKS LSLSLGK

SEQ ID No: 7
  1 ctaggtcagc ccaaggctgc ccctcggtc actctgttcc cgccctcctc 51 tgaggagctt caagccaaca aggccacact ggtgtgtctc ataagtgact 101 tctacccggg agccgtgaca gtggcctgga aggcagatag cagccccgtc 151 aaggcgggag tggagaccac cacaccctcc aaacaaagca caacaagta 201 cgcggccagc agctacctga gcctgacgcc tgagcagtgg aagtcccaca 251 gaagctacag ctgccaggtc acgcatgaag ggagcaccgt ggagaagaca 301 gtggccccta cagaatgttc a SEQ ID No: 8
  1 LGQPKAAPSV TLFPPSSEEL QANKATLVCL ISDFYPGAVT VAWKADSSPV

51 KAGVETTTPS KQSNNKYAAS SYLSLTPEQW KSHRSYSCQV THEGSTVEKT

VAPTECS

SEQ ID No: 19: wildtype C$_H$ region of human IgG4
  1 ASTKGPSVFP LAPCSRSTSE STAALGCLVK DYFPEPVTVS WNSGALTSGV

51 HTFPAVLQSS GLYSLSSVVT VPSSSLGTKT YTCNVDHKPS NTKVDKRVES

101 KYGPPCPSCP APEFLGGPSV FLFPPKPKDT LMISRTPEVT CVVVDVSQED

151 PEVQFNWYVD GVEVHNAKTK PREEQFNSTY RVVSVLTVLH QDWLNGKEYK

201 CKVSNKGLPS SIEKTISKAK GQPREPQVYT LPPSQEEMTK NQVSLTCLVK

251 GFYPSDIAVE WESNGQPENN YKTTPPVLDS DGSFFLYSRL TVDKSRWQEG

301 NVFSCSVMHE ALHNHYTQKS LSLSLGK

SEQ ID No: 20: hingeless C$_H$ region of a human IgG4.
  1 ASTKGPSVFP LAPCSRSTSE STAALGCLVK DYFPEPVTVS WNSGALTSGV

51 HTFPAVLQSS GLYSLSSVVT VPSSSLGTKT YTCNVDHKPS NTKVDKRVAP

101 EFLGGPSVFL FPPKPKDTLM ISRTPEVTCV VVDVSQEDPE VQFNWYVDGV

151 EVHNAKTKPR EEQFNSTYRV VSVLTVLHQD WLNGKEYKCK VSNKGLPSSI

201 EKTISKAKGQ PREPQVYTLP PSQEEMTKNQ VSLTCLVKGF YPSDIAVEWE

251 SNGQPENNYK TTPPVLDSDG SFFLYSRLTV DKSRWQEGNV FSCSVMHEAL

301 HNHYTQKSLS LSLGK
```

The invention claimed is:

1. A method for treatment of myasthenia gravis, which method comprises administering to a subject in need thereof an antibody comprising heavy and light chain variable region sequences set forth in SEQ ID NOs: 2 and 4, respectively, for binding to the nicotinic acetylcholine receptor of the muscle, wherein said antibody comprises a light chain and a heavy chain, (i) wherein said antibody is an IgG4 isotype, or (ii) wherein:
   a) said light chain comprises a variable ($V_L$) region and a constant ($C_L$) region of an Ig, and
   b) said heavy chain comprises a variable ($V_H$) region and a constant ($C_H$) region of human IgG4, wherein the amino acid sequence of the constant ($C_H$) region has been modified so that the hinge region does not contain any amino acid residues which participate in the formation of disulphide bonds with other peptides comprising an identical amino acid sequence of the constant ($C_H$) region of the human IgG4.

2. The method according to claim 1, wherein the antibody is a human antibody.

3. The method according to claim 1, wherein the heavy chain as specified in subsection (ii)(b) comprises a variable ($V_H$) region and a constant ($C_H$) region of human IgG4, wherein the amino acid sequence of the heavy chain has been modified such that the region corresponding to the hinge region does not comprise any cysteine residues.

4. The method according to claim 1, wherein the heavy chain as specified in subsection (ii)(b) comprises a variable ($V_H$) region and a constant ($C_H$) region of human IgG4, wherein the amino acid sequence of the heavy chain has been modified such that the amino acid residues corresponding to amino acid residues 106 and 109 of the sequence of SEQ ID No: 19 have been substituted with amino acid residues different from cysteine.

5. The method according to claim 1, wherein the heavy chain as specified in subsection (ii)(b) comprises a variable ($V_H$) region and a constant ($C_H$) region of human IgG4, wherein the amino acid residues corresponding to amino acid residues 106 to 109 of the sequence of SEQ ID No: 19 have been deleted.

6. The method according to claim 1, wherein the heavy chain as specified in subsection (ii)(b) comprises a variable ($V_H$) region and a constant ($C_H$) region of human IgG4, wherein the amino acid residues corresponding to amino acid residues 99 to 110 of the sequence of SEQ ID No: 19 have been deleted.

7. The method according to claim 1, wherein the heavy chain as specified in subsection (ii)(b) comprises a variable ($V_H$) region and a constant ($C_H$) region of human IgG4, wherein the amino acid sequence of the constant ($C_H$) region comprises the sequence as set forth in SEQ ID NO:20.

* * * * *